US012065512B2

(12) United States Patent
Endo et al.

(10) Patent No.: US 12,065,512 B2
(45) Date of Patent: Aug. 20, 2024

(54) CYCLIC PEPTIDE AND A MEDICAMENT, EXTERNAL PREPARATION AND COSMETIC COMPRISING SAID CYCLIC PEPTIDE

(71) Applicant: Igisu Co., Ltd., Tokyo (JP)

(72) Inventors: Kyoko Endo, Sendai (JP); Yori Endo, Sendai (JP)

(73) Assignee: Igisu Co., Ltd., Tokyo (JP)

( * ) Notice: Subject to any disclaimer, the term of this patent is extended or adjusted under 35 U.S.C. 154(b) by 406 days.

(21) Appl. No.: 16/745,520

(22) Filed: Jan. 17, 2020

(65) Prior Publication Data

US 2020/0347096 A1 Nov. 5, 2020
US 2021/0277062 A9 Sep. 9, 2021

Related U.S. Application Data

(62) Division of application No. 15/122,753, filed as application No. PCT/JP2016/065839 on May 27, 2016.

(30) Foreign Application Priority Data

May 29, 2015 (JP) ................................ 2015-110622

(51) Int. Cl.
| | |
|---|---|
| *A61K 38/00* | (2006.01) |
| *A61K 8/64* | (2006.01) |
| *A61K 38/10* | (2006.01) |
| *A61K 38/12* | (2006.01) |
| *A61P 17/14* | (2006.01) |
| *A61Q 5/02* | (2006.01) |
| *A61Q 5/12* | (2006.01) |
| *A61Q 7/00* | (2006.01) |
| *A61Q 17/04* | (2006.01) |
| *A61Q 19/00* | (2006.01) |
| *A61Q 19/02* | (2006.01) |
| *A61Q 19/04* | (2006.01) |
| *A61Q 19/06* | (2006.01) |
| *A61Q 19/08* | (2006.01) |
| *A61Q 19/10* | (2006.01) |
| *C07K 7/00* | (2006.01) |
| *C07K 7/08* | (2006.01) |
| *C07K 7/64* | (2006.01) |

(52) U.S. Cl.
CPC ............... *C07K 7/64* (2013.01); *A61K 8/64* (2013.01); *A61K 38/10* (2013.01); *A61K 38/12* (2013.01); *A61P 17/14* (2018.01); *A61Q 5/02* (2013.01); *A61Q 5/12* (2013.01); *A61Q 7/00* (2013.01); *A61Q 17/04* (2013.01); *A61Q 19/00* (2013.01); *A61Q 19/02* (2013.01); *A61Q 19/04* (2013.01); *A61Q 19/06* (2013.01); *A61Q 19/08* (2013.01); *A61Q 19/10* (2013.01); *C07K 7/08* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,114,923 A | 5/1992 | Seilhamer et al. | |
| 5,674,710 A | 10/1997 | Seilhamer et al. | |
| 6,028,055 A | 2/2000 | Lowe et al. | |
| 6,818,619 B2 | 11/2004 | Burnett, Jr. et al. | |
| 7,425,531 B2 | 9/2008 | Lanctot et al. | |
| 7,648,962 B2 | 1/2010 | James et al. | |
| 2004/0138134 A1 | 7/2004 | Golembo et al. | |
| 2008/0207505 A1 | 8/2008 | James | |
| 2012/0238498 A1* | 9/2012 | Endo ..................... | A61K 45/06 514/12.4 |
| 2018/0066020 A1 | 3/2018 | Endo et al. | |

FOREIGN PATENT DOCUMENTS

| | | |
|---|---|---|
| AU | 2012207816 A1 | 8/2013 |
| EP | 2457581 A1 | 5/2012 |
| EP | 2471546 A1 | 7/2012 |
| EP | 2666475 A1 | 11/2013 |
| JP | H03505280 A | 11/1991 |
| JP | 2006-515579 A | 6/2006 |
| JP | 2007-525213 A | 9/2007 |
| JP | 2008-509746 A | 4/2008 |
| WO | WO 1989/012069 A1 | 12/1989 |

(Continued)

OTHER PUBLICATIONS

"Prevent", Macmillan Dictionary, available online at www.macmillandictionary.com/US/dictionary/american/prevent, 6 pages (accessed on May 12, 2022) (Year: 2022).*
"Treat", The Free Dictionary, available online at www.thefreedictionary.com/treat, 11 pages (accessed on May 12, 2022) (Year: 2022).*
Vining, A., "Is Baldness Preventable," WebMD, available online at https://www.webmd.com/connect-to-care/hair-loss/is-baldness-preventable, 7 pages (accessed on May 12, 2022) (Year: 2022).*
Mcintosh, J., "What's to know about alopecia areata," Medical News Today, available online at https://www.medicalnewstoday.com/articles/70956, 19 pages (2017) (Year: 2017).*

(Continued)

*Primary Examiner* — Thea D' Ambrosio
(74) *Attorney, Agent, or Firm* — Wolf, Greenfield & Sacks, P.C.

(57) ABSTRACT

The present invention is aimed for providing a novel peptide with a high drug efficacy and strong effect, a medicament or external preparation comprising it, specifically a prophylactic or therapeutic for dermatitis, rhinitis or alopecia, or a hair growth stimulant, a hair growing agent, an antipruritic or a skin-care product. The present invention achieved said aim by providing a cyclic peptide having an amino acid sequence expressed by the Formula I or a derivative thereof or a pharmaceutically acceptable salt thereof, wherein the amino acid sequence does not have a peptide bond that is not between the amino acids constituting the amino acid sequence.

6 Claims, 1 Drawing Sheet
Specification includes a Sequence Listing.

(56) References Cited

FOREIGN PATENT DOCUMENTS

| WO | WO 2002/074234 A2 | 9/2002 | |
|---|---|---|---|
| WO | WO 2004/011498 A2 | 2/2004 | |
| WO | WO 2004/047871 A2 | 6/2004 | |
| WO | WO 2005/072055 A2 | 8/2005 | |
| WO | WO-2005116655 A2 * | 12/2005 | ....... A61K 47/48215 |
| WO | WO 2006/020841 A2 | 2/2006 | |
| WO | WO-2006076471 A2 * | 7/2006 | ............. C07K 14/58 |
| WO | WO 2008/032450 A1 | 3/2008 | |
| WO | WO 2008/140125 A1 | 11/2008 | |
| WO | WO 2010/002583 A2 | 1/2010 | |
| WO | WO 2011/010732 A1 | 1/2011 | |
| WO | WO 2011/024973 A1 | 3/2011 | |
| WO | WO 2012/099258 A1 | 7/2012 | |

OTHER PUBLICATIONS

"Alopecia Areata (AA)", Familydoctor.org, available online at https://familydoctor.org/condition/alopecia-areata/#:~:text=The%20condition%20cannot%20be%20prevented,family%20history%20of%20alopecia%20areata, 4 pages (2021) (Year: 2021).*

[No Author Listed] Imino Acid Definition. Biology Online Dictionary. Retrieved from https://www.biology-online.org/dictionary/imino_acid. Accessed Jan. 22, 2019. 3 pages.

[No Author Listed] Medicament Definition. Merriam-Webster Online Dictionary. Retrieved from https://www.merriam-webster.com/dictionary/medicament. Accessed Aug. 12, 2019. 11 pages.

[No Author Listed] UniProt Database: Accession No. P16860. 1990. 12 pages.

Akizuki et al., Cloning and sequence analysis of complementary DNA encoding a precursor for chicken natriuretic peptide. FEBS Lett. Mar. 25, 1991;280(2):357-62.

Jennings et al., The disulfide bonded ring of iso-rANP, unlike that of rANP, has potent cardiovascular activity. Can J Physiol Pharmacol. Jan. 1990;68(1):131-6.

Takei et al., A new natriuretic peptide isolated from cardiac atria of trout, *Oncorhynchus mykiss*. FEBS Lett. Sep. 8, 1997;414(2):377-80.

Adessi et al., Converting a peptide into a drug: strategies to improve stability and bioavailability. Curr Med Chem. May 2002;9(9):963-78. doi: 10.2174/0929867024606731.

Jennings et al., The disulfide bonded ring of iso-rANP, unlike that of rANP, has potent cardiovascular activity. Can J Physiol Pharmacol. Jan. 1990;68(1):131-6. doi: 10.1139/y90-020.

Betts et al., Amino acid properties and consequences of substitutions. Bioinformatics for Geneticists. Feb. 21, 2003. Chapter 14. Eds., Barnes et al. John Wiley & Sons, Ltd. 28 pages.

* cited by examiner

[Fig.1]
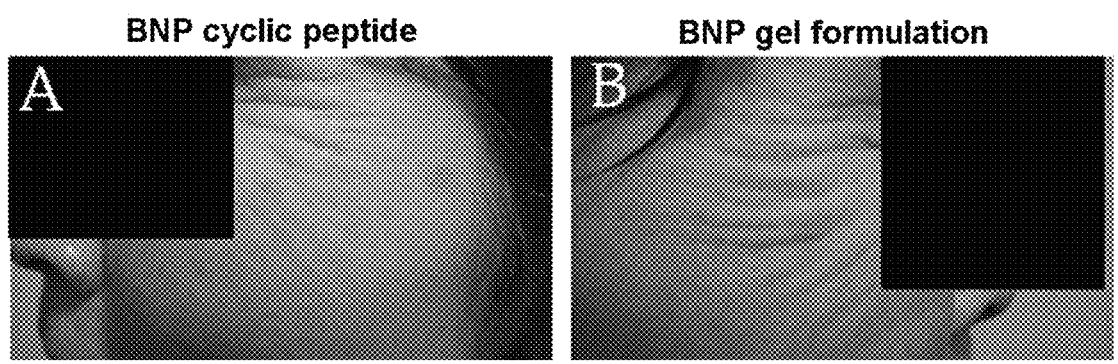
[Fig.2]
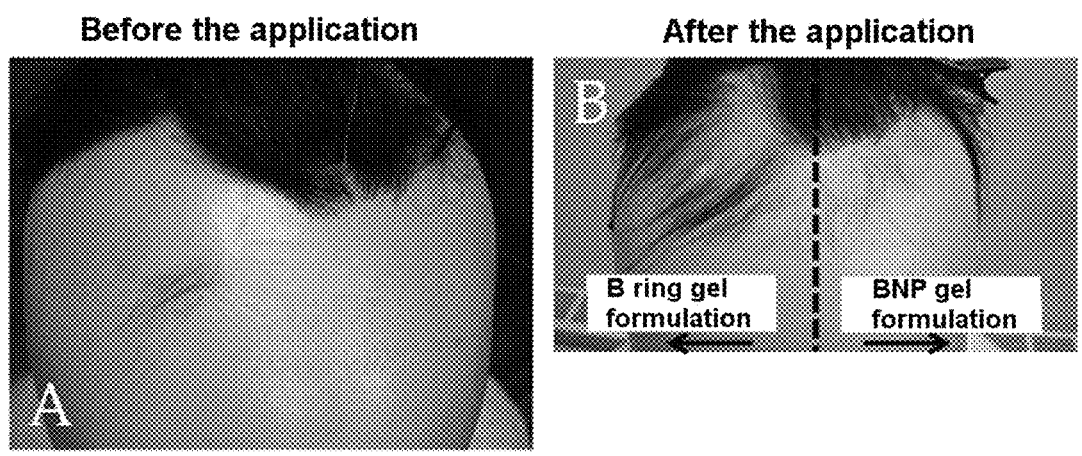

CYCLIC PEPTIDE AND A MEDICAMENT, EXTERNAL PREPARATION AND COSMETIC COMPRISING SAID CYCLIC PEPTIDE

RELATED APPLICATION

This application is a divisional of U.S. patent application Ser. No. 15/122,753, which is a national stage filing under 35 U.S.C. § 371 of International Application No. PCT/JP2016/065839, filed May 27, 2016, the entire contents of each of which are incorporated herein by reference in their entireties.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on May 22, 2020, is named I054170002US01-SUBSEQ-JRV and is 31 kilobytes in size.

TECHNICAL FIELD

The present invention relates to a cyclic peptide and a medicament, external preparation and cosmetic comprising said cyclic peptide.

BACKGROUND ARTS

BNP (brain natriuretic peptide) is a hormone which is synthesized and secreted in heart (predominantly in ventricles). BNP was isolated from and identified in pig brain in 1988, and it has been known since that BNP is secreted from ventricular myocardium of human, etc. An increase in cardiac stress or development of myocardial hypertrophy induces BNP secretion and increased in blood concentration. In general, BNP has activities such as diuretic activity, vasodilation, renin-aldosterone secretion suppressing action, sympatholytic activity, hypertrophy suppressing action. BNP is considered to a hormone which acts to protect the myocardium against damages caused by cardiac stress.

Amino acids constituting BNP differ slightly from species to species who produce BNP. Nevertheless it been revealed that its structure possesses a cyclic part and a tail part as a common structure (Non-Patent Literatures 1-2). For instance, wild-type human BNP has been known to consist 32 amino acid residues, and its fragments and derivatives are further proposed (Patent Literatures 1-6).

In Japan, BNP is currently not used as a therapeutic, but widely used in clinical practice as a biochemical marker for cardiac failure. In United States, however, it is used as a drug for alleviating symptoms of cardiac failure (trade name: Natrecor®). Recently, it has been proposed to utilize an external preparation comprising BNP for treating dermatitis, rhinitis, alopecia, etc., and also as a skin-improving agent (Patent Literature7-9).

PRIOR ART REFERENCES

Patent Literature

[Patent Literature1] JP A 2007-525213
[Patent Literature2] JP A 2008-509746
[Patent Literature3] WO 2008/032450
[Patent Literature4] U.S. Pat. No. 6,028,055
[Patent Literature5] U.S. Pat. No. 5,114,923
[Patent Literature6] U.S. Pat. No. 6,818,619
[Patent Literature7] WO 2011/010732
[Patent Literature8] WO 2011/024973
[Patent Literature9] WO 2012/099258

Non-Patent Literature

[Non-Patent Literature1] N. Akizukia, K. Kangawaa, N. Minaminob, H. Matsou, FEBS Letters 1991 280 (2): 357-362.
[Non-Patent Literature2] Takei Y, Fukuzawa A, Itahara Y, Watanabe T X, Yoshizawa Kumagaye K, Nakajima K, Yasuda A, Smith M P, Duff D W, Olson K R. FEBS Lett. 1997 Sep. 8; 414 (2):377-80.

SUMMARY OF THE INVENTION

Problems to be Solved by the Invention

As described above, BNP is considered to be a useful substance for the therapy of various diseases. However, in order to obtain a better therapeutic effect there is a need for developing a substance with a higher drug efficacy and stronger effect and a faster- and longer-acting substance.

An improvement in the duration and fast-acting properties of the drug efficacy and effect is quite meaningful in light of reducing required number/frequency of treatment, relieving the sufferings by the patient/user, and improving the quality of life (QOL) and the mental, physical, social or intellectual satisfaction in dairy living of the user. For example, dermatitis is often accompanied by symptoms such as an itch, infiltration or hot flush in the affected site; the sufferings by the patient will be reduced if these symptoms can quickly be alleviated. When an alopecia therapeutic, hair growing agent or hair growth stimulant is employed, the QOL of the user can be improved if the therapeutic effect, hair growth-stimulating or hair growing effect can be achieved immediately.

The inventors focused on these points and tried to search for a novel substance by reference to the structure of BNP.

Accordingly, the object of the present invention is to provide a novel peptide having a strong drug efficacy and effect, and a medicament or an external preparation comprising such peptide, specifically a prophylactic or therapeutic for dermatitis, rhinitis and alopecia, and a hair growth stimulant, a hair growing agent, an antipruritic, a cosmetic and a skin-care product, etc.

Means to Solve the Problems

It was previously considered that the tail part of the wild-type BNP peptide structure (which is composed of a cyclic part and tail part) plays at least certain important role in the binding and selectivity of BNP to its receptor. However, the inventors focused on the cyclic part of said structure, deleted the tail part, and made an intensive research on the resulting cyclic peptide. Accordingly we have obtained totally new findings including the effects of such cyclic peptide, its high drug efficacy, faster-acting and longer-lasting effect, and further continued the study and finally completed the invention.

Accordingly, the present invention relates to the followings:

[1] Acyclic peptide having an amino acid sequence expressed by Formula I:

(SEQ ID NO: 1)

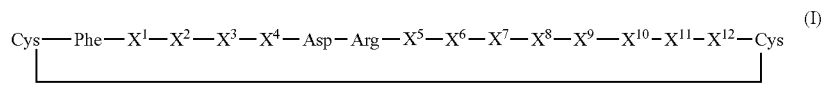
(I)

wherein,
- $X^1$ denotes Gly, Val, Ala, Ser or Thr,
- $X^2$ denotes Arg, Gln or His,
- $X^3$ denotes Lys or Arg,
- $X^4$ denotes Met, Leu or Ile,
- $X^5$ denotes Ile or Val,
- $X^6$ denotes Ser or Gly,
- $X^7$ denotes Ser or Ala,
- $X^8$ denotes Ser, Gln, Val, Ala, Thr, Leu, Ile or Met,
- $X^9$ denotes Ser, Val, Ala or Thr,
- $X^{10}$ denotes Gly or Arg,
- $X^{11}$ denotes Leu, Met, Ile, Val or Ala,
- $X^{12}$ denotes Gly, Ser or Ala, and
- the line connecting two Cys denotes a disulfide bond, and wherein the amino acid sequence does not have a peptide bond that is not between the amino acids constituting the amino acid sequence, or a derivative thereof or a pharmaceutically acceptable salt thereof.

[2] The cyclic peptide according to [1], wherein
- $X^2$ denotes Arg,
- $X^4$ denotes Met,
- $X^6$ denotes Ser,
- $X^7$ denotes Ser, and
- $X^{10}$ denotes Gly, or a derivative thereof or a pharmaceutically acceptable salt thereof.

[3] The cyclic peptide according to [1], wherein the amino acid sequence is selected from the amino acid sequences expressed by Formula (I-a)-Formula (I-e):

(SEQ ID NO: 3)

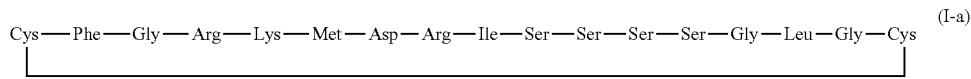
(I-a)

(SEQ ID NO: 4)

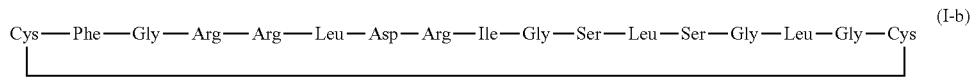
(I-b)

(SEQ ID NO: 5)

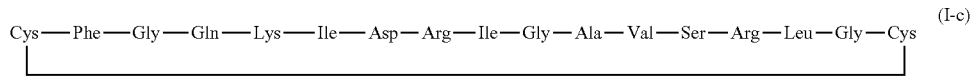
(I-c)

(SEQ ID NO: 6)

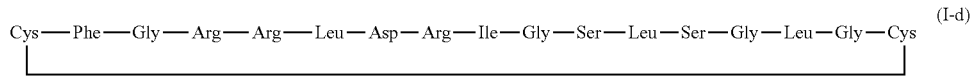
(I-d)

(SEQ ID NO: 7)

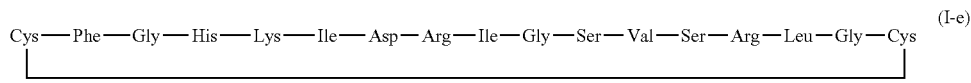
(I-e)

wherein, the line connecting two Cys denotes a disulfide bond, or a derivative thereof or a pharmaceutically acceptable salt thereof.

[4] The cyclic peptide according to any one of [1]-[3] or a derivative thereof or a pharmaceutically acceptable salt thereof, wherein the derivative is substituted by a substituent which is capable of replacing a hydrogen atom, hydroxyl group, carboxy group, amino group or imino group in the cyclic peptide.

[5] The cyclic peptide or a derivative thereof or a pharmaceutically acceptable salt thereof, which is formed by deleting 1 to 4 amino acids in the cyclic peptide expressed by any one of the Formulae (I-a)-(I-e) according to [3], or by replacing them with or adding them other amino acids, and which has an equal function with the cyclic peptide expressed by each of said formulae.

[6] An external preparation comprising one or more cyclic peptides according to any one of [1]-[5] and/or a derivative thereof and/or a pharmaceutically acceptable salt thereof.

[7] The external preparation according to [6], wherein the external preparation is an ingredient for a dermatitis therapeutic, dermatitis prophylactic, antipruritic, antiphlogistic, epidermis regeneration accelerating agent, wound epithelialization-accelerating agent or skin-care product.

[8] The external preparation according to [7], wherein the skin-care product is for moisturizing, and/or for preventing or improving rough skin, and/or for sebum/acne care, and/or for irritation alleviation/anti-inflammation, and/or for skin-lightening, and/or for anti-aging, and/or for preventing/alleviating ultraviolet lesion, and/or for slimming, and/or for skin-cleansing.

[9] The external preparation according to [6], wherein the external preparation is a bath agent, a body-cleansing agent or a hair-cleansing agent.

The external preparation according to [6], wherein the external preparation is an alopecia therapeutic, an alopecia prophylactic, a hair growing agent and/or a hair growth stimulant.

[11] The external preparation according to [6], wherein the external preparation is a rhinitis therapeutic and/or a rhinitis prophylactic.

[12] The external preparation according to [6], wherein the external preparation is a cosmetic.

[13] The external preparation according to any one of [6]-[12], wherein the formulation is a solid, semi-solid, powder, liquid, spray, ointment, cream, emulsion, gel or patch formulation.

[14] The external preparation according to any one of [6]-[13], wherein the external preparation is used as a pharmaceutical product, a quasi-drug or a cosmetic product.

[15] A use of the cyclic peptide according to any one of [1]-[4] and/or a derivative thereof and/or a pharmaceutically acceptable salt thereof for preparing the external preparation.

[16] A method of using the external preparation comprising applying the external preparation according to any one of [6]-[14] to the skin and/or mucosa of a subject.

[17] The method of using the external preparation according to [16], wherein the mucosa is labial, oral, nasal, ocular or vaginal mucosa.

[18] The method of using the external preparation according to [16], wherein the method is a method of treating and/or preventing dermatitis, a method of alleviating or resolving itch, a method of treating eczematous or other erosion or ulcer, or a method for skin-care.

[19] The method of using the external preparation according to [16], wherein the method is a method of treating and/or preventing alopecia, and/or a method of stimulating hair growth, and/or a method of growing hair.

[20] The method of using the external preparation according to [16], wherein the method is a method of treating and/or preventing rhinitis.

[21] A medicament comprising one or more cyclic peptides according to any one of [1]-[5] or a derivative thereof or a pharmaceutically acceptable salt thereof.

[22] The medicament according to [21], wherein the medicament is a therapeutic for hypertension, unstable angina, acute myocardial infarction, edematous diseases, renal failure, cardiac failure, immune diseases, obesity or metabolic syndrome.

The cyclic peptide described herein (hereinafter also referred to as "BNP cyclic peptide", "B ring" or "B ring-compound") is, as described above, derived from wild-type BNP. The wild-type BNP encompasses BNP from human, as well as BNPs from monkeys, pigs, birds and rats. Therefore, the B ring-compound also encompasses the B ring-compound from human, as well as those from monkeys, pigs, birds and rats.

Effect by the Invention

According to the present invention, novel cyclic peptides and compositions comprising the same can be provided. Such compositions are applied to an external preparation for preventing or treating dermatitis, rhinitis or alopecia, and further applied to a hair growth stimulant, a hair growing agent or an antipruritic, each of which are provided as a medicament, a quasi-drug, a skin-care product, or a cosmetic product. When an "external preparation" is referred alone in the present invention, it means an agent that is applied to skin or mucosa, whose utility is not limited to a medicament, quasi-drug, skin-care product and cosmetic product.

In general, the external preparation of the present invention has a significantly higher efficacy against dermatitis as compared to a conventional steroid external preparation, as well as an excellent immediate effect such that the symptoms start to be improved within three minutes in general. Its effect is great and long-lasting, and the amelioration period is long.

Furthermore, the external preparation of the present invention can, upon being applied onto the subject's skin or mucosa suffering a dermatitis, quickly relieve or eliminate perceptible symptoms that are or can be caused by dermatitis such as pruritus, soreness (pain), hot sensation, tautness, infiltration and erythema, improving the symptoms of the dermatitis.

Furthermore, the external preparation of the present invention exerts a moisturizing effect on the applied site, while exerting an effect to improve skin texture where the corneum layer is present at the applied site. It can thus exerts effects to improve skin texture, improves dry or rough skin, softens and moisturizes skin, reduce and diminish wrinkles, and improve roughened lip.

The external preparation of the present invention also has an effect of stimulating hair growth or promoting hair growth and at the same time preventing hair loss at the applied site when being applied to a decalvant site or a site where hair growth is stimulated. In this case, stimulated hairs tend to become terminal hairs and not white hairs. These effects are exhibited relatively quick as compared to other active agents that have previously been used in the therapeutics for alopecia, e.g., BNP, and the obtained effects are more significant.

Yet the external preparation of the present invention has an immediate, large and long-lasting effect effect on rhinitis with a long amelioration period.

Besides, since the cyclic peptide of the invention is a peptide sharing a part of its structure with BNP which is a hormone inherent in body, it causes little concern about side effects. It is also considered to have a small influence on homodynamics as long as used in an appropriate amount or used externally onto skin, etc. It therefore can be administered for prolonged period to a patient in need thereof, e.g., a patient with chronic dermatitis. Moreover, the external preparation of the invention causes no irritation when being taken externally and can be applied safely to a patient with sensitive skin, as well as to a child or woman, on face or neck, etc.

The reason why the cyclic peptide of the invention has a superior drug efficacy and effect as compared with wild-type BNP is not yet clear. However, according to our in silico analysis, it is suggested that the cyclic peptide of the invention is more easily and strongly bound to NPR-A receptor (GC-A) as compared with wild-type BNP. It is thus predicted that the cyclic peptide would have an excellent drug efficacy and effect, an excellent immediate effect in particular. As described above, B ring-compound is derived not only from human, but there also are B rings from animals of other species such as monkeys, pigs, birds and rat, and it has been confirmed that they have similar structures. From the results of the structural analysis described hereinbelow, it is strongly speculated that all these B rings exert similar effects as those of the B ring-compound from human.

BRIEF DESCRIPTION OF THE DRAWINGS

FIG. 1

A diagram showing the result of applying BNP cyclic peptide (A) or a gel formulation (B) on either left or right side of the face of a subject having large wrinkles on the face.

FIG. 2

A diagram showing the effect before and after the application of either B ring gel formulation or BNP gel formulation to a patient with female pattern alopecia and alopecia pityroides.

MODE FOR CARRYING OUT THE INVENTION

Hereinafter, the present invention is explained in detail based on its suitable embodiments.

1. The Cyclic Peptide, a Derivative Thereof and a Pharmaceutically Acceptable Salt Thereof Firstly, the cyclic peptide of the invention, a derivative thereof and a pharmaceutically acceptable salt thereof are explained.

The cyclic peptide of the present invention has an amino acid sequence expressed by Formula I:

(SEQ ID NO: 1)

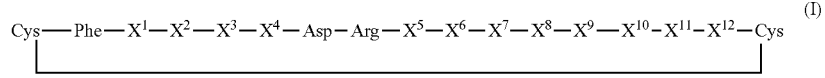

wherein,
  $X^1$ denotes Gly, Val, Ala, Ser or Thr,
  $X^2$ denotes Arg, Gln or His,
  $X^3$ denotes Lys or Arg,
  $X^4$ denotes Met, Leu or Ile,
  $X^5$ denotes Ile or Val,
  $X^6$ denotes Ser or Gly,
  $X^7$ denotes Ser or Ala,
  $X^8$ denotes Ser, Gln, Val, Ala, Thr, Leu, Ile or Met,
  $X^9$ denotes Ser, Val, Ala or Thr,
  $X^{10}$ denotes Gly or Arg,
  $X^{11}$ denotes Leu, Met, Ile, Val or Ala,
  $X^{12}$ denotes Gly, Ser or Ala,
  the line connecting two Cys denotes a disulfide bond, and wherein the amino acid sequence does not have a peptide bond that is not between the amino acids constituting the amino acid sequence.

Such cyclic peptide is, similar to previously known BNPs, considered to bind to a receptor NPR-A (also known as GC-A) having a guanylate cyclase domain and promote the production of cyclic guanosine monophosphate (cGMP), and has activities such as, for example, diuretic action, vasodilation, renin-aldosterone secretion suppressing action, sympatholytic activity and hypertrophy suppressing action. It has a superior drug efficacy and effect, particularly an excellent immediate effect, as compared to BNP.

In addition, as described hereinbelow, the above cyclic peptide can be used as an ingredient of an external preparation for a dermatitis therapeutic/prophylactic, a rhinitis therapeutic/prophylactic, an alopecia therapeutic/prophylactic, a hair growing agent, a hair growth stimulant, an antipruritic, etc., or as an ingredient of a skin-care product, a quasi-drug or a cosmetic product. The above cyclic peptide can also be used as an alternative for BNP in an medicament utilizing the activity of BNP as above, e.g., in an medicament for hypertension, unstable angina, acute myocardial infarction, edematous diseases, renal failure, cardiac failure, immune diseases, obesity or metabolic syndrome.

In another embodiment of the present invention, in the cyclic peptide of the invention, $X^1$—$X^{12}$ in the Formula (I) may be defined as one or more selected from the group consisting of following (1)-(12): (1) $X^1$ denotes Gly, Val, Ala, Ser or Thr,
  (2) $X^2$ denotes Arg, Gln or His,
  (3) $X^3$ denotes Lys or Arg,
  (4) $X^4$ denotes Met, Leu or Ile,
  (5) $X^5$ denotes Ile or Val,
  (6) $X^6$ denotes Ser or Gly,
  (7) $X^7$ denotes Ser or Ala,
  (8) $X^8$ denotes Ser, Gln, Val, Ala, Thr, Leu, Ile or Met,
  (9) $X^9$ denotes Ser, Val, Ala or Thr,
  (10) $X^{10}$ denotes Gly or Arg,
  (11) $X^{11}$ denotes Leu, Met, Ile, Val or Ala, and
  (12) $X^{12}$ denotes Gly, Ser or Ala.

A preferred cyclic peptide of the present invention is a cyclic peptide of Formula (I), wherein $X^2$ denotes Arg, $X^4$ denotes Met, $X^6$ denotes Ser, $X^7$ denotes Ser, and/or $X^{10}$ denotes Gly (SEQ ID NO: 2).

Furthermore, in another embodiment of the invention, in the cyclic peptide of the invention, the amino acid sequence expressed by Formula (I) may be selected from SEQ ID NOs: 3-8 and SEQ ID NOs: 16-75.

Furthermore, in the cyclic peptide of the invention, the amino acid sequence expressed by Formula (I) is preferably selected from the amino acid sequences expressed by the Formula (I-a)-Formula (I-e):

(SEQ ID NO: 3)

(I-a)

Cys-Phe-Gly-Arg-Lys-Met-Asp-Arg-Ile-Ser-Ser-Ser-Ser-Gly-Leu-Gly-Cys
|_____|

(SEQ ID NO: 4)

(I-b)

Cys-Phe-Gly-Arg-Arg-Leu-Asp-Arg-Ile-Gly-Ser-Leu-Ser-Gly-Leu-Gly-Cys
|_____|

(SEQ ID NO: 5)

(I-c)

Cys-Phe-Gly-Gln-Lys-Ile-Asp-Arg-Ile-Gly-Ala-Val-Ser-Arg-Leu-Gly-Cys
|_____|

(SEQ ID NO: 6)

(I-d)

Cys-Phe-Gly-Arg-Arg-Leu-Asp-Arg-Ile-Gly-Ser-Leu-Ser-Gly-Leu-Gly-Cys
|_____|

(SEQ ID NO: 7)

(I-e)

Cys-Phe-Gly-His-Lys-Ile-Asp-Arg-Ile-Gly-Ser-Val-Ser-Arg-Leu-Gly-Cys
|_____| wherein, the line connecting two Cys denotes a disulfide bond.

Each of the amino acid sequences expressed by these Formulae (I-a)-(I-e) is the cyclic part of human BNP (Formula (I-a)), swine BNP (Formula (I-b)), rat BNP (Formula (I-c)), rabbit BNP (Formula (I-d)) and murine BNP (Formula (I-e)), respectively. Therefore, the cyclic peptide having such an amino acid sequence will exhibit the aforementioned effects with more certainty. Because swine BNP cyclic peptide is consistent with those of avian (SEQ ID NO: 8, Cys-Phe-Gly-Arg-Arg-Ile-Asp-Arg-Ile-Gly-Ser-Leu-Ser-Gly-Met-Gly-Cys, wherein, 1st Cys and 17th Cys form a disulfide bond), bovine (SEQ ID NO: 9, Cys-Phe-Gly-Arg-Arg-Leu-Asp-Arg-Ile-Gly-Ser-Leu-Ser-Gly-Leu-Gly-Cys, wherein, 1st Cys and 17th Cys form a disulfide bond), feline (SEQ ID NO: 10, Cys-Phe-Gly-Arg-Arg-Leu-Asp-Arg-Ile-Gly-Ser-Leu-Ser-Gly-Leu-Gly-Cys, wherein, 1st Cys and 17th Cys form a disulfide bond), canine (SEQ ID NO: 11, Cys-Phe-Gly-Arg-Arg-Leu-Asp-Arg-Ile-Gly-Ser-Leu-Ser-Gly-Leu-Gly-Cys, wherein, 1st Cys and 17th Cys form a disulfide bond), and ovine (SEQ ID NO: 12, Cys-Phe-Gly-Arg-Arg-Leu-Asp-Arg-Ile-Gly-Ser-Leu-Ser-Gly-Leu-Gly-Cys, wherein, 1st Cys and 17th Cys form a disulfide bond), BNP cyclic peptides derived from these organisms also have similar effects as the cyclic peptide of the present invention. Among those mentioned above, it is particularly preferred that the amino acid sequence expressed by Formula (I) is the amino acid sequence expressed by Formula (I-a). In another embodiment of the invention, the cyclic peptide may be expressed by SEQ ID NOs: 16-75.

The cyclic peptide of the present invention encompasses a derivatized form of said cyclic peptide. Such a derivative can be used as such, as an active substance, or also used as a prodrug.

A derivative of the present invention can be obtained by adding (modifying) a known substituent to certain group of an amino acid in the cyclic peptide such as, for example, a hydrogen atom, hydroxyl group, carboxy group, amino group or imino group, or replacing it with a known replaceable substituent. Modification include, but not limited to, chemical modifications such as, for example, glycosylation, acetylation, phosphorylation and lipidation, to an amino acid within the cyclic peptide.

The addition (modification) or replacement of an amino acid within the cyclic peptide can occur in one group, or can occur in more than one group at the same time. Any known substituents can be used as long as being capable of replacing above groups and it goes without saying that such substituents naturally include, for example, protecting groups such as BOC.

The cyclic peptide of the invention further includes a mutated form of said cyclic peptide. Namely, a mutant of the present invention can be obtained by deleting an amino acid in the cyclic peptide, replacing it with or adding it another amino acid. The number of amino acid to be deleted, replaced with other amino acids or added is 4 or less, more preferably 3 or less, even more preferably 2 or less, and particularly preferable 1 or less. It also goes without saying that the deletion, replacement or addition of amino acids in the cyclic peptide may occur concurrently and independently to each other.

An amino acid that is capable of being replaced with another amino acid can be, in the case of human BNP (Formula (I-a)), exemplified as follows, without being limited thereto. The third amino acid from left, Gly, may be replaced with either Val, Ala, Ser or Thr. The forth amino acid from left, Arg, may be replaced with either Gln or His. The fifth amino acid from left, Lys, may be replaced with Arg. The sixth amino acid from left, amino acid, Met, may be replaced with either Leu or Ile. The ninth amino acid from left, Ile, may be replaced with Val. The twelfth amino acid from left, Ser, may be replaced with either Gln, Val, Ala, Thr, Leu, Ile or Met. The thirteenth amino acid from left, Ser, may be replaced with either Val, Ala or Thr. The fourteenth amino acid from left, Gly, may be replaced with Arg. The fifteenth amino acid from left, Leu, may be replaced with either Met, Ile, Val or Ala. The sixteenth amino acid from left, Gly, may be replaced with either Ser or Ala. Table 32 summarizes examples of replaceable amino acids in the cyclic peptide of the invention, though the invention will not be limited thereto.

Cyclic peptides in which one amino acid has been replaced include such as, for example, SEQ ID NOs: 16-44, though the invention will not be limited thereto. Cyclic peptides in which two amino acids have been replaced include such as, for example, SEQ ID NO: 45-58, though the invention will not be limited thereto. Yet cyclic peptides in which three amino acids have been replaced include such as, for example, SEQ ID NOs: 59-70, though the invention will not be limited thereto. Furthermore, cyclic peptides in which four amino acids have been replaced include such as, for example, SEQ ID NOs: 71-75, though the invention will not be limited thereto. It also goes without saying that five or more amino acids can be replaced by appropriately combining the aforementioned amino acid.

Deletion of one to several amino acids can take place in similar manner to the replacement of the aforementioned amino acids.

The number of amino acid which are to be deleted or replaced with other amino acids or added may be determined such that the cyclic peptide will have 80% homology, preferably 90% homology to the cyclic peptide of the invention.

In addition, the present invention may be a mutant as described above, and a derivative thereof. As long as it retains the effect of the invention, any mutant or a derivative thereof is encompassed in the cyclic peptide according to the invention. In another embodiment, it has at least a BNP activity. For purpose of improving the activity of the cyclic peptide of the invention, prolonging the effect of the invention, and/or increasing storage stability of the cyclic peptide of the invention, the cyclic peptide of the invention or the amino acids constituting said peptide may be altered in an appropriate manner. For example, an amino acid in the cyclic peptide of the invention may be chemically modified, some amino acids constituting the cyclic peptide may be deleted or replaced with other amino acids, and/or new amino acids may be added.

For example, the C-terminal group —COOH of one Cys of the cyclic peptide may be replaced with —COOR$^1$, —CONHR$^1$ or —CONR$^{12}$, and/or the N-terminal group NH$_2$ of the other Cys of the cyclic peptide may be replaced with —NHC(O)R$^1$ or —N(C(O)R$^1$)$_2$. Here, each appearance of R$^1$ is independently a branched or straight hydrocarbon group or an alkylene glycol chain or sugar chain having 1 to 20 carbon atoms. The number of carbon atoms in R$^1$ is preferably 1 to 10, more preferably 1 to 5, yet more preferably 1 to 2.

Pharmaceutically acceptable salts include, without being particularly limited, as the cyclic peptide of the invention or a derivative, such as for example, a salt with an inorganic base, a salt formed with an organic base, a salt formed with an inorganic acid, a salt formed with an organic acid, a salt formed with a basic or acidic amino acid. Examples of suitable salt formed with inorganic base include such as, for example, an alkaline metal salt such as a sodium salt and potassium salt; an alkaline earth meal salt such as a calcium salt and magnesium salt; and an aluminum salt and ammonium salt. Examples of suitable salt formed with organic base include such as, for example, a salt with an alkyl amine such as trimethyl amine or triethyl amine; a salt formed with a heterocyclic amine such as pyridine and picoline; a salt formed with an alkanol amine such as ethanol amine, diethanol amine and triethanol amine; a salt formed with a cycloalkyl amine such as cyclohexyl amine and dicyclohexyl amine; a salt formed with an alkylene diamine derivative such as N,N'-dibenzylethylenediamine. Examples of suitable salt formed with inorganic acid include such as, for example, a salt formed with hydrochloric acid, hydrobromic acid, nitric acid, sulfuric acid or phosphoric acid. Examples of suitable salt formed with organic acid include such as, for example, a salt formed with a monocarboxylic acid such as formic acid, acetic acid, trifluoroacetic acid and propionic acid; a salt formed with a polyvalent carboxylic acid such as fumaric acid, oxalic acid and maleic acid; a salt formed with a oxycarboxylic acid such as tartaric acid, citric acid, succinic acid and malic acid; a salt formed with a sulfonic acid such as methane sulfonic acid, benzezne sulfonic acid and p-toluene sulfonic acid; and a salt formed with benzoic acid. Examples of suitable salt formed with a neutral amino acid include such as, for example, a salt formed with glycine, valine or leucine; examples of suitable salt formed with a basic amino acid include such as, for example, a salt formed with arginine, lysine or ornithine; and examples of suitable salt formed with an acidic amino acid include such as, for example, a salt formed with aspartic acid acid or glutamic acid.

Among those mentioned above, a cyclic peptide composed of the amino acid sequence expressed by Formula (I) or a pharmaceutically acceptable salt is preferred. Namely, it is preferred that the amino acid sequence expressed by Formula (I) is not replaced.

A method for producing the cyclic peptide of the present invention, a derivative and pharmaceutically acceptable salt thereof may employ, without being particularly limited, for example, any known chemical synthetic or genetic engineering methods.

When the amino acid sequence as above is chemically synthesized, it may be synthesized by any chemical synthetic method, or any known method for peptide synthesis, for example, or solid-phase or liquid-phase synthetic method. Moreover, any commercial synthesizer (e.g., SHIMADZU Corporation: PSSM-8) may be used for synthesis.

A disulfide bond can be formed in the amino acid sequence, for example, by DMSO oxidation method or iodine oxidation method without being particularly limited. In this case, an intramolecular disulfide bond can be formed by treating a free sulfhydryl group or a sulfhydryl group protected by a protecting group with either DMSO or iodine (12) to result in said cyclic peptide.

A protecting group includes such as, for example, 4-methylbenzyl group (Bzl (4Me)), trityl group (Trt), tert-butyl group, N-(acetyl) aminomethyl group (Acm). Deprotection can be carried out through appropriate treatment corresponding to these protecting group, for example, for 4-methylbenzyl group by treating with a strong acid, and for N-(acetyl) aminomethyl group by treating with iodine.

Next, if necessary, the cyclic peptide is derivatized to result in a derivative. Derivatization can be carried out by known method. Alternatively, a derivative of the cyclic peptide can be produced at the time of peptide synthesis by introducing in advance a substituent into the amino acid constituting the cyclic peptide.

Then, if necessary, a pharmaceutically acceptable salt is produced by ion exchange of the cyclic peptide or derivative thereof. Ion exchange can be carried out, for example, by bringing into the contact the cyclic peptide or derivative thereof with a desired acid or base.

On the other hand, when the peptide is synthesized by genetic engineering, it can be synthesized by any known method such as, for example, methods described in Sambrook J. et al., Molecular Cloning, A Laboratory Manual (4th edition) (Cold Spring Harbor Laboratory Press (2012)). For instance, a DNA fragment coding for the amino acid sequence expressed by Formula (I) is prepared at first. Preparation of the DNA fragment can be performed, for example, if it is a case in which the DNA fragment codes for the amino acid sequence expressed by Formula (I-a), by amplifying the DNA fragment by PCR using a vector comprising a full-length human BNP gene as template and primers designed to synthesize a defined DNA region. Alternatively, a DNA fragment can be chemically synthesized.

Then, the amplified DNA fragment is ligated into an appropriate vector to obtain a recombinant vector for protein expression. Next, the vector for protein expression is allowed to be taken up by target cells and the transformed cells are selected. Finally, the protein produced by the cells (i.e., the protein composed of the amino acid sequence expressed by Formula (I)) is collected.

Formation of disulfide bond, derivatization and salt formation in the collected protein can be carried out as described above.

The identification of the compound of interest such as a cyclic peptide can be confirmed by known procedures such as, for example, reverse-phase HPLC or mass spectroscopy.

The presence or absence of BNP activity in the obtained compound can readily be confirmed by known means. For instance, it can be confirmed by examining cGMP producing activity in NPR-A receptor-expressing cells.

2. External Preparation

Secondly, the external preparation of the present invention is explained.

The external preparation of the present invention comprises one or more cyclic peptide and/or a derivative thereof and/or a pharmaceutically acceptable salt thereof as described above. If two or more cyclic peptides are used, the number of different cyclic peptide to be mixed is not limited, though 2 to 3 are preferred in terms of preparation cost and convenience. It includes SEQ ID NO: 19, 29, 33, 36, 39 and 43, for example, but the invention is not limited to these and these cyclic peptide can appropriately be combined as long as it does not interfere the effect of the invention.

2.1 Application

The external preparation of the present invention can be used for following uses, for example, without being particularly limited, and in each case exerts remarkable effect which had not previously been achieved. The external preparation of the present invention is not limited to any particular use, and can be used as a pharmaceutical product, a quasi-drug and/or a cosmetic product depending on its drug efficacy and effect.

Hereinbelow, the invention will be described in detail for each of its use.

(1) Therapeutic/Prophylactic for Dermatitis

The external preparation of the present invention can be a therapeutic and/or prophylactic for dermatitis.

The external preparation of the present invention can, upon being applied onto the subject's skin or mucosa suffering dermatitis, quickly relieve or eliminate various perceptible symptoms and conditions that are or can be caused by dermatitis such as pruritus, soreness (pain), hot sensation, tautness, erythema, infiltration, papule, lichenification, crust, exudation or skin desiccation, improving the symptoms of dermatitis. In addition, the external preparation of the present invention does not cause any irritation at the site of application.

Furthermore, such action of the external preparation comprising the cyclic peptide of the invention is effected more quickly and for prolonged time period as compared to that of an external preparation comprising BNP having the tail part. Although reasons for these advantageous effects of the cyclic peptide over such BNP are not clear, the cyclic peptide of the invention is considered to have an advantageous structure for binding to its receptor (NPR-A receptor) over BNP, thereby enabling faster binding to the NPR-A receptor in the vicinity of the affected site and at the same time prolonging its binding time. Moreover, it is considered that its relatively quick binding to the NPR-A receptor near the affected site can prevents the cyclic peptide from diffusing out of the affected site via bloodstream, etc., enabling it to stay around the affected site for relatively long time.

The external preparation of the present invention does not only suppress or prevent inflammation in dermatitis but also acts to restore and/or retain the barrier function of skin.

Here, skin's barrier function works for protecting skin against entry of stimuli and saprophytes from external environment or for retaining moisture. The external preparation restores the barrier function, and thus able to prevent the progress or exacerbation of inflammation. The barrier function of skin is greatly affected by the alignment state of corneocytes in the corneum, i.e., state of skin texture and moisturization. The external preparation of the present invention acts to improve skin texture and to moisturize skin. Therefore, its effects of restoring and maintaining skin barrier function are also obvious.

The external preparation of the present invention is also effective on skin symptoms commonly called acne, i.e., such as comedones, red papule, pustula, cysts/tuberosity.

Moreover, a quick relief or elimination of perceptible symptoms or conditions will reduce the burden of the subject (patient) and improve the QOL of the patient, while preventing the patient from being bothered by itch or soreness and from acting to damage the affected site, for example, touching or scratching. This effect of the external preparation of the present invention to relieve or eliminate perceptible symptoms or conditions is, in general, exhibited within 10 minutes, preferably within 5 minutes, more preferably within 3 minutes after application.

In addition, the external preparation of the present invention can treat dermatitis in which steroid dermatosis has been developed, or dermatitis that is intractable by other common drugs for dermatitis therapy such as steroid and tacrolimus, for example dermatitis for which a sufficient therapeutic effect cannot be achieved by these formulations, or dermatitis which is resistant to these formulations, or dermatitis for which the use of these formulations is not suitable or desirable. Conventional widely-used steroid external preparations have significant problems upon terminating application that the severity returns to the pre-application level and that a rebound phenomenon may occur and exacerbate the condition. The external preparation of the present invention has no such problems as a rebound phenomenon.

Dermatitis is in general a disease which causes inflammation in skin or mucosa. Dermatitis is normally accompanied with one or more symptoms selected from acute eczema symptoms such as erythema, infiltrative erythema, papule, vesicle, pustula, infiltration, incrustation and desquamation; chronic eczema symptoms such as lichenification and pigmentation; and scales, crust (scab) attachment, scratching, scratch scar, prurigo nodularis, erosion, edema, oozing and squamatization.

Dermatitis herein is not particularly limited as long as it is a disease which is accompanied with inflammation in skin or mucosa and includes such as, for example, eczema and atopic dermatitis such as chronic eczema, dyshidrotic eczema, infantile xerotic eczema; contact dermatitis such as allergic contact dermatitis and primary irritant contact dermatitis; seborrheic dermatitis; asteatotic dermatitis; autosensitization dermatitis; stasis dermatitis; urticaria such as allergic urticaria (e.g., alimentary urticaria and drug-induced urticaria) and nonallergic urticaria (e.g., physical urticaria, solar urticaria and cholinergic urticaria); insect bite; drug eruption; psoriasis such as plaque psoriasis, guttate psoriasis, erythrodermic psoriasis, pustular psoriasis and psoriasis arthropathica; prurigo such as chronic prurigo, acute prurigo, gestational prurigo and nodular prurigo; rosacea; rosacea-like dermatitis; cutaneous vasculitis such as cutaneous allergic vasculitis; cutaneous pruritus such as systemic cutaneous pruritus, localized cutaneous pruritus, senile cutaneous pruritus and gestational pruritus; solar dermatitis; erythrosis; nummular dermatitis; localized scratching dermatitis; perioral dermatitis; pompholyx; keratosis pilaris; lichen planus, dyshidrotic eczema, dyshidrosis, miliaria and acne vulgarisacne vulgaris. The external preparation of the present invention can be applied to the therapy and prophylaxis of any of these diseases.

The external preparation of the present invention exerts an excellent effect especially on eczema, atopic dermatitis, contact dermatitis, seborrheic dermatitis, insect bite, allergic or nonallergic urticaria and psoriasis, preferably on eczema, atopic dermatitis, contact dermatitis and insect bite, more preferably on eczema and atopic dermatitis. Therefore, the external preparation of the present invention can be used for the purpose of the therapy and prophylaxis of at least one or more dermatitis selected from above-mentioned group.

(2) Ingredients of Cosmetic or Skin-Care Product

The external preparation of the present invention may be an ingredient for a cosmetic or skin-care product.

The external preparation of the present invention will, upon being applied to skin and/or mucosa, provide moisture to the applied site and exert moisturizing effect, preventing skin from dryness and roughness. In cases where corneum is present at the site of application, it exerts an effect of improving skin texture there. It also provides and retains moderate elasticity and flexibility of skin and mucosa, softens skin, gives skin and mucosa resilience and firmness. Moreover, it improves wrinkles (including fine and large wrinkles) and flabbiness at the applied site, and further diminishes the appearance of dullness and spots. By diminishing dullness and spots away, it consequently provides a skin-lightening effect.

As a result, the external preparation of the present invention can be used for the purpose of maintaining or improving skin and/or mucosal condition, without being particularly limited, for example, for obtaining at least one effects selected from a group consisting of preventing or improving dry skin, skin roughness, sensitive skin, roughened lips and appearance of large and fine wrinkles, maintaining skin or mucosal condition, anti-aging, and skin-lightening, or obtaining for at least one effects selected from the above effects.

Skin roughness herein includes miliaria, chilblain, cracked skin, chapped skin, acne, diaper rashes, festering, chafed inner thighs and razor burns.

Specific utilities of the external preparation of the present invention as an ingredient for the cosmetic or skin-care product includes, without being particularly limited, for example, cosmetics for make-up such as face lotion, emulsion, serum, cream, cold cream, gel, mask, pack, powder, hand soap, perfume, deodorant, as well as foundation, face powder, eye shadow, eyeliner, mascara, eyebrow, blush, makeup base, lip stick, lip cream and nail polish, and furthermore cosmetics for hair such as shampoo, rinse, conditioner, hair color, hair tonic, styling agent and perm chemical, body cleansers such as face wash, cleansing and body soap, skin-care products such as body powder, after-shave lotion and pre-shave lotion, and bath agents.

The above effects of the external preparation of the present invention are quickly exhibited, within 10 minutes in general, preferably within 5 minutes, more preferably within 3 minutes after application depending on the type of the effect.

The above effects of the external preparation of the present invention last for relatively long time. In general, the effect lasts for 4 hours or more, preferably, 8 hours or more, more preferably 24 hours or more after it started to effect depending on the type of the effect.

(3) Antipruritic

The external preparation of the present invention can be an antipruritic.

As mentioned above, the external preparation of the present invention is suitable for using as antipruritic because it quickly exerts an excellent antipruritic effect at the applied site when being applied to skin or mucosa.

The antipruritic effect of the external preparation of the present invention as mentioned above is exhibited within 10 minutes in general, preferably within 5 minutes, more preferably within 3 minutes after application.

(4) Alopecia Therapeutic, Alopecia Prophylactic, Hair Growing Agent and Hair Growth Stimulant The external preparation of the present invention can also be an alopecia therapeutic, alopecia prophylactic, hair growing agent and/or hair growth stimulant.

When the external preparation of the present invention is applied to a site of hair loss or a site where hair growth is to be stimulated, it acts to prevent hair loss and promote hair growth stimulation and hair growing at the applied site. It has effects such as nourishing hair, promoting hair growth, and improving or preventing hair thinning at the applied site. In this case, hairs to be stimulated to grow tend to become terminal hairs or hairs which are not white hairs. These effects are exhibited in relatively early stage as compared to other active ingredients previously used in alopecia therapeutics e.g., BNP, and the effects obtained are significant.

The external preparation of the present invention also has an improving or preventing effect on dermatitis as mentioned above. Therefore, it can improve or prevent skin inflammation associated with alopecia. Such effects are particularly advantageous when alopecia has been exacerbated due to skin condition of the site of application (such as scalp).

Moreover, the external preparation of the present invention exerts moisturizing and skin texture-improving effects at the applied site when being applied to skin as mentioned above. It can remove and suppress dandruff and itching, while giving moisture to hair and scalp, improving and preventing dryness and keeping hair and scalp healthy. It also can improve seborrhea.

The external preparation of the present invention also acts to alleviate or eliminate the perceptible symptoms or conditions as mentioned above, thereby reducing the burden of the subject (patient) and improving QOL of the patient. Moreover, it can prevent the patient from being bothered by itch or soreness and acting to damage the affected site, for example, touching or scratching, thereby preventing exacerbation of skin condition which may induce alopecia.

When the external preparation of the present invention is used as alopecia therapeutic or prophylactic, applicable alopecia includes such as, for example, alopecia as listed below, without being particularly limited. The external preparation can be used for the purpose of treating or preventing one ore more of these alopecia.

(Acquired Alopecia)

(i) Alopecia without accompanying scarring or skin lesion (alopecia areata, male pattern alopecia, seborrheic alopecia, alopecia pityroides, female pattern alopecia, gestational alopecia, malignant alopecia, senile alopecia, alopecia totalis, alopecia areata *multilocularis*, ophiasis, drug-induced alopecia, cancer chemotherapy-induced alopecia and radiation exposure-induced alopecia, traumatic/mechanical alopecia, malnutrition/metabolic disorder associated alopecia, endocrine dysfunction associated alopecia and telogen effluvium (post partum alopecia, alopecia after high fever)).

(ii) Alopecia observed on skin lesion or pathologic skin (infection-induced alopecia, tumor-induced alopecia, inflammation-induced alopecia)
(iii) Scarring alopecia (skin infection-induced alopecia, alopecia induced by infiltration of inflammatory cells)
(Congenital Alopecia)

Diffuse alopecia, congenital atrichia, alopecia in hereditary syndromes, localized alopecia, phakomatosis, aplasia cutis, congenital alopecia *triangularis*.

Among those mentioned above, the external preparation of the present invention exerts an excellent effect particularly on acquired alopecia, preferably on alopecia without accompanying scarring or skin lesion, more preferably on alopecia areata, male pattern alopecia, seborrheic alopecia, alopecia pityroides, female pattern alopecia, gestational alopecia, malignant alopecia, senile alopecia, alopecia totalis, alopecia areata *multilocularis*, ophiasis, drug-induced alopecia, cancer chemotherapy-induced alopecia and radiation exposure-induced alopecia, traumatic/mechanical alopecia, malnutrition/metabolic disorder associated alopecia, endocrine dysfunction associated alopecia and telogen effluvium. Therefore, the external preparation of the present invention can be used for the purpose of treating or preventing at least one or more alopecia selected from the above-mentioned group.

(5) Rhinitis Therapeutic and/or Prophylactic

The external preparation of the present invention can also be a rhinitis therapeutic and/or prophylactic.

Rhinitis is a disease caused by mucosal inflammation in nasal cavity and/or paranasal cavity and induces main symptoms such as nasal obstruction, rhinorrhea, sudden recurrent sneezing, as well as symptoms such as pruritus. In the present invention, "rhinitis" does not only includes rhinitis in a narrow definition which are accompanied with mucosal inflammation in nasal cavity, but also includes sinusitis accompanied with mucosal inflammation in paranasal cavity.

The external preparation of the present invention can improve or prevent various symptoms associated with rhinitis such as nasal obstruction, rhinorrhea, sneezing and pruritus, when being applied to nasal cavity mucosa and/or paranasal cavity mucosa. Especially these effects are exhibited quickly and last for a prolonged time as compared to a rhinitis therapeutic comprising BNP having the tail part.

Such effects of the external preparation of the present invention on rhinitis are exhibited within 8 minutes in general, preferably within 5 minutes, more preferably within 3 minutes after its application.

Also the effect of the external preparation of the present invention on rhinitis as described above lasts for 4 hours or more in general, preferably for 8 hours or more, more preferably for 24 hours or more after it started to effect.

When the external preparation of the present invention is used as a rhinitis therapeutic and/or prophylactic, applicable rhinitis includes such as, without being particularly limited, for example, infectious rhinitis including acute rhinitis and chronic rhinitis; hypersensitive non-infectious rhinitis including combined (flower hypersensitivity) rhinitis, rhinitis with rhinorrhea, congestive rhinitis, edematous rhinitis and dry-nose type rhinitis; irritant-induced rhinitis including physical rhinitis, chemical rhinitis and radiation rhinitis; and atrophic rhinitis and idiopathic granulomatous rhinitis; and sinusitis such as acute sinusitis, chronic sinusitis (maxillary empyema), eosinophilic sinusitis and paranasal cavity mycosis, The external preparation can be used for the purpose of treating or preventing one ore more of the above.

Combined rhinitis includes, for example, allergic rhinitis including perennial allergic rhinitis and seasonal allergic rhinitis, and nonallergic rhinitis including vasomotor (essential) rhinitis and eosinophilic rhinitis.

Rhinitis with rhinorrhea includes, for example, gustatory rhinitis, cold air-induced rhinitis and senile rhinitis.

Congestive rhinitis includes, for example, drug-induced rhinitis, psychogenic rhinitis, gestational rhinitis, endocrine rhinitis and cold rhinitis.

Edematous rhinitis includes, for example, aspirin-hypersensitive rhinitis.

Among those mentioned above, the external preparation of the present invention exerts an excellent effect particularly on hypersensitive non-infectious rhinitis, irritant-induced rhinitis and sinusitis, preferably on hypersensitive non-infectious rhinitis and chronic sinusitis, more preferably on combined (flower hypersensitivity) rhinitis, rhinitis with rhinorrhea, congestive rhinitis, edematous rhinitis and dry-nose type rhinitis, chronic sinusitis. Therefore, the external preparation of the present invention can be used for the purpose of treating or preventing at least one or more rhinitis selected from the above-mentioned group.

In terms of symptoms, since the external preparation of the present invention acts as described above, it can be used for any of rhinitis with sneezing/rhinorrhea, rhinitis with nasal obstruction and rhinitis with both symptoms.

In addition, the external preparation of the present invention exhibits an effect of improving rhinitis which cannot be cured by a rhinitis therapeutic that has conventionally been used such as steroid drug.

(6) Other External Preparations

The external preparation of the present invention can also be used for an application other than those described above for the effect of the cyclic peptide as described above. In this case, the external preparation of the present invention can set an objective that is not the effects of the cyclic peptide as described above. In this case, the cyclic peptide of the invention, a derivative and/or a pharmaceutically acceptable salt thereof is used for the purpose of assisting the main effect of the external preparation or adding another effect to the main effect.

Such application include such as, without being particularly limited, for example, body powder, deodorant, depilation agent, soap, body shampoo, bath agent, hand soap, perfume, sunscreen, and antiinflammatory agent and antifungal agent.

2.2 Formulation

The external preparation of the present invention can exert the effect of its active ingredient, i.e., the cyclic peptide or a derivative and/or pharmaceutically acceptable salt thereof, certainly and quickly in the vicinity of the applied site by being locally applied to the site of the interest (e.g., affected site) on skin or mucosa.

Such external preparation can be, without being particularly limited, for example, an agent for integument, eye drop, ear drop, nasal drop, buccal agent or suppository. Among these, when the external preparation of the present invention is a dermatitis therapeutic, a dermatitis prophylactic, an antipruritic, a skin-care product, an alopecia therapeutic, an alopecia prophylactic, a hair growing agent or a hair growth stimulant, it is preferably an agent for integument. On the other hand, when the external preparation of the present invention is a rhinitis therapeutic and/or prophylactic, it is preferably a nasal drop. Furthermore, when it is a therapeutic/prophylactic of a corneal disease, it is preferably an eye drop.

When the external preparation of the present invention is an agent for integument, it can be, without being particularly limited, for example, an external solid formulation, an external liquid formulation, a spray formulation, an ointment, an emulsion, a cream, a gel formulation or a patch.

An external solid formulation is a solid formulation for applying or spraying onto such as skin. Such an external solid formulation includes, for example, a powder form external formulation.

An external liquid formulation is a liquid formulation for applying onto such as skin. Such an external liquid formulation includes, for example, a lotion and liniment.

A spray formulation is a formulation for spraying an active ingredient in a mist, powder, foam or paste form onto skin. Such spray formulation includes, for example, an external aerosol and a pump spray formulation.

An ointment is a semi-solid formulation which is applied to skin and comprises an active ingredient dissolved or dispersed in a base. The ointment can also be a lip cream for locally applying to lips, etc.

A cream is a semi-solid formulation which is applied to skin and emulsified as either oil-in-water or water-in-oil type.

A gel formulation is a gelled formulation which is applied to skin. The gel formulation includes, for example, aqueous gel formulation and oil-based gel formulation.

A patch is a formulation which is attached to skin. The patch includes, for example, a tape or plaster.

A nasal drop is a formulation which is administered to nasal cavity or nasal mucosa. The nasal drop includes, for example, nasal powder formulation and a nasal drop. Among these, nasal drop is preferred.

In any formulation described above, the external preparation of the present invention comprises the cyclic peptide of the present invention and/or a derivative thereof and/or a pharmaceutically acceptable salt thereof as described above.

When the formulation is an external liquid formulation, an ointment, a cream or a gel formulation, the external preparation of the present invention comprises the cyclic peptide and/or a derivative thereof and/or a pharmaceutically acceptable salt thereof at a concentration of, for example, 0.0001 to 1000000 µg/g, preferably 0.001 to 10000 µg/g, more preferably 0.01 to 1000 µg/g, yet more preferably 0.1 to 100 pig/g. In another embodiment, it may comprises the cyclic peptide at a concentration of 1 to 800 µg/g or 3 to 500 µg/g.

When the formulation is a spray formulation, the external preparation of the present invention comprises in the stock solution of the spray formulation the cyclic peptide and/or a derivative thereof and/or a pharmaceutically acceptable salt thereof at a concentration of, for example, 0.0001 to 1000000 µg/mL, preferably 0.001 to 10000 µg/mL, 0.01 to 1000 µg/mL, more preferably 0.1 to 100 µg/mL, yet more preferably 1 to 100 µg/mL. In another embodiment, it may comprises the cyclic peptide at a concentration of 1 to 800 µg/mL or 3 to 500 µg/mL.

When the formulation is a patch, the external preparation of the present invention comprises the cyclic peptide and/or a derivative thereof and/or a pharmaceutically acceptable salt thereof at a concentration of, for example, 0.0001 to 1000000 µg/mL, preferably 0.001 to 10000 µg/mL, more preferably 0.01 to 1000 µg/mL, yet more preferably 0.1 to 100 µg/mL, particularly preferably 1 to 100 µg/mL. In another embodiment, it may comprises the cyclic peptide at a concentration of 1 to 800 µg/mL or 3 to 500 µg/mL.

When the formulation is a nasal drop, especially a liquid nasal drop, the external preparation of the present invention comprises in the nasal drop solution (nasal drop) the cyclic peptide and/or a derivative thereof and/or a pharmaceutically acceptable salt thereof at a concentration of, for example, 0.0001 to 1000000 µg/mL, preferably 0.001 to 10000 µg/mL, more preferably 0.01 to 1000 µg/mL, yet more preferably 0.1 to 100 µg/mL, particularly preferably 1 to 100 µg/mL. In another embodiment, it may comprises the cyclic peptide at a concentration of 1 to 800 µg/mL or 3 to 500 µg/mL.

The external preparation of the present invention can be formulated, for any formulation as described above, by using methods and constituent materials known to those skilled in the art.

Available constituent materials include such as, without being particularly limited, for example, a gelator, oily ingredient, higher alcohol, fatty acid, ultraviolet absorbing agent, ultraviolet scattering agent, powder, pigment, surfactant, polyhydric alcohol/sugar, polymer, bioactive ingredient, solvent, antioxidant, flavor and antiseptic agent.

Various organic or inorganic gelator compounds can be used.

An inorganic gelator compound includes such as, for example, hydrous or water-absorbable silicate, for example, aluminum silicate (e.g., bentonite), magnesium-aluminum silicate and colloidal silica. As an organic gelator compound, a natural, semisynthetic or synthetic polymer can be used. natural and semisynthetic polymers include such as, for example, polysaccharides such as cellulose, starch, tragacanth, gum arabic, xanthane gum, agar, gelatin, alginic acid and a salt thereof (e.g., sodium alginate and a derivative thereof), lower alkylcellulose (e.g., methylcellulose or ethylcellulose), carboxy- or hydroxy-lower alkylcellulose (e.g., carboxymethylcellulose or hydroxypropylcellulose). A synthetic polymer includes such as, for example, carboxylvinyl polymer, sodium polyacrylate, (vinylmethyl ether/ethyl maleate) copolymer, polymethacrylate, polyvinyl alcohol, polyvinylpyrrolidone, polyacrylate or polymethacrylate. Alternatively, as a gel formulation, commercially available gelators such as, for example, Lubrajel® NP, Lubrajel® CG, Lubrajel® DV, Lubrajel® MS, Lubrajel® OIL, Lubrajel® TW, Lubrajel® DS (Ashland Inc.) can also be used.

As an oily ingredient, for example, various ester, ether, hydrocarbon, silicone and fluorine oil phase ingredient, as well as animal and plant oils and a hardened oil thereof, and waxes of natural origin.

The ester oil phase ingredients include such as, for example, glyceryl tri(2-ethyl hexanoate), cetyl 2-ethylhexanoate, isopropyl myristate, butyl myristate, isopropyl palmitate, ethyl stearate, octyl palmitate, isocetyl isostearate, butyl stearate, butyl myristate, ethyl linoleate, isopropyl linoleate, ethyl oleate, isocetyl myristate, isostearyl myristate, isostearyl palmitate, octyldocecyl myristate, isocetyl isostearate, diethyl sebacate, diisopropyl adipate, isoalkyl neopentanoate, glyceryl tri(capryl-caprinate), trimethylol propane tri(2-ethylhexanoate), trimethylol propane triisostearate, pentaerythritol tetra(2-ethylhexaonate), cetyl caprylate, decyl laurate, hexyl laurate, decyl myristate, myristyl myristate, cetyl myristate, stearyl stearate, decyl oleate, cetyl ricinoleate, isocetyl myristate, isostearyl myristate, isocetyl palmitate, isostearyl palmitate, octyl stearate, isocetyl stearate, isodecyl oleate, octyldodecyl oleate, octyldodecyl linoleate, isopropyl isostearate, cetostearyl 2-ethylhexanoate, stearyl 2-ethylhexanoate, hexyl isostearate, ethylene glycol dioctanoate, ethylene glycol dioleate, propylene glycol dicaprinate, propylene glycol di(capryl-caprinate), propylene glycol dicaprylate, neopentyl glycol dicaprinate, neopentyl glycol dioctanoate, glyceryl tricaprylate, glyceryl triundecanoate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglycerol oleic acid ester, polyglycerol isostearic acid ester, dipropyl carbonate, dialkyl (C12-18) carbonate, triisocetyl citrate, triisoalkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di(2-ethylhexyl) succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoylhydroxystearate, stearyl 12-stearoylhydroxystearate and isostearyl 12-stearoylhydroxystearate.

Hydrocarbon oil phase ingredients include such as, for example, squalane, liquid paraffin, α-olefin oligomer, isoparaffin, ceresin, paraffin, liquid isoparaffin, solid paraffin, polybutene, microcrystalline wax and vaseline.

Silicone oil phase ingredients include such as, for example, dimethylpolysiloxane, methylphenylpolysiloxane, methylcyclopolysiloxane, octamethylpolysiloxane, dacamethylpolysiloxane, dodecamethylcyclosiloxane, methyl hydrogen polysiloxane, polyether-denatured organo(polysiloxane), dimethylsiloxane-methylcetyloxysiloxane copolymer, dimethylsiloxane/methylstearoxysiloxane copolymer, alkyl-denatured organo(polysiloxane), terminal-denatured organo(polysiloxane), amino-denatured silicone oil, amino-denatured organo(polysiloxane), dimethiconol, silicone gel, acryl silicone, trimethyl siloxysilicate, silicone RTV gum.

Fluorine oil phase ingredients include such as, for example, perfluoropolyether, fluorine-denatured organo(polysiloxane), pitch fluoride, fluorocarbon, fluoroalcohol and fluoroalkyl-polyoxyalkylene co-denatured organo(polysiloxane).

Animal and plant oils and a hardened oil thereof, and waxes of natural origin include such as, for example, animal and plant oils and the hardened oil thereof such as beef tallow, hardened beef tallow, lard, hardened lard, horse oil, mink oil, orange roughy oil, fish oil, hardened fish oil, egg yolk, *jojoba* oil; plant oils and a hardened oil thereof such as avocado oil, almond oil, olive oil, *cacao* butter, apricot kernel oil, *kukui* nut oil, sesame oil, wheat germ oil, rice germ oil, rice bran oil, safflower oil, shea butter, soybean oil, evening primrose oil, *camellia* oil, corn oil, rapeseed oil, hardened rapeseed oil, palm kernel oil, hardened palm kernel oil, palm oil, hardened palm oil, peanut oil, hardened peanut oil, castor oil, hardened castor oil, sunflower oil, grape seed oil, *jojoba* oil, hardened *jojoba* oil, macadamia nut oil, meadowfoam oil, cottonseed oil, hardened cottonseed oil, palm oil, hardened palm oil, rose hip oil; waxes such as beeswax, beeswax having high acid value, lanolin, reduced lanolin, hardened lanolin, liquid lanolin, carnauba wax and montan wax.

Higher alcohols include such as, for example, lauryl alcohol, myristyl alcohol, cetyl alcohol, stearyl alcohol, isostearyl alcohol, oleyl alcohol, behenyl alcohol, 2-ethyl hexanol, hexadecyl alcohol, octyl dodecanol.

Fatty acids include such as, for example, caprylic acid, capric acid, undecylenic acid, lauric acid, myristic acid, palmitic acid, palmitoleic acid, stearic acid, isostearic acid, oleic acid, linoleic acid, linolenic acid, arachic acid, arachidonic acid, behenic acid, erucic acid, 2-ethyl hexanoic acid.

Ultraviolet absorbing agents include such as, for example, paraminobenzoate, amyl paraminobenzoate, ethyl dihydroxypropyl paraminobenzoate, glyceryl paraminobenzoate, ethyl paraminobenzoate, octyl paraminobenzoate, octyl dimethyl paraminobenzoate, ethylene glycol salicylate, octyl salicylate, triethanol aminesalicylate, phenyl salicylate, butyl phenyl salicylate, benzyl salicylate, menthyl salicylate, benzyl cinnamate, octyl paramethoxy cinnamate, 2-ethylhexyl paramethoxy cinnamate, glyceryl diparamethoxy cinnamate mono(2-ethylhexanoate), isopropyl paramethoxy cinnamate, paramethoxyhydrocinnamate diethanol amine salt, diisopropyl-disopropyl cinnamate ester mixture, urocanate, urocanate ethyl, hydroxymethoxy benzophenone, hydroxymethoxy benzophenone sulfonate and a salt thereof, dihydroxymethoxybenzophenone, sodium dihydroxymethoxybenzophenone sulfonate, dihydroxybenzophenone, dihydroxy dimethoxybenzophenone, hydroxyoctoxybenzophenone, tetrahydroxybenzophenone, butyl methoxy-dibenzoyl methan, 2,4,6-trianilino-p-(carbo-2-ethylhexyl-1-oxy)-1,3,5-triazine, 2-(2-hydroxy-5-methylphenyl) benzotriazole, methyl-O-aminobenzoate, 2-ethylhexyl-2-cyano-3,3-diphenyl acrylate, phenylbenzimidazole sulfate, 3-(4-methyl benzylidene) camphor, isopropyl dibenzoylmethan, 4-(3,4-dimethoxyphenylmethylene)-2,5-dioxo-1-imidazolidine propionate 2-ethylhexyl, and polymer derivatives or silane derivative thereof, titanium oxide and zinc oxide and dispersion thereof. The zinc oxide and titanium oxide may be surface-treated.

Dermal absorption auxiliary agents include such as, for example, acetic acid, sodium acetate, limonene, menthol, salicylic acid, hyaluronic acid, oleic acid, N,N-diethyl-m-toluamide (N,N-diethyl-3-methyl benzamide), n-butyl stearate, benzyl alcohol, isopropyl myristate, isopropyl palmitate, polypropylene glycol, crotamiton, diethyl sebacate, N-methylpyrrolidone, N-ethylpyrrolidone and lauryl alcohol.

Powders and pigments include such as, for example, pigments such as Pigment Red 104, Pigment Red 201, Pigment Yellow 4, Pigment Blue 1, Pigment Black 401, basic dyes, HC colors, disperse dyes, direct colors, lake pigments such as Pigment Yellow 4 AL lake, Pigment Yellow 203 BA lake; polymers such as nylon powder, silk powder, urethane powder, silicone powder, methyl polymethacrylate powder, cellulose powder, starch, silicone elastomer spherical powder and polyethylene powder; colored pigments such as yellow iron oxide, red iron oxide, black iron oxide, chromic oxide, carbon black, ultramarine, iron blue; white pigments such zinc oxide, titanium oxide, cerium oxide; extender pigment such as tarc, mica, sericite, kaolin and tabular barium sulfate; pearl pigment such as titanium mica; metal salt such as barium sulfate, calcium carbonate, magnesium carbonate, aluminum silicate and magnesium silicate; inorganic powder such as silica, alumina; metal soap such as aluminum stearate, magnesium stearate, zinc palmitate, zinc myristate, magnesium myristate, zinc laurate, zinc undecylenate; bentonite, smectite, boron nitride, etc. The shape (spherical, rod-like, needle-like, tabular, amorphous, scaly, spindle-shaped) and particle diameter of these powders are not particularly limited.

These powders and pigments may be pre-treated by known conventional surface processing such as, for example, fluorine compound processing, silicone processing, silicone resin processing, pendant processing, processing with silane coupling agent, processing with titanium coupling agent, oil solution processing, N-acylated lysine processing, polyacrylic acid processing, metal soap processing, amino acid processing, lecithin processing, inorganic compound processing, plasma processing and mechano-chemical processing.

As the surfactant, any of an anionic surfactant, a cationic surfactant, ampholytic surfactant and non-ionic surfactant can be used as appropriate.

Anionic surfactants include such as, for example, fatty acid soap, α-acylsulfonate, alkylsulfonate, alkylallylsulfonate, alkylnaphthalenesulfonate, alkylsulfate, POE alkylethersulfate, alkylamidesulfate, alkylphosphate, POE alkylphosphate, alkylamidephosphate, alkyloylalkyl taurine salt, N-acylamino acid salt, POE alkylether carboxylate, alkylsulfosuccinate, sodium alkylsulfoacetate, acylisethionate, acylated hydrolyzed collagen peptide salt and perfluoroalkyl phosphate ester.

Cationic surfactants include such as, for example, alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, propyldimethylhydroxypropylammonium behenic amide chloride, diethylaminoethyl-stearamide, dimethylaminopropyl-stearamide and lanolin derivative quaternary ammonium salt. Cationic surfactants also include tertiary amines such as fatty acid amide dialkyl amine and salts thereof.

Ampholytic surfactants include various ampholytic surfactants, for example, those of carboxybetain type, amidebetain type, sulfobetain type, hydroxysulfobetain type, amidesulfobetain type, phoshobetain type, aminocarboxylate type, imidazoline derivative type and amideamine type. Non-ionic surfactants include such as, for example, propylene glycol fatty acid ester, glycerin fatty acid ester, polyglycerin fatty acid ester, sorbitan fatty acid ester, POE sorbitan fatty acid ester, POE sorbitol fatty acid ester, POE glycerin fatty acid ester, POE alkyl ether, POE fatty acid ester, POE hardened castor oil, POE castor oil, POE-POP copolymer, POE-POP alkyl ether, polyether-denatured silicone alkanolamide laurate, alkylamine oxide, hydrogenated soybean phospholipid, hydrogenized soybean phospholipid, polymer surfactant and biosurfactant.

Natual surfactants may also be used, including such as, for example, lecithin, saponin and saccharide surfactant.

Polyhydric alcohols and sugars include such as, for example, ethylene glycol, diethylene glycol, polyethylene glycol, propylene glycol, dipropylene glycol, polypropylene glycol, glycerin, diglycerin, polyglycerin, 3-methyl-1,3-butanediol, 1,3-butylene glycol, sorbitol, mannitol, raffinose, erythritol, glucose, sucrose, fructose, xylitol, lactose, maltose, maltitol, trehalose, alkylated trehalose, mixed isomerized sugar, sulfated trehalose and pullulan. Chemically modificated forms of these can also be used.

Polymers include such as, for example, anionic polymer compounds such as acrylate ester/methacrylate ester copolymer, vinyl acetate/crotonate copolymer, vinyl acetate/crotonate/vinyl neodecanoate copolymer, methylvinyl ether maleate half ester, t-butyl acrylate/ethyl acrylate/methacrylate copolymer, vinylpyrrolidone/vinyl acetate/vinyl propionate copolymer, vinyl acetate/crotonatecopolymer (RUBISET CA: BASF), vinyl acetate/crotonate/vinylpyrrolidone copolymer, vinylpyrrolidone/acrylate copolymer, acrylate/acrylamide copolymer, vinyl acetate/butyl maleate/isoisobornyl acrylate copolymer, carboxyvinyl polymer, acrylate/methacrylate alkyl copolymer, and ampholytic acetate of dialkyl aminoethyl methacrylate polymer, ampholytic polymer compound such as octyl acrylamide acrylate/hydroxypropyl acrylate/butyl methacrylateaminoethyl copolymer, quaternized compound of vinylpyrrolidone/dimethylaminoethyl methacrylate, cationic polymer compounds such as methylvinyl imidazolium chloride/vinylpyrrolidone copolymer, non-ionic polymer compounds such as polyvinylpyrrolidone, vinylpyrrolidone/vinyl acetate copolymer, vinylpyrrolidone/dimethylaminoethyl methacrylate copolymer, vinylcaprolactam/vinylpyrrolidone/dimethylaminoethyl methacrylate copolymer. Polymer compounds of natural origin such as cellulose or derivatives thereof, keratin and collagen or derivatives thereof, calcium alginate, pullulan, agar, gelatin, tamarind seed polysaccharides, xanthan gum, carrageenan, high-methoxyl pectin, low methoxyl pectin, guar gum, gum arabic, crystalline cellulose, arabino galactan, can be karaya, gum tragacanth, alginates, albumin, casein, curdlan, gellan gum and dextran, and glucooligosaccharide, fucose containing polysaccharide, rhamnose containing polysaccharide can also suitably be combined.

Bioactive ingredients include substances which provide skin with some bioactivity when being applied to skin. Bioactive ingredients include those with such as, for example, skin-lightening, anti-inflammatory, anti-aging, ultraviolet protection, slimming, firming, antioxidation, hair growth stimulating/hair growing, suppressing hair growth, moisturizing, promoting circulation, antimicrobial/sterilization, cool/warm feeling, promoting wound cure, alleviating irritation, analgesic and cell-activating effects. Bioactive ingredients include such as plant extracts, seaweed extracts, vitamins and derivatives thereof, amino acids, various peptides other than the cyclic peptide, biopolymers such as sodium hyaluronate and mucopolysaccharide, intercellular lipid constituents such as ceramide, phytosphingosine, cholesterol and phytosterol, and analogues thereof, and enzymatic ingredients.

Examples of suitable combining ingredient include such as, for example, *Angelica keiskei* extract, avocado extract, sweet *Hydrangea* leaf extract, *althea* extract, *arnica* extract, *aloe* extract, apricot extract, apricot kernel extract, isoflavones, *ginkgo* extract, fennel extract, turmeric extract, oolong tea extract, Rose Fruit extract, *echinacea* extract, Baikal skullcup extract, Amur Corktree extract, *Coptis japonica* extract, barley extract, *Hypericum erectum* extract, *Lamium album* extract, cress extract, orange extract, *cacao* extract, desiccated sea water, seaweed extract, hydrolyzed elastin, hydrolyzed wheat powder, hydrolyzed silk, pumpkin seed extract, chamomile extract, carrot extract, *Artemisia capillaris* extract, licorice extract, *hibiscus* extract, *Pyracantha fortuneana* extract, kiwi extract, *cinchona* extract, cucumber extract, guanosine, *gardenia* extract, *Sasa veitchii* extract, *Sophora flavescens* extract, cranberry extract, walnut extract, grapefruit extract, *clematis* extract, *chlorella* extract, mulberry extract, gentian extract, tea extract, yeast extract, burdock extract, rice bran fermentation extract, rice germ oil, comfrey extract, collagen, cowberry extract, *Asarum sieboldii* Miq. extract, *bupleurum* extract, umbilical cord extract, *salvia* extract, soapwort extract, *bamboo* grass extract, *crataegus* extract, *zanthoxylum* extract, *shiitake* mushroom extract, *Rehmannia* root extract, *Lithospermum* root extract, *Perilla frutescens* extract, *Tilia japonica* (Miq.) extract, *Filipendula multijuga* extract, *Paeonia lactiflora* extract, *calamus* extract, white birch extract, *Equisetum arvense* extract, *Hedera helixex* tract, *Crataegus oxyacantha* extract, European elder extract, yarrow extract, peppermint extract, sage extract, tree mallow extract, *cnidium* extract, extract of *Swertia japonica* (Schult.) Makino, soybean extract, jujube extract, soybean fermentation extract, thyme extract, tea extract, clove extract, cogon extract, orange peel extract, *Oenothera tetraptera* extract, *Centella asiatica* extract, *Terminalia sericea* extract, dong quai extract, common marigold extract, peach kernel extract, bitter orange peel extract, extract of *Houttuynia cordata* Thunb., tomato extract, natto extract, *ginseng* extract, garlic extract, wild rose extract, *hibiscus* extract, *Ophiopogon japonicus* extract, parsley extract, honey, banana flower extract, *hamamelis* extract, *parietaria* extract, *Isodon japonicus* (Burm.) *Hara* extract, bisabolol, *loquat* extract, coltsfoot extract, butterbur flower extract, *Poria Sclerotium* extract, butcher's-broom extract, grape extract, *propolis, luffa* extract, safflower extract, peppermint extract, linden extract, tree peonyextract, hop extract, pine extract, horse chestnut extract, *Lysichiton camtschatcense* (L.) Schott extract, *Sapindus mukurossi* Gaertn. extract, Melissa extract, peach extract, bluebottle extract, *eucalyptus* extract, *Saxifraga stolonifera* extract, *Citrus junos* extract, *coix* seed extract, mugwort extract, lavender extract, apple extract, lytchee (*Litchi*) extract, lettuce extract, lemon extract, Chinese milk vetch extract, rose extract, rosemary extract, Roman chamomile extract and royal jelly extract.

Examples also include such as biopolymers such as deoxyribonucleic acid, mucopolysaccharides, sodium hyaluronate, sodium chondroitin sulfate, collagen, elastin, chitin, chitosan and hydrolyzed eggshell membrane; moisturizing ingredients such as amino acids, hydrolyzed peptides, sodium lactate, urea, sodium carbonate pyrrolidone, betain, whey, trimethyl glycine, polypeptides such as lysine/arginine condensate etc.; intercellular lipid constituents such as sphingolipid, ceramide, phytosphingosine, cholesterol, cholesterol derivative, phytosterol derivative, phospholipid and analogues thereof; anti-inflammatory agents such as ε-aminoaminocaproic acid, glycyrrhizic acid, β-glycyrrhetinic acid, lysozyme chloride, guaiazulen, hydrocortisone, tea tree oil; vitamins such as vitamin A and derivatives thereof, vitamin B2 and derivatives thereof, vitamin B6 and derivatives thereof, vitamin C and derivatives thereof, vitamin D and derivatives thereof, vitamin E and derivatives thereof, calcium pantothenate, biotin and nicotinic acid; active agents such as allantoin, diisopropylamine dichloroacetate, 4-aminomethylcyclohexane carbonate; antioxidants such as tocopherol, carotenoids, flavonoids, tannin, lignan and saponin; cell activating agents such as α-hydroxy acid and β-hydroxy acid; circulation accelerating agents such as γ-oryzanol and vitamin E derivative; wound curing agents such as retinol and retinol derivative; skin-lightening agents such as arbutin, kojic acid, placenta extract, sulfur, ellagic acid, linolenic acid, tranexamic acid, glutathione; hair growing agents such as cepharanthine, glycyrrhiza extract, capsicum tincture, hinokitiol, garlic extract iodide, pyridoxine hydrochloride, DL-α-tocopherol, DL-α-tocopherol acetate, nicotinic ac id, nicotinic acid derivative, calcium pantothenate, D-pantothenyl alcohol, acetyl pantothenyl ethyl ether, biotin, allantoin, isopropylmethylphenol, estradiol, ethinylestradiol, carpronium chloride, Benzalkonium chloride, diphenhydramine hydrochloride, Takanal, camphor, salicylic acid, vanillyl nonylate amide, vanillyl nonanoate amide, piroctone olamine, glyceryl pentadecanoate, L-menthol, mononitroguaiacol, resorcin, γ-aminobutyric acid, benzethonium chloride, mexiletine hydrochloride, auxin, female hormones, cantharides tincture, Cyclosporine, zinc pyrithione, hydrocortisone, minoxidil, polyoxyethylene sorbitan monostearate, peppermint oil, Sasanishiki extract.

Antioxidants include such as, for example, sodium bisulfite, sodium sulfite, erythorbic acid, sodium erythorbate, dilauryl thiodipropionate, tocopherol, tolyl biguanide, nordihydroguaiaretinoic acid, parahydroxyanisole, butyl hydroxyanisole, dibutyl hydroxytoluene, ascorbyl stearate, ascorbyl palmitate, octyl gallate, propyl gallate, carotenoids, flavonoids, tannin, lignans, saponins and plant extracts in which the antioxidative effect is recognized such as apple extract or clove extract.

Solvents include such as physiological saline, purified water, ethanol, lower alcohols, ethers, LPG, fluorocarbons, N-methylpyrrolidone, fluoroalcohols, volatile straight chain silicones and next-generation chlorofluorocarbons.

The cyclic peptide of the invention and/or a derivative thereof and/or a pharmaceutically acceptable salt thereof can be used for preparation of the external preparation as described above, and therefore the present invention also relates to a use of the cyclic peptide of the invention and/or a derivative thereof and/or a pharmaceutically acceptable salt thereof for preparing the external preparation.

3. Method of Using the External Preparation

Next, methods of using the external preparation of the invention is explained.

A method of using the external preparation of the invention comprises applying the external preparation of the present invention as described above to the skin and/or mucosa of a subject.

Subjects include human and vertebrates such as, without being particularly limited, for example, birds and mammals. Animals specifically include, for example, experimental animals including rodents such as mice, rats, gerbils, hamsters and guinea pigs, domestic animals such as pigs, goats, horses, sheep and minks, pet animals such as dogs and cats, primates such as human, monkeys, cynomolgus monkeys, rhesus monkeys, marmosets, orangutans and chimpanzees. On the other hand, human may be excluded from the subjects.

Skin and/or mucosa of a subject to which the external preparation is to be applied may be skin or mucosa at any site of the subject, and the external preparation is applicable, for example, to skin or mucosa of head (scalp), face, neck, arms, torso, arms, hands or feet, etc.

Specific method for using the external preparation of the present invention is as follows.

(1) Method of Treating and Preventing Dermatitis

When the external preparation of the present invention is used as a therapeutic/prophylactic of dermatitis, the external preparation can be applied directly to the aimed site of skin and/or mucosa (e.g., the affected site where dermatitis has been developed).

The application frequency is, without being particularly limited, for example, 1 to 10 times a day, preferably 1 to 5 times a day, yet more preferably 1 to 3 times a day. Because the external preparation of the present invention has a long lasting time, it exerts a sufficient effect even if it is applied at relatively low frequency, for example, once a day.

In terms of dosage, the total amount of the cyclic peptide of the invention and a derivative thereof and a pharmaceutically acceptable salt thereof for one application can be, without being particularly limited, for example, 0.0001 to 1000000 μg/mL, preferably 0.001 to 10000 μg/mL, more preferably 0.01 to 1000 μg/mL, yet more preferably 0.1 to 100 μg/mL, particularly preferably 1 to 100 μg/mL. In another embodiment, each dose may comprise the cyclic peptide of the invention at a concentration of 1 to 800 μg/mL or 3 to 500 μg/mL.

(2) Method of Alleviating or Resolving Itch

When the external preparation of the present invention is used as an antipruritic, the external preparation can be applied directly to the aimed site of skin and/or mucosa.

The application frequency is, without being particularly limited, for example, 1 to 10 times a day, preferably 1 to 5 times a day, yet more preferably 1 to 3 times a day.

In terms of dosage, the total amount of the cyclic peptide of the invention and a derivative thereof and a pharmaceutically acceptable salt thereof for one application can be, without being particularly limited, for example, 0.0001 to 1000000 μg/mL, preferably 0.001 to 10000 μg/mL, more preferably 0.01 to 1000 μg/mL, yet more preferably 0.1 to 100 μg/mL, particularly preferably 1 to 100 μg/mL. In another embodiment, each dose may comprise the cyclic peptide of the invention at a concentration of 1 to 800 μg/mL or 3 to 500 μg/mL.

(3) Method of Using as a Cosmetic

When the external preparation of the present invention is used as a cosmetic, the external preparation can be applied directly to the aimed site of skin and/or mucosa.

The application frequency is, without being particularly limited, for example, 1 to 10 times a day, preferably 1 to 5 times a day, yet more preferably 1 to 3 times a day.

In terms of dosage, the total amount of the cyclic peptide of the invention and a derivative thereof and a pharmaceutically acceptable salt thereof for one application can be, without being particularly limited, for example, 0.0001 to 1000000 μg/mL, preferably 0.001 to 10000 μg/mL, more preferably 0.01 to 1000 μg/mL, yet more preferably 0.1 to 100 μg/mL, particularly preferably 1 to 100 μg/mL. In another embodiment, each dose may comprise the cyclic peptide of the invention at a concentration of 1 to 800 μg/mL or 3 to 500 μg/mL.

(4) Method of Treating and Preventing Alopecia, and Method of Stimulating Hair Growth and Method of Growing Hair When the external preparation of the present invention is used as a therapeutic/prophylactic of alopecia, a hair growth stimulant or a hair growing agent, the external preparation can be applied directly to the aimed site (e.g., decalvant site of scalp or skin).

The application frequency is, without being particularly limited, for example, 1 to 10 times a day, preferably 1 to 5 times a day, yet more preferably 1 to 3 times a day.

In terms of dosage, the total amount of the cyclic peptide of the invention and a derivative thereof and a pharmaceutically acceptable salt thereof for one application can be, without being particularly limited, for example, 0.0001 to 1000000 μg/mL, preferably 0.001 to 10000 μg/mL, more preferably 0.01 to 1000 μg/mL, yet more preferably 0.1 to 100 μg/mL, particularly preferably 1 to 100 μg/mL. In another embodiment, each dose may comprise the cyclic peptide of the invention at a concentration of 1 to 800 μg/mL or 3 to 500 μg/mL.

(5) Method of Treating and Preventing Rhinitis

When the external preparation of the present invention is used as a therapeutic/prophylactic of rhinitis, the external preparation can be applied directly to the aimed site (e.g., nasal cavity mucosa). The application frequency is, without being particularly limited, for example, 1 to 10 times a day, preferably 1 to 5 times a day, yet more preferably 1 to 3 times a day.

In terms of dosage, without being particularly limited, for example, for one application to each nasal cavity, the total amount of the cyclic peptide of the invention and a derivative thereof and a pharmaceutically acceptable salt thereof can be 0.0001 to 1000000 μg/mL, preferably 0.001 to 10000 μg/mL, more preferably 0.01 to 1000 μg/mL, yet more preferably 0.1 to 100 μg/mL, particularly preferably 1 to 100 μg/mL. In another embodiment, each dose may comprise the cyclic peptide of the invention at a concentration of 1 to 800 μg/mL or 3 to 500 μg/mL.

4. Medicament

Next, the medicament of the present invention is explained.

The medicament of the present invention comprises one or more cyclic peptides of the invention or derivatives thereof or pharmaceutically acceptable salts thereof.

As mentioned above, similarly to BNP, the cyclic peptide of the present invention or a derivative thereof or a pharmaceutically acceptable salt thereof binds to the receptor NPR-A (also known as GC-A), which has a guanylate cyclase domain, and promotes the production of cyclic guanosine monophosphate (cGMP). It is considered to have effects such as, for example, diuretic action, vasodilation, renin-aldosterone secretion suppressing action, sympatholytic activity and hypertrophy suppressing action. Also, the compounds of the invention is considered to have a superior efficacy and effect, particularly a superior immediate effect, as compared with BNP.

Therefore, the medicament of the present invention can be used for a similar object as a conventional medicament comprising BNP as an active agent.

Diseases for which the medicament of the present invention is applicable include such as, without being particularly limited, for example, the aforementioned various diseases as well as hypertension, unstable angina, acute myocardial infarction, edematous diseases, renal failure, cardiac failure, immune diseases, obesity and metabolic syndrome.

A formulation of the medicament of the present invention can be, without being particularly limited, addingly to the external preparations as mentioned above, for example, formulations for oral administration such as tablets, capsules, granules, powders, oral solution, syrup and oral jelly, formulations for oral application such as buccal tablets, buccal spray formulation, buccal semi-solid formulation and mouthwash, formulations for administration via injection such as an injection and infusion, dialysis formulation such as dialysis solution, as well as an inhalant, eye drop, ocular ointment, ear drop, vaginal tablet and vaginal suppository.

Working Examples

Hereinbelow, the present invention is further specifically illustrated by working examples. It should be noted that the present invention is not limited by these working examples.

1. Preparation of the Cyclic Peptide

Firstly, a cyclic peptide composed of the amino acid sequence expressed by Formula I-a is synthesized.

Specifically, a linear peptide consisting of 17 amino acids was formed by sequentially binding amino acids by solid-phase peptide synthesis using a peptide synthesizer. Subsequently, protecting groups at Cys1 and Cys17 were detached before treating with iodine (I2) to form a cysteine binding between oxidatively same amino acid residues, thereby forming a cyclic peptide.

A composition comprising the obtained cyclic peptide was purified by reverse-phase high performance liquid chromatography (reverse-phase HPLC) and then lyophilized to yield a purified cyclic peptide as white powder.

Mass spectroscopy was performed on the obtained cyclic peptide.

Conditions for HPLC are shown below:
Apparatus: Agilent 1100
Flow rate: 1.0 ml/min
Eluent A: 0.1% trifluoroacetic acid/water Eluent B: 0.1% trifluoroacetic acid/acetonitrile
Gradient: 80% Eluent B, isocratic
Conditions for Mass spectroscopy (MS) are shown below:
Apparatus: Thermo Finnigan LCQ Advantage
Ionization method: electrospray ionization
Analytical method: ion trapping The observed results, m/z=901.83 ($[M+2H]^{2+}$), m/z=1801.84 ($[M+H]^+$), confirmed that above peptide is in agreement with the theoretical values of the molecular weight (1802.07) and the mass number (1800.8069) calculated from the composition formula of the cyclic peptide of interest ($C_{72}H_{120}N_{24}O_{24}S_3$).

Furthermore, the purity of the above peptide was measured by HPLC using following conditions:
Column: Discovery C18, 4.6 mm×250 mm, particle diameter 5 micron
Column temperature: room temperature
Eluent A: 0.1% trifluoroacetic acid/water
Eluent B: 0.1% trifluoroacetic acid/acetonitrile
Gradient: 10 to 30% Eluent B/20 minutes
Flow rate: 1.2 ml/min
Temperature: room temperature
Injected volume: 20 µl
Detector: UV detector (detection wavelength: 215 nm)
The result of measurement confirmed that the purity of the obtained protein was 99.2%.

2. Preparation of Formulation
2.1 Preparation of Gel Formulation

Preparation of a gel-based formulation comprising a cyclic peptide composed of the amino acid sequence expressed by Formula I-a (in the working examples below, "B ring" is referred to mean a cyclic peptide expressed by such Formula I-a) (B ring gel formulation, Working Examples) and a gel-based formulation comprising human BNP (BNP gel formulation, Comparative Examples) were carried out as follows.

0.1 g of methyl-p-hydroxybenzoate (trade name: Mekkins-M, Ueno Fine Chemicals Industry, Ltd.), 0.2 g of phenoxyethanol and 3.0 g of 1,2-pentanediol were weighed into one same vessel, heated to 60 to 70° C. to make a homogenous solution, and this solution was poured into a mixer.

Next, added into the mixer 6.0 g of concentrated glycerin, and then the mixture of 0.44 g of carboxyvinyl polymer (trade name: Carbopol® 940, Lubrizol Advanced Materials Corporation) and 0.08 g of xanthane gum (trade name: KELTROL® T, CP Kelco, Inc.), and the mixuter was stirred with a paddle until they dispersed sufficiently.

Then 83.95 g of purified water was gradually added with stirring with a paddle. The mixer was heated to 70 to 80° C. while stirring with a paddle or disper until the dispersed contents were dissolved to give a solution. Subsequently, the disper was stopped and the solution was cooled immediately after confirming that the contents in the solution were dissolved. When the temperature of the mixer reached approximately 40° C., 6.0 g of Lubrajel® NP from Ashland Inc. (glycerin 2.7 g, carboxyvinyl polymer 0.06 g, sodium polyacrylate 0.018 g, water 3.222 g) was added to the solution, mixed uniformly with a paddle. Subsequently, 0.230 g of potassium hydroxide was further added to neutralize the solution, then the rotation of the paddle was stopped when the temperature of the mixer reached 25° C. to prepare a gel base.

Next, 20.1 mg of the cyclic peptide (B ring) composed of the amino acid sequence expressed by Formula I-a was dissolved in 144 mL of physiological saline to obtain B ring solution. 0.131 mL of this solution was admixed with 10 g of the gel base obtained as described above, and the mixture was stirred uniformly to prepare a gel based formulation (B ring gel formulation) containing B ring at a concentration of about 1 µM (about 1.8 µg/g). Similarly, gel based formulations containing B ring at concentrations of about 0.3 µM (about 0.54 pig/g), about 0.5 µM (about 0.9 µg/g) and about 2.0 µM (about 3.6 µg/g) were prepared. In the working examples below, as long as it is specifically described otherwise, "B ring gel formulation" used contained B ring at a concentration of about 1 µM.

Next, 20.5 mg of human BNP-32 (American Peptide Company) was dissolved in 118 mL of physiological saline to obtain BNP solution. 0.2 mL of this solution was admixed with 10 g of the gel base obtained as described above, and the mixture was stirred uniformly to prepare a gel based formulation (BNP gel formulation) containing BNP-32 at a concentration of about 1 µM. Similarly, gel based formulations containing BNP-32 at concentrations of about 0.5 µM and 2.0 µM were prepared. In the working examples below, as long as being specifically described otherwise, "BNP gel formulation" used contained BNP at a concentration of about 1 µM.

2.2 Preparation of Nasal Drop

A nasal drop comprising the cyclic peptide (B ring) composed of the amino acid sequence expressed by Formula I-a (B ring nasal drop, Working Examples) and a nasal drop comprising human BNP (BNP nasal drop, Comparative Examples) were prepared as follows.

Firstly, the cyclic peptide (B ring) composed of the amino acid sequence expressed by Formula I-a was dissolved in physiological saline, the concentration was adjusted to prepare B ring nasal drop containing B ring at a concentration of about 1 µmol/1 (about 1.8 µg/g).

Next, B ring nasal drop was filled in a quantitative nasal spray container (AS ONE Corporation) and the amount ro be sprayed for each administration was adjusted to 100 µl (0.1 ml), resulting B ring nasal drop.

Similarly, a BNP nasal drop comprising human BNP (American Peptide Company) at a concentration of 1 µmol/l was obtained, filled in a quantitative nasal spray container (AS ONE Corporation), and the amount ro be sprayed for each administration was adjusted to 100 µl (0.1 ml), resulting BNP nasal drop.

3. Confirming Therapeutic Effect on Dermatitis
3.1 Confirming the Effect of B Ring Gel Formulation For subjects suffering various dermatitis, B ring gel formulation as described was applied onto the affected site, and changes in symptoms before and after the application were observed. When possible, as a comparative example, BNP gel formulation as described was applied onto another affected site on the same subject where B ring gel formulation had not been applied, and changes in symptoms before and after the application were observed. For pruritus, VAS (Visual Analogue Scale) was used for evaluating each affected site on 10 stages.

The examination results are shown in Tables 1 to 7 along with age, sexuality, symptoms of the subject, and formulation given to the subject.

TABLE 1

| Case | Treatment | Disease | Pre-application symptoms (severity) | Post-application symptoms (severity) | Pruritus before and after application (VAS) | Notes |
|---|---|---|---|---|---|---|
| D1 Age: 30's Sex: male | 2 µM B ring gel formulation 1 application | atopic dermatitis | Face: presented with erythema, scales and skin desiccation (moderate disease). Limbs: presented with erythema, lichenification, skin desiccation and scratch scar (severe) | Face: itches removed 2 min after 1 application. Desiccatien, scales and erythema remitted (mild). After 3 days of application, erythema, scales, infiltration and desiccation remarkably remitted (insignificant). Right forearm: itches stopped to some extent after 1.5 min on B ring-applied site. No itching or tingling after 2 min. Lichenification/stiffness remitted after 4 min. Desiccabon improved. Skin moisturized and soft, with natural appearance. No subjective discomfort (moderate). | face 8→0 right arm 7→0 | |
| | 2 µM BNP gel formulation 1 application | | | Face: itches realized after 4 min. erythema and scalcs more distinguished than B ring side. Left forearm: after 4 min, skin was still dry. No improvement in licherification. Rough and stiff skin (severe). | face 8→4 left arm 7→4 | |
| D7 Age: 20's Sex: male | 1 µM B ring gel formulation 1 application | atopic dermatitis | Flushing, infiltrating erythema, scales, many scratch scars (severe) accompanied by strong itches causing sleep disruption and desire to scratch. | Right back: itches stopped after 3 min. Pushing erythema, infiltration ard scales remitted. Skin became soft (moderate). | 8→0 | |
| | 1 µM BNP gel formulation 1 application | erythroderma | | Left back: still itching after 3 min. 10 remission of flushing erythema. infiltration and sizdes (severe). | 8→4 | |
| D3 Age: 10's Sex: male | 0.5 µM B ring gel formulation 1 application | atopic dermatitis | Presented wth infiltrating erythema, scales, papules, (moderate) accompanied by tingling itches. | Right back: no tingling itches 30 sec after application. Skin felt normal. Erythema, infiltration and scales remitted after 4 min (mild). | 6→0 | |
| | 0.5 µM BNP gel formulation 1 application | | | Left back: still itching after 4 min, with no remission of erythema, infiltration and scales (modorate). | 6→6 | |

TABLE 2

| Case | Treatment | Disease | Pre-application symptoms (severity) | Post-application symptoms (severity) | Pruritus before and after application (VAS) | Notes |
|---|---|---|---|---|---|---|
| D4 Age: 20's Sex: male | 2 µM B ring gel formulation 1 application | atopic dermatitis | Presented with infiltrating erythema, scales, many scratch scars with exudation (severe) accompanied by strong itches that cause sleep disruption on the back. lichenification, erythema, scales and scratch scars on forehead (severe). | Right back: itches relieved just after application. No itches after 2 min with remission of crythema and infiltration (moderate). Forehead: itches reduced after 1.5 min After 5 min skin was soft with no lichenification Erythema and scales remitted. Wound quickly healed. Scratch scars epithellzec. | 10→0 | |
| | 2 µM BNP gel formulation 1 application | | Back: presented with many scratch scars with exudation, infiltration, erythema, crusts (severe). | Left back: still itching after 4 min with no remission of erythema and infiltration (severe). Forehead: no improvement in lichenification, desiccation and scales, with remaining itches (severe). | 10→3 | |
| D5 Age: 20's Sex: male | 1 µM B ring gel formulation 1 application | atopic dermatitis | Presented with infiltrating erythema, edema and crusts (severe) accompanied by strong tingling itches. Back: presented with many scratch scars with exudation. infiltration. erythema, crusts and papules (severe). | Right face: itches, edema and infiltration remitted/relieved just after application. Skin fell no itch and moisturized after 1 min (moderate). No itches at all after 2 min. Edema and erythema remittec. Right eye became easy to open | 9→0 | |
| | 1 µM BNP gel formulation 1 application | | | Left face: stil itching after 3 min with no remission of erythema, infiltration and edema. Being difficult to open left eye (severe). | 9→4 | |

TABLE 2-continued

| Case | Treatment | Disease | Pre-application symptoms (severity) | Post-application symptoms (severity) | Pruritus before and after application (VAS) | Notes |
|---|---|---|---|---|---|---|
| D6 Age: "0"s Sex: male | 1 µM B ring gel formulation 1 application | atopic dermatitis prurigo nodularis | Presented with lichenification, prurigo nodularis, erythema, scales, papules and many scratch scars (severe) accompanied by strong itches. Back: presented with many scratch scars with exudation, infiltration, erythema, crusts and papules (severe). | Right back: Aches improved/relieved after 3 min. Lichenification, prurigo nodularis, erythema, scales, scratch scars all improved as compared to loft. Skin was soft and moisturized (moderate). | 8→0 | |
| | 1 µM BNP gel formulation 1 application | | | Left bock: still itching aftor 4 min with no remission of erythema and infiltration (severe). Forehead: lichenification, desiccation and scales not improved, with itches left (severe) | 8→3 | |

TABLE 3

| Case | Treatment | Disease | Pre-application symptoms (severity) | Post-application symptoms (severity) | Pruritus before and after application (VAS) | Notes |
|---|---|---|---|---|---|---|
| D7 Age: 20's Sex: male | 0.3 µM B ring gel formulation 1 application | atopic dermatitis | Presented with infiltrating erythema, papules, exudation and many scratch scars with crust (severe) accompanied by strong itches that cause sleep disruption. | No itches after 1 min. Erythema remitted and exudation stopped after 10 min. 1 application/day for 3 days cleared of infiltrating erythema, papules, exudation and scratch scars. Remarkably improved crusts, partly left mild erythema (mild). | 10→0 | Intractable stroid-resistance |
| D8 Sex: male | 0.5 µM B ring gel formulation 1 application, 5 days | atopic dermatitis | Presented with erythema, infiltration, scales, crusts, scratch scars and skin desiccation (severe). | 5 days after application, erythema, infiltration, scales, crusts and wound quickly cured with little scratch scars left (mild). Desiccation remarkably remitted Skin moisturized and soft. | 8→1 | Intractable steroid-resistance |
| D9 Age: 30's Sex: male | B ring gel formulation 2 applications/ day 1 day | atopic dermatitis | Left forearm presented with many scratch scars with exudation, infiltration, erythema, papules, accompanied with tingling strong itches (VAS10) (severe) | Itches removed in 2 min (VAS 0). Erythema and exudation improved. Severity of rash improved to moderate disease level after 5 min. After 1 more application given on the same night, there was no itches for 3 days thereafter. Scratch scars epithelized. | 10→0 | |
| D10 Age: 50's Sex: female | 1 µM B ring gel formulation 1 application | atopic dermatitis | Presented with infiltrating erythema, scales, papules and many scratch scars (severe) accompanied by intermediate strong itches | Right forearm: itches topped after 3 min. Erythema and infiltration improved (moderate). | 8→0 | |
| | 1 µM BNP gel formulation 1 application | | | Left forearm: still itching after 4 min with no remission of erythema and infiltration (severe) | 8→4 | |
| D11 Age: 40's Sex: female | 1 µM B ring gel formulation 1 application | atopic dermatitis | Presented with infiltrating erythema, scales and many scratch scars (severe) accompanied by drastic itches and tautness. Back: presented with many scratch scars with exudation, infiltration, erythema, crusts and papules (severe). | Right face: immediately after application, itches and skin tautness relieved, with erythema getting better. No itching after 1 min. Erythema, infiltration and desiccation remitted (moderate). | 10→0 | |
| | 1 µM BNP gel formulation 1 application | | | Left face: still itching after 3 min, having erythema, infiltration and edema with swollen feeling (severe). | 10→4 | |

TABLE 4

| Case | Treatment | Disease | Pre-application symptoms (severity) | Post-application symptoms (severity) | Pruritus before and after application (VAS) | Notes |
|---|---|---|---|---|---|---|
| D12 Age: 40's Sex: female | 1 μm B ring gel formulation 1 application | atopic dermititis | Strong tingling itches, disrupted sleep, infiltrating erythema, scales, exudation, cracks, crusts, scratch scars; eyes cannot be opened due to exudate sealing eyelids (severe). | Right face: itches remitted after 3 min. Edema, erythema and infiltration started to be remitted. After 30 min, anti-inflammatory effect observed, exudation stopped, wound epithelization promoted, cracks almost epithelized. Edema, erythema and infiltration remitted to some extent. Eyelids became openable steadily. | 10 → 1 | |
| | 1 μm BNP gel formulation 1 application | | | Left face: still having tingling itches after 3 min with no remission of erythema and infiltration. Itches till left after 30 min. | 10 → 6 | |
| D13 Age: 20's Sex: female | 1 μm B ring gel formulation 1 application 1 μm BNP gel formulation 1 application | atopic dermititis | Obvious infiltration, erythema and papules all over the face, accompanied with strong itches and hot flash (severe). | Right face: erythema started to be remitted and itches removed just after application. Erythema and infiltration remitted after 4 min (moderate). Left face: itching with hot flush and redness just after application. Itches removed after 4 min. | 8 → 0 (immediate after application) 8 → 0 (after 4 minutes) | |
| D14 Age: 20's Sex: female | 1 μm B ring gel formulation 1 application 1 μm BNP gel formulation 1 application | atopic dermititis | Hand eczema of which main symptom is contact dermititis due to detergent and disinfectant. Presented with lichenification, erythema, scales and scratch scars (severe). Sleep disruption by strong itches (VAS9). | Right hand: itches removed after 3 min (VAS0). Lichenification improved, skin got soft, erythema and infiltration remitted (moderate). Left hand: no improvement in lichenification and erythema after 10 min (severe). | 9 → 0 9 → 4 | Steroid-resistance; intractable lichenification which cannot be remitted within this short time (3 min) by conventional therapy. |

TABLE 5

| Case | Treatment | Disease | Pre-application symptoms (severity) | Post-application symptoms (severity) | Pruritus before and after application (VAS) | Notes |
|---|---|---|---|---|---|---|
| D15 Age: 20's Sex: female | 1 μm B ring gel formulation 1 application/day 3 days | atopic dermititis | Presented with erythema, infiltration, scales, crusts, scratch scars (severe), with strong itches. | Erythema, infiltration, scales and crusts wound epithelization improved 3 days after application. Scratch scars significantly improved. Only mild erythema and scales observed (mild). Desiccation relieved, improved and moisturzed skin texture. Itches and scratch scars significantly improved. | 9 → 1 | |
| D16 Age: 60's Sex: female | 1 μm B ring gel formulation 1 application | contact dermititis | Contact dermititis due to hair dye with erythema, edema and infiltration along hairline (moderate disease) accompanied by strong tingling itches (VAS8) | Right side: tingling itches removed after 1 min. Itches eliminated after 3 min (VAS0), felt better than left. Erythema and infiltration remitted. Anti-inflammatory effect observed. Edema improved (mild). | 8 → 0 | |
| | 1 μm BNP gel formulation 1 application | | | Left side: symptoms less improved than right (moderate). | 8 → 4 | |
| D17 Age: 40's Sex: female | 1 μm B ring gel formulation 1 application | chronic eczema | Presented with infiltrating erythema, scales, lichenification, crusts, papules and skin desiccation (severe) accompanied by drastic itches and tautness. | Right face: itches stopped just after application. Erythema remitted. No scales and desiccation after 2 min. Skin was moisturized (moderate). Forehead: itches controlled after 1.5 min. No lichenification after 5 min. Skin got soft. Erythema and scales remitted, scratch scars epithelized and wound quickly healed. | 10 → 0 | |
| | 1 μm BNP gel formulation | | | Left face: still itching and taut after 4 min with no remission of desiccation, scales, erythema and infiltration (severe). | 10 → 5 | |

TABLE 5-continued

| Case | Treatment | Disease | Pre-application symptoms (severity) | Post-application symptoms (severity) | Pruritus before and after application (VAS) | Notes |
|---|---|---|---|---|---|---|
| D18 Age: Sex: female | 1 application 1 μm B ring gel formulation 1 application | eczema | Presented with erythema, edema, infiltration, scales and papules (severe). | After 15 min, erythema, edema, infiltration and scales significantly remitted and skin texture improved (mild). | 8 → 0 | |
| | 1 μm BNP gel formulation 1 application | | | After 15 min, still many scales, erythema, edema and infiltration left. Skin texture is rough and still itching. | 8 → 4 | |

TABLE 6

| Case | Treatment | Disease | Pre-application symptoms (severity) | Post-application symptoms (severity) | Pruritus before and after application (VAS) | Notes |
|---|---|---|---|---|---|---|
| D20 Age: 20's Sex: female | 1 μm B ring gel formulation 1 application | wheal, insect bites | Presented with multiple wheals, erythema and very strong itches on both lower limbs. | Right lower limb: itches removed just after application. Erythema started to be remitted after 1.5 min. Wheals disappeared in about 1 hour. | 10 → 0 | |
| D31 Age: 30's Sex: female | 1 μm B ring gel formulation 1 application | wheal, insect bites | Presented with multiple wheals and very strong itches on right lower limb. | Left lower limb: itches removed 1 min after application, wheals remitted after 2 min. | 10 → 0 | |
| D21 Age: 10's Sex: female | 1 μm B ring gel formulation 2 applications/ day 3 days | childhood xerotic eczema | Presented with desiccation, many milary large papules, desquamation, strong pruritus, and many scratch scars on trunk; incrustation, erythema and lichenification due to scratching (severe). | Right back: itches stopped after 30 sec. Desiccation, scales and erythema improved in a few minutes, Skin got moisturized. After 3 days, wounds quickly epithelized leaving one scratch scar. Skin is smooth and moisterized with no desiccation (insignificant). | 8 → 0 | |
| | 1 μm BNP gel formulation 1 application | | | Left back: desiccation, scales and erythema left after few minutes. | 8 → 3 | |
| D32 Age: 40's Sex: female | 1 μm B ring gel formulation 1 application | parapsoriasis guttata | Presented with multiple erythrokeratoderma with sticking small scales on back. | Scales, erythema and infiltration remitted after 4 min. | N/A | |
| D33 Age: 60's Sex: male | 0.5 μm B ring gel formulation 2 applications/ day 1 week | psoriasis vulgaris | Both lower limbs presented with many red plaques with attached small scales having clear margin. | Scales and erythema started to be remitted 10 min after 1st application. After 1 week, no scales left. | N/A | |
| D34 Age: 30's Sex: male | 2 μm B ring gel formulation 1 application | psoriasis vulgaris | Many red plaques with attached thick scales having clear margin presented on back and neck. | Back psoriasis: thick scales started to be remitted in 3 min after application, almost disappeared after 30 min. Neck psoriasis: erythema and scales remitted in 3 min after application. | N/A | |

TABLE 7

| Case | Treatment | Disease | Pre-application symptoms (severity) | Post-application symptoms (severity) | Pruritus before and after application (VAS) | Notes |
|---|---|---|---|---|---|---|
| D23 Age: 30's Sex: male | 2 μm B ring gel formulation 2 applications/ day 1 day | cyshidrotic eczema dyshidrosis | Fingers presented with many intractable bullae, being eczematous with erythema and cracks. | Erythema and bullae remitted in 2 min after application. After 1 day, erythema and scales remitted and bullae disappeared. | N/A | Intractable with steroid ointment. |

TABLE 7-continued

| Case | Treatment | Disease | Pre-application symptoms (severity) | Post-application symptoms (severity) | Pruritus before and after application (VAS) | Notes |
|---|---|---|---|---|---|---|
| D24 Age: 50's Sex: male | 2 µm B ring gel formulation 1 application | miliaria hyper-hidrosis | Red small papules and flare with itches. | Pruritus, erythema and red small papules remitted after 3 min. | N/A | |
| D25 Age: 50's Sex: male | 1 µm B ring gel formulation 1 application | chronic urticaria | Many wheals with drastic itches. | Pruritus removed just after application. Wheals started to be gradually remitted just after application and disappeared after 7 min. | 10 → 0 | |
| D26 Age: 30's Sex: female | 1 µm B ring gel formulation 1 application | rosacea | Suffering from rosacea for 2 years. 2 months of facial application of a steroid ointment exacerbated the symptoms, developing telangiectasia, diffuse flare, follicular papule and pustule on cheeks. Subjective symptoms include tingling itches and tautness. | Tautness and tingling itches removed just after application. Diffuse flare, follicular papule and pustule remitted after 1 min. After 1 week of 2 application/day, anti-inflammatory effect was observed. Diffuse flare, follicular papule and pustule remarkably improved. Itches and hot flush removed. | N/A | Intractable after 2 yrs of conventional therapy without satisfactory therapeutic effect. |
| D35 Age: 60's Sex: female | 4 µm B ring gel formulation 1 application | perioral dermititis | 2 years of facial application of a steroid ointment resulted in circumoral telangiectasia, diffuse flare and follicular papule. Subjective symptoms include heat sensation. | Diffuse flare and follicular papule remarkably remitted 2 min after application. After 2 application/day for 2 days flare improved and scales removed. | N/A | |

TABLE 8

| Case | Treatment | Disease | Pre-application symptoms (severity) | Post-application symptoms (severity) | Pruritus before and after application (VAS) | Notes |
|---|---|---|---|---|---|---|
| D36 Age: 50's Sex: male | 2 µm B ring gel formulation 1 application | rosacea | Presented with circumoral telangiectasia, diffuse flare and follicular papule. | Diffuse flare and follicular papule remarkably remitted 2 min after application | | |
| D37 Age: 20's Sex: female | 1 µm B ring gel formulation 1 application/ day 3 days | acne vulgaris | Oily skin accompanied by suppurative inflammation with many pustules and comedos on lower jaw. | Seborrhea remitted 2 min after application. Anti-inflammatory effect remitted suppurative inflammation and pustules on lower jaw. Pustules reduced and dried 3 days after application, and domedos disappeared. | N/A | Faster and stronger anti-inflammatory effect than applying/ administrating conventional antibiotics. |
| D38 Age: 40's Sex: female | Right cheek: 1 µm B ring gel formulation 1 application/ day 2 weeks Left cheek: BNP gel single application, then 1 µm B ring gel formulation 1 application/ day 2 weeks | acne vulgaris | Multiple follicular papules and pustules on both cheek. Oily skin. | Anti-inflammatory effect observed 3 min after application, pustules and papules started to be reduced and flattened, and flare started to be removed. After 1 week pustules and papules substantially remitted and flare further remitted. After 2 weeks pustules, papules and flare almost disappeared. No change in symptoms 3 min after application. After switching to B ring formulation, similar effects as right cheek were obtained. | N/A | |
| D39 Age: 10's Sex: male | Right cheek: 2 µm B ring gel formulation 1 application | acne vulgaris | Oily skin accompanied by sppurative inflammation with multiple red papules and pustules on both cheeks. | Anti-inflammatory effect by B ring application was observed on right cheek in 3 min. Suppurative inflammation remitted. | | |

TABLE 8-continued

| Case | Treatment | Disease | Pre-application symptoms (severity) | Post-application symptoms (severity) | Pruritus before and after application (VAS) | Notes |
|---|---|---|---|---|---|---|
| | Left cheek: gel formulation 1 application | | | No anti-inflammatory effect on gel-applied left side. | | |
| D40 Age: 10's Sex: female | 4 µm B ring gel formulation 1 application | acne vulgaris | Seborrheic skin with multiple comedos and follicular papules/pustules on forehead. | Comedos faded in 5 min after application. Oily skin improved to better texture. Red papules and pustules reduced. | | |

As shown in Tables 1 to 8, in all subjects, or in all dermatitis of any symptoms, emission or elimination of various symptoms of dermatitis was observed at the site where B ring gel formulation was applied.

Specifically, when B ring gel formulation was applied, remission or elimination of pruritus was observed immediately after the application. Generally in dermatitis, patients tend to scratch where pruritus was felt, potentially causing severer dermatitis. Such a remarkable remission or elimination of pruritus in this manner can consequently prevent aggravation of dermatitis.

In all cases, the effects of B ring gel formulation were superior to those with BNP gel formulation. Specifically, B ring gel formulation had faster-acting and longer-lasting effects as well as more potent antipruritic effect as compared with BNP gel formulation. It was confirmed that these effect cannot be obtained by the gel base.

3.2 Comparing B Ring Gel Formulation to Gel Base by Two-Sided Application

For subjects suffering various dermatitis, either B ring gel formulation or the gel base was applied to the affected site, and changes in symptoms before and after the application were observed (Table below).

4. Confirming Cosmetic Effect

Effects of a cosmetic comprising B ring were evaluated from the results obtained using a gel formulations, a bath agent and a hair cosmetic product (shampoo or rinse) or body soap comprising the B ring to confirm their effects.

4.1.1 Confirming Skin-Improving Effect (Comparing B Ring Gel Formulation to BNP Gel Formulation)

The B ring gel formulation or BNP gel formulation was applied to subjects. The B ring gel formulation was applied on the right cheek or eye of each subject, the BNP gel formulation on the left cheek or eye, and changes in skin conditions were observed and compared (Table below). The changes in skin conditions were determined based on physical sensory evaluation by the subject and our objective observation as physicians.

TABLE 9

| Case | Applied site | Treatment | Disease | Pre-application symptoms | Post-application symptoms |
|---|---|---|---|---|---|
| E1 Age: 20's Sex: female | Right | B ring | atopic dermatitis | Face presented with infiltrating erythema, scales and pigmentation, with intractable itches | Flare and pigmentation removed 2.5 min after application. Skin elasticity and desiccation improved. Itches eliminated. |
| | Left | gel base | | | No remission of pigmentation, infiltrating erythema, scales and desiccation, with itches left. |
| E2 Age: 30's Sex: male | Right | B ring | chronic eczema | Stiffness and hard lichenification on both forearms, with infiltrating erythema and desiccation. | Flare remitted soon after application. After 3 min skin softened and moisturized. Itches eliminated. |
| | Left | gel base | | | No improvement in lichenification, itching and flare after 3 min. |
| E3 Age: 10's Sex: female | Right | B ring | atopic dermatitis | Presented with hot flush and puffiness. | Flare started to fade soon after application, and was remarkably remitted after 3 min. |
| | Left | gel base | | | No improvement in flushing after 3 min. |
| E4 Age: 40's Sex: male | Right | B ring | chronic eczema | Stiffness and hard lichenification on both forearms, with infiltrating erythema, scales and hot sensation. | Flare remitted soon after application, remarkably remitted after 3 min with improved infiltration and hot sensation, and softened skin. |
| | Left | gel base | | | Infiltration felt 3 min after application. Skin was hard with unimproved flare and hot sensation. |

TABLE 10

| Case | Applied site: method | Pre-application symptoms | Post-application symptoms |
|---|---|---|---|
| F1<br>Age: 69<br>Sex: female | Right: B ring gel formulation 0.5 μmol, 1 application | Presented with wrinkles, cheek flabbiness, pigmentation on eye corner. | 2 min after application, wrinkles on eye corner and forehead were shallowed, skin was full. After 3 min, cheek flabbiness and skin texture were improved, and pigmentation on eye corner was less prominent. After application for 3 days, large wrinkle on cheek was shallowed, flabbiness was improved, skin was firm, resilient, full and moisturized. |
| | Left: applied gel base | | No improvement in wrinkles after 3 min. |
| F2<br>Age: 45<br>Sex: female | Right: B ring gel formulation 0.5 μmol, 1 application | Presented with wrinkles, cheek flabbiness and desiccation. | 2 min after application, wrinkles at eye corner due to desiccation was less prominent, skin texture was improved, moisturized and softened. |
| | Left: applied gel base | | No improvement in wrinkles and desiccation after 2 min. |
| F3<br>Age: 21<br>Sex: female | Right: B ring gel formulation 2 μmol, 1 application | Presented with desiccation, light erythema, tautness and itch. | 30 sec after application, skin desiccation was improved, skin was moisturized and flexible with no tautness. After 1 min, flare was remitted and itches were removed. After 4 min, further softness was given and desiccation was remarkably improved. |
| | Left: applied gel base | | No improvement observed in desiccation, itching and flare after 4 min. |
| F4<br>Age: 24<br>Sex: female | Right; B ring gel formulation 2 μmol, 1 application | Presented with desiccation and light erythema. | 3 min after application, skin desiccation was improved, skin was moisturized and firm, with improved texture. Skin was flexible, soft and moisturized. |
| | Left: applied gel base | | No improvement observed in desiccation and flare after 3 min. |
| F5<br>Age: 28<br>Sex: female | Right: B ring gel formulation 2 μmol, 1 application | Presented with wrinkles on both corners of eye, and desiccation. | 2 min after application, wrinkles on both corners of eyes were less prominent, cheek dryness was improved, skin was moisturized and flexible. Perioral desiccation was remitted and skin became full and flexible. |
| | Left: applied gel base | | No improvement observed in desiccation and wrinkles after 2 min at gel-applied site on the left. |
| F6<br>Age: 30<br>Sex: female | Right: B ring gel formulation 2 μmol, 1 application | Presented with skin desiccation, oily skin and red papules around nose, and light erythema and rough skin texture. | 1 min after application, itches were remarkably remitted. After 3 min, skin desiccation and flare were improved, and skin was moisturized and flexible with improved texture. Red papules around nose almost disappeared, combination state of desiccation and oily skin was improved, and skin is kept healthy. |
| | Left: applied gel base | | 3 min after application, desiccation, flare and itches are left, and seborrhea and papules around nose were not remitted. |

Table below summarizes examples in which B ring gel formulation was applied without applying two-sided. The changes in skin conditions were determined by similar method as described above.

TABLE 11

| Case | Method of application | Pre-application symptoms | Post-application symptoms |
|---|---|---|---|
| G1<br>Age: 50<br>Sex: female | B ring gel formulation 1 μmol 1 application | Presented with cheek flare, open pores, rough and hard skin texture. | After B ring application, flare was repressed, skin texture was improved, skin was moisturized and softened. |
| G2<br>Age: 49<br>Sex: female | B ring gel formulation 2 μmol 1 application | Presented with wrinkles and desiccation on forehead and eye corner. | 3 min after application at B ring-applied site, wrinkles on forehead and eye corner were shallowed and less prominent, skin desiccation was improved, and skin was moisturized and flexible. |
| G3<br>Age: 40's<br>Sex: male | B ring get formulation 1 μmol 1 application | Presented with male skin desiccation and roughness. | 1 day after application at ring-applied site, skin desiccation and roughness were improved, and razor burn was prevented. |
| G4<br>Age: 50's<br>Sex: male | B ring gel formulation 2 μmol 1 application | Presented with miliaria and pruritus accompanied with flare. | 3 min after application at B ring-applied site, miliaria was prevented, flare and itches were remitted. |

Accordingly, it was shown that B ring of the present invention has a skin moisturizing effect and is capable of improving skin texture, and that it is also effective in improving skin, for instance in lightening (spots, dullness) and anti-aging (flabbiness, resilience, large wrinkles) as well as in improving mucosal condition such as roughened lips.

In all subjects, a remarkable improving effect in skin and its persistence was observed at the site where B ring gel formulation had been applied as compared to where BNP gel formulation had been applied. Specifically, effects as follows were observed at the site where B ring gel formulation had been applied as compared to where BNP gel formulation had been applied with significance: effects of improving skin, moisturizing skin, improving skin texture, providing skin with resilience and firmness, softening skin, suppressing skin desiccation, fading fine wrinkles, supplying and keeping skin with water and oil, shallowing and diminishing crow's feet, eliminating skin rawness, eliminating and suppressing itches, relieving skin roughness and maintaining skin condition healthy.

Particularly, in subjects in their 20's or 30's, remarkable effects such as improving or eliminating wrinkles, improving cheek flabbiness, and supplying and keeping skin with moisture, water and oil, and the effects such as giving skin firmness and tightness, lifting up cheeks, eliminating skin rawness and relieving skin roughness were observed at the site where B ring gel formulation had been applied as compared to the site where BNP gel formulation had been applied, and these effects were greater as compared to those at BNP gel-applied site.

Moreover, in subjects in their 40's and 50's, remarkable effects such as improving flabbiness, large wrinkles and desiccation, giving skin firmness, fading dullness and spots were exhibited immediately after the application of B ring gel formulation, and these effects were greater as compared to those upon applying BNP gel formulation.

The effects exhibited significantly faster in B ring gel formulation as compared to BNP gel formulation. Specifically, effects were confirmed in most cases such that wrinkles were vanished or started to vanish and faded and skin was made full and resilient. These effects lasted for at least several hours thereafter. No irritating symptoms were observed with application of B ring gel formulation.

FIG. 1 shows a photograph of the right-side face of a subject in her 60's after the application of B ring gel formulation. In this subject, effects were observed at 20 minutes after the application of B ring gel formulation such that the skin were moist, provided with moisture, complexion and softness, given firmness, improved texture, provided with resilience, and large wrinkles faded. This result was compared to BNP gel formulation as a comparative example, indicating that the cyclic peptide of the invention is not only effective on fine wrinkles but also is effective on wrinkles and flabbiness, and that it is also effective in fading spots and dullness.

4.1.2 Confirming Skin-Improving Effect (Comparing B Ring Gel Formulation to Gel Base)

In order to examine the presence or absence of the contribution by the gel base to the effects of B ring gel formulation and BNP gel formulation, three subjects were administered B ring gel formulation on their right face and the gel base on the left, and changes in skin conditions on the subject's faces were observed (Table below).

TABLE 12

| Case | Applied site: method | Pre-application symptoms | Post-application symptoms |
|---|---|---|---|
| H1 Age: 48 Sex: female | Right: B ring gel formulation Left: applied gel base | Rough, stiff and dry skin texture. | After 2 min skin was left soft. Skin was tingling. Open pores and rough skin texture were not improved. |
| H2 Age: 26 Sex: female | Right: B ring Left: applied gel base | Sensitive dry skin with roughness and tingling | 1 min after application, skin tingling sensation stopped. After 2 min, B ring-applied side was felt more moisturized. 1 min after application, skin was still tingling. After 2 min, the subject left that moisturizing effect is weak. |
| H3 Age: 30 Sex: female | Right: Left: applied gel base | Sensitive skin with tingling. | Skin was tingling and temporarily red. Skin desiccation was not improved. White scales were observed. |

The B ring gel formulation was applied to normal subjects who had symptoms of roughened lips, and changes in mucosal condition were observed (Table below). The changes in mucosal conditions were determined based on physical sensory evaluation by the subject and our objective observation as physicians.

TABLE 13

| Case | Applied site: method | Pre-application symptoms | Pos-application symptoms |
|---|---|---|---|
| I1 Age: 20's Sex: female | B ring 1 µmol 1 application | Cracks on mouth corner with pain. Desiccation and wrinkles of lips. | Skin became moisturized soon after application. After 2 min, cracks on mouth corner were remitted. After 5 min, lips were soft and no longer felt dry or tingling. |
| I2 Age: 30's Sex: female | B ring 0.5 µmol 1 application | Annoying lip desiccation. | 3 min after application, lips became moisturized. |
| I4 Age: 30's Sex: female | B ring 2 µmol 1 application | Annoying lip desiccation. | After 2 min, lips were full and soft, and wrinkles were less prominent. Moisturized. |
| I3 Age: 30's Sex: female | B ring 2 µmol 1 application | Lips were dry and tingling, with wrinkles and scales | After 2 min, lips were full, soft and moisturized, and wrinkles were less prominent. Tingling sensation stopped. |
| I4 Age: 20's Sex: male | Right: B ring 1 µmol 1 application Left: gel base 1 application | Cracks on mouth corner with pain. Dry and roughened lips | 2 min after application, cracks on mouth corner were remitted with no more pain, and moisturized. 2 min after application, cracks on mouth corner and pain were not improved |

Accordingly, it was confirmed that the cyclic peptide of the invention has an activity of improving mucosal condition and it also has an immediate effect in such activity.

4.3 Observation on scalp/hair condition upon application of B ring gel formulation.

The B ring gel formulation was applied to normal subjects who had symptoms of scalp/hair, and changes in conditions of scalp and hair were observed (Table below). The changes in scalp/hair were determined based on physical sensory evaluation by the subject and our objective observation as physicians.

TABLE 14

| Case | Applied site: method | Pre-application symptoms | Post-application symptoms |
|---|---|---|---|
| J1 Age: 40's Sex: male | B ring 0.5 μmol 1 application | Presented with desiccation and itches of head. | After 2 min. itches were removed, scalp was relieved from roughness and desiccation and moisturized. After that scalp was prevented from desiccation and kept moisturized. |
| J2 Age: 50's Sex: female | B ring 1 μmol 1 application/day, 3 weeks | Presented with erythema and itch of head, and thinning and falling of hair. | Hair growth was stimulated, and an increase in hair volume was observed, and thinning of hair was improved. Hair was provided with moisture, flexibility and radiance. |
| J3 Age: 40's Sex: female | B ring 1 μmol 1 application/day, 5 days | Presented with thinning and falling of hair. | A decrease in falling hair was observed, showing an effect of preventing alopecia. Hair growth was stimulated, and an increase in hair volume was observed, and thinning of hair started to be improved. Hair was provided with moisture, flexibility and radiance. |
| J4 Age: 40's Sex: female | B ring 2 μmol 1 application | Presented with seborrheic dandruff and itches. | After 2 min, itches were removed, scalp seborrhea and dandruff started to be improved. After that scalp became and was kept clean. |
| J5 Age: 20's Sex: male | B ring 2 μmol 1 application | Presented with desiccation, mild erythema and itches. | After 1 min. itches were removed. After 2 min, scalp seborrhea and dandruff started to be improved. After 4 min, erythema and skin roughness of scalp was improved. After that skin roughness was prevented. |
| J6 Age: 60's Sex: male | B ring 2 μmol 1 application | Presented with scalp seborrhea, dandruff and itches. | After 2 min, itches were removed, scalp seborrhea was improved. After that dandruff was removed, scalp became healthy and clean. |
| J7 Age: 30's Sex: female | B ring 1 μmol To decalvant site on head and brows of subject: 1 application/day post partum, continued | From the beginning of 5th month of 3rd pregnancy, significant hair loss in eyebrows, lashes and scalp occurred, loosing almost all hair. | Upon being applied to alopecia 5 month post partum, an effect was exhibited on hair loss in eyebrows and head where hair growth was stimulated, improving thinning of hair. |

Accordingly, BNP cyclic peptide of the present invention can provide and keep scalp and hair with moisture, give them moderate water and oil, improve and prevent desiccation, and clean scalp and hair. It is further effective for suppressing itch and dandruff of scalp and also effective for preventing thinning or loosing hair, for growing hair and promoting or stimulating hair growth, and forcing hair growth, and furthermore effective for an improvement in alopecia after illness or postnatal alopecia.

4.4 Observation on Skin Condition Upon Using Bath Agent Comprising B Ring

Subjects were given bath in 37 to 41° C. hot water comprising B ring dissolved at 0.01 μM (100 ml of 20 μM B ring solution dissolved in 200 L hot water) once a day for 14 days, and skin condition of the subjects was compared to the case of hot water alone (Table 14). The changes in skin conditions were determined based on physical sensory evaluation by the subject and our objective observation as physicians.

TABLE 15

| Case | Treatment | Pre-application symptoms (miliaria, cracks, chaps and eczema) | Post-application symptoms | Changes in subjective symptoms |
|---|---|---|---|---|
| K1 Age: 30's Sex: female | B ring addition | Eczema | Gradual remission of erythema and skin desiccation. | Itches after bath was remitted. Skin was moisturized. |
| K2 Age: 30's Sex: female | Hot water | Eczema | Flare and desiccation exacerbated | Enhanced itches and desiccation after bath. |
| K3 Age: 30's Sex: female | BNP addition | Eczema | No remission of skin desiccation or erythema. | No subjective remission of skin desiccation at this concentration. |
| K4 Age: 60's Sex: female | B ring addition | Chaps, rough skin of hands, itches with tingling | Remission of desiccatinn. | Remission of itch and pain. Skin became smooth. |

TABLE 15-continued

| Case | Treatment | Pre-application symptoms (miliaria, cracks, chaps and eczema) | Post-application symptoms | Changes in subjective symptoms |
|---|---|---|---|---|
| K5 Age: 60's Sex: female | Hot water | Chaps and rough skin of hands | Exacerbation of desiccation. | Exacerbation of itches and tingling after some time after bath. |
| K6 Age: 20's Sex: male | B ring addition | Millaria and itches | Remission of flare and milaria. | Remission of itches and improvement in skin texture. |
| K7 Age: 20's Sex: male | Hot water | Miliorio and itches | No improvement in miliara. | No remission of itches. |
| K8 Age: 40's Sex: female | B ring addition | Cracks and pain on sole | Cracks gradually became shallower and improved upon application. | Relief of pain. Skin was moisturized. |
| K9 Age: 40's Sex: female | Hot water | Cracks and pain on sole | No improvement in cracks. | No remission of pain. |

Accordingly, it was confirmed that the bath agent comprising B ring of the present invention has an ameliorating effect on miliaria, cracked or chapped skin, and also an improving effect on eczema. Furthermore, it was shown to improve desiccation, pain and itch of the skin, indicating that it is effective for improvement of skin condition.

Observation on conditions of scalp and hair or skin upon using hair cosmetics (shampoo, rinse) or body soap comprising B ring 4.5.1 A shampoo comprising B ring was mixed and prepared in composition as follows.

TABLE 16

|   | Name of ingredient (tradename) | Content (%) |
|---|---|---|
| A | Sodium cocoylmethyltaurine solution (NIKKOL CMT-30) | 10.0 |
|   | Sodium laureth lactate (NIKKOL SBL-2N-27) | 20.0 |
|   | Lauryl betaine solution (NIKKOL AM-301) | 10.0 |
|   | Cocamide DEA | 4.0 |
|   | Antiseptic | q.l. |
| B | Citric acid | 0.1 |
|   | Propylene glycol | 2.0 |
|   | Guar hydroxypropyl trimonium chloride | 0.5 |
|   | Water to fill up | 100.0 |
| C | Water, B ring (B ring concentration 1 μM) | 1 mL |

A and B were dissolved with heat at 70° C. To A, B was added, stirred and mixed. C was added at 40 to 35° C. while being further stirred, and allowed to cool to room temperature as kept being stirred.

4.5.2 A Conditioner Comprising B Ring was Mixed and Prepared in Composition as Follows.

TABLE 17

|   | Name of ingredient (tradename) | Content (%) |
|---|---|---|
| A | Pentylene glycol | 1.50 |
|   | BG | 3.50 |
|   | Glycerin | 1.00 |
|   | Methyl paraben | 0.20 |
|   | Carbomer | 0.20 |
|   | EDTA-2Na | 0.10 |
|   | Water to fill up | 100.0 |
| B | Composite emulsifier (NIKKOL Nikkomulese LC) | 4.00 |
|   | Methyl heptyl laurate | 3.50 |
|   | Squalane | 0.50 |
|   | Cetearyl alcohol | 1.50 |
|   | Macadamia nut oil | 0.50 |

TABLE 17-continued

|   | Name of ingredient (tradename) | Content (%) |
|---|---|---|
|   | Avocado oil | 0.50 |
|   | Shea oil | 0.50 |
|   | Propyl paraben | 0.10 |
| C | Water, B ring (B ring concentration 1 μM) | 1 mL |

A and B were dissolved with heat at 80° C. Then A was stirred by a homomixer while B was gradually added thereto, and the mixture was emulsified. C was further added to the mixture, and the mixture was allowed to cool to 35° C. as kept being stirred.

4.5.3 A body soap comprising B ring was mixed and prepared in composition as follows.

TABLE 18

|   | Name of ingredient (tradename) | Content (%) |
|---|---|---|
| A | Cocoyl glutamic acid TEA solution | 30.0 |
|   | Sodium trideceth-4 carboxylate (KIKKOL ECTD-3 NEX) | 5.0 |
|   | Sodium cocoamphoacetate solution (KIKKOL AM-101) | 10.0 |
|   | PEG-50 hydrogenated castor oil (KIKKOL HCO-50) | 0.5 |
|   | 1,3-butylene glycol | 5.0 |
|   | Antiseptic | q.l. |
| B | EDTA-2Na | q.l. |
|   | Water to fill up | 100.0 |
| C | Water, B ring (B ring concentration 1 μM) | 1 mL |

A and B were dissolved with heat at 80° C. Then B was added to A while being stirred. C was further added to the mixture at 40 to 35° C. while kept being stirred, and the mixture was allowed to cool to room temperature as kept being stirred.

Subjects used shampoo, rinse or body soap prepared as above once a day for 14 days, and resulted conditions of scalp and hair or skin of the subjects were assessed (Table below). Changes in skin condition was assessed by dandruff of scalp. Changes in erythema was assessed by visual observation by the subject. Itches, moisturized feeling, combing, glow, resilience and elasticity of hair were assessed by subject's physical sensory evaluation.

TABLE 19

| Case | Treatment | Pre-application symptoms | Post-application symptoms | Subjective changes |
| --- | --- | --- | --- | --- |
| L1<br>Age: 60's<br>Sex: male | shampoo/<br>treatment | Presented with erythema and itches on scalp, and thinning and falling hair. | Remission of scalp erythema and a decrease in hair falling. | Improvement in itches. Hair was moisturized and provided with resilience, radiance and elasticity. |
| L2<br>Age: 20's<br>Sex: female | shampoo | Presented with desiccation and dandruff on scalp accompanied with itches | Improvement in dandruff and desiccation of scalp. | Improvement in itches. Hair was moisturized and provided with resilience, radiance and elasticity. Improved. With better combing. |
| L3<br>Age: 60's<br>Sex: female | body soap | Dry and sensitive skin. | Improvement in dry skin, relief of itching after bath. | improvement in itches after bath. |
| L4<br>Age: 60's<br>Sex: female | body soap | Dry and sensitive skin. | Improvement in dry skin, relief of itching after bath. | Improvement in itches after bath. |
| L5<br>Age: 20's<br>Sex: male | body soap | Dry skin. | Improvement in dry skin. | Skin was moisturized after bath. |

Accordingly, the use of the hair agent comprising B ring of the present invention had an fast-acting improving effect on itch, erythema and desiccation of scalp. Moreover, it was shown to be effective in improving symptoms of thinning and falling hair when it was used continuously for at least 2 weeks. Furthermore, it was shown that the use of the body soap comprising B ring of the present invention has an improving effect on dry or sensitive skin.

5. Confirming Therapeutic Effect on Alopecia

Either B ring gel formulation or BNP gel formulation was applied, and their effects on symptoms associated to various alopecia were observed (Table below). The changes in symptoms were determined based on physical sensory evaluation by the subject and our objective observation as physicians.

TABLE 20

| Case | Treatmment | Disease | Post-application symptoms |
| --- | --- | --- | --- |
| A21<br>Sex: male<br>Age: 50's | Right: B ring 1 μmol<br>1 application/day, continued.<br>Left: BNP gel formulation<br>1 application/day, continued. | Male alopecia | 7 weeks after application, hair became elastic and thick, a drastic decrease in hair-falling. Consequently, hair became dense and thinning less prominent. B ring-containing gel formulation exhibited more remarkable hair-growing affect. |
| A5<br>Sex: male<br>Age: 50's | B ring gel formulation<br>1 application/day onto head decalvant site, continued. | Male alopocia and alopocio pityroides accompanied with dandruff. Previous use of minoxidil-containing drug caused strong intation, itches and erythema to the subject and its use was terminated. | 2 weeks after starting applying B gel formulation, the existing soft air in parictal area became thicker and longer and turnec black . . . Hair got resilient and elastic. Newly grown terminal hairs remarkably decreases thinning area. Dandruff was suppressed overall, particularly in parietal area. Pruritus was eliminated. |
| A22<br>Sex: female<br>Age: 40's | B ring gel formulation<br>2 application/day onto parietal decalvant site. | Seborrheic alopecia accompanied with dandruff. | 2 weeks after application, thinning of hair was improved, exhibiting no more showing-through of scalp confirming hair-growing stimulation. Dandruff stopped, scalp seborrhea was improved and pruritus was removed. Furthermore, scap and skin became clean. |

TABLE 21

| A10<br>Sex: male<br>Age: 20's | B ring gel formulation<br>0.5 μmol<br>BNP gel formulation<br>0.5 μmol | Alopecia universalis.<br>Alopecia on whole head.<br>Previous therapy with carpronium chloride and steroid pulse first exerted hair growth-stimulating effect, but caused complete hair loss after 1 month. | 2 weeks after starting application, on both sides of head, regeneration of pores and growth of terminal hair were confirmed, which were more remarkable and hair growth area was wider on the B ring gel formulation-applied right side. Hair growth area kept increasing to the whole head. The density, elongation rate and thickness of hair were greater on the B ring gel formulation-applied right side. Upon increasing the concentration of application to 1 μmol, rate of growth and elongation were increased. |
| --- | --- | --- | --- |
| A11<br>Sex: female<br>Age: 40's | Right side of head decalvant site: B ring gel formulation<br>1 application/day for 1 week.<br>1 or 2 applications/week for 1 year thereafter.<br>Left side of head decalvant | Ophiasis and multiple alopecia. | Right forehead ophiasis site: 7 days after starting applying B ring gel formulation, a hair growth stimulation effect was observed and hair became thicker terminal hair, hair-growing area kept increasing.<br>Left BNP gel formulation-applied site: few soft hair observed, whose growth was slow and in obviously smaller area. |

TABLE 21-continued

| | |
|---|---|
| site: BNP gel formulation 1 application/day for 1 week. 1 or 2 applications/week for 1 year thereafter. | After continuing 1 or 2 applications/week for 1 year: Right forehead B ring gel formulation-applied site: hair-growing area kept increasing and hair elongation rate was fast (FIG. 2). Left BNP gel formulation-applied site: hair growth was observed though its area was smaller as compared to the right side, and majority of hairs was thin and soft (FIG. 2). |

TABLE 22

| | | | |
|---|---|---|---|
| A12 Sex: female Age: 20's | Head decalvant site: B ring gel formulation 1 application/day, continued. | Alopecia areata | 1 week after application, remarkable stimulation and growth of terminal hair was observed. |
| A12 Sex: female Age: 30's | Subject's head decalvant site: B ring gel formulation 1 application/day, continued. | Alopecia areata | 1 week after application, remarkable stimulation, growth and elongation of terminal hair was observed. |
| A24 Sex: female Age: 50's | Right half of head decalvant site: B ring gel formulation (1 μmol), 2 applications/ day for 2 weeks Left half of head decalvant site: BNP gel formulation (1 μmol), 2 applications/ day for 2 weeks | Drug-induced alopecia | Pre-application: 1 month after termination of anticancer agent therapy. Bilateral severe diffuse alopecia on whole head. Thinning of hair on whole head. Hair was short and thin, mostly white. 1 day after application at B ring-applied site, subjective hair elongation and growth stimulation were observed, and grown hairs were predominantly black (non-white). After 2 weeks, hair growth was observed at both sides. Hair were elongated with less falling hairs. Hair elongation rate is faster on B ring-applied site. Hairs are also thicker and denser, and contain more non-white hairs as compared to BNP-applied site. 3 weeks after application, remarkable growth of terminal hairs was observed. |

5.2 Case Summary

In the cases of the subjects having female pattern alopecia, male pattern alopecia, alopecia universalis, ophiasis or alopecia areata *multilocularis* as described above, a significant decrease in falling hair was observed, and the area of terminal hair growth was expanded, and the growth of the terminal hair was also faster, when B ring gel formulation of the working example was applied compared with BNP gel formulation as a comparative control (See, FIG. 2). Addingly, the existing hairs obtained resilience and their elasticity was increased. In all cases, symptoms were significantly improved as compared to the cases when BNP gel formulation of the comparative example was applied. Accordingly, B ring gel formulation had superior effects on the symptoms described above as compared to BNP gel formulation.

In addition, the B ring gel formulation could improve seborrhea, clean scalp and suppress dandruff. It also prevents hairs from turning white, grows black hairs, and improves thinning of hair. Moreover, it exhibits an antipruritic effect within 10 minutes, demonstrating an excellent immediate effect. It could suppress ithes within 3 minutes after application in some cases.

6. Confirming Therapeutic Effect on Rhinitis 6.1 Cases

Either ring nasal drop, BNP gel nasal drop was sprayed, and their effects on rhinitis in the subject was observed (Table 17). The changes in symptoms were determined based on physical sensory evaluation by the subject and our objective observation as physicians.

TABLE 23

| Case | Treatment | Disease | Post-application symptoms (severity) |
|---|---|---|---|
| R1 Sex: female Age: 20's | Right nasal cavity: B ring nasal formulation 0.1 ml, 1 spray Left nasal cavity: BNP nasal formulation 0.1 ml, 1 spray | Perennial chronic rhinitis and rhinorrhea. 20 or more blow/day | Right nasal cavity (B ring nasal drop-treated side): Subject felt breath goes through right nasal cavity soon after application. After 30 sec, air goes through nasal cavity. After 2 min. nose was clear and the subject could breathe comfortably. After 3 min, felt fresh and retained nasal discharge was removed. No discharge by blowing. A day after application, no discharge from right nasal cavity. Left nasal cavity (BNP nasal drop-treated side): 3 min after application, the discharge still retained in nasal cavity and drained by blowing. A day after application, mild nasal obstruction and rhinorrhea symptoms in left nasal cavity with small amount of retained discharge. |
| R2 Sex: female Age: 30's | Right nasal cavity: B ring nasal formulation 0.1 ml, 1 spray Left nasal cavity: BNP nasal formulation 0.1 ml, 1 spray | Rhinitis with severe nasal obstruction and feeling heavy. Right nasal cavity has severer obstruction symptom. The subject feels dry and tingling by steroid nasal drops. | Right nasal cavity (B ring nasal drop-treated side): Subject felt breath goes through right nasal cavity soon after application. After 30 sec, obstruction was improved, subject's suffering in breathing was reduced in right nasal cavity. After 1.5 min, suffering in breathing was removed in right nasal cavity and breath went though. A day after application, still no obstruction or rhinorrhea. Ths subject felt no irritation upon treatment in right nasal cavity Left nasal cavity (BNP nasal drop-treated side): 30 sec after application, obstruction of left nasal cavity was slightly improved, though the subject did not feel breath goes through as in the right cavity. A day after application, obstruction or rhinorrhea in left nasal cavity were removed. The subject felt mild dryness in left nasal cavity. |

TABLE 23-continued

| Case | Treatment | Disease | Post-application symptoms (severity) |
| --- | --- | --- | --- |
| R3 Sex: female Age: 20's | Right nasal cavity: B ring nasal formulation 0.1 ml, 1 spray | Perennial allergic rhinitis with rhinorrhea and nasal obstruction. Right nasal cavity has severer obstruction with retention of nasal discharge. | Right nasal cavity: Subject felt breath goes through nasal cavity 1 min after application. After 3 min nasal obstruction was improved, the subject could breathe through nose. After 5 min the subject could breathe comfortably through nose, with no nasal discharge by blowing. |

TABLE 24

| | | | |
| --- | --- | --- | --- |
| R4 Sex: female Age: 30's | Right nasal cavity: B ring nasal formulation 0.1 ml, 1 spray Left nasal cavity: BNP nasal formulation 0.1 ml, 1 spray | Chronic rhinitis with severe rhinorrhea and nasal obstruction. Application of steroid nasal drops could not improve symptoms when they were severe. | Right nasal cavity (B ring nasal drop-treated side): 1 min after treatment, nasal obstruction was improved to some extent. After 2 min, obstruction was improved, the subject could breathe through nose as usual, and rhinorrhea stopped. After 3 min, no nasal discharge from the right nasal cavity by blowing. Left nasal cavity (BNP nasal drop-treated side): 1 min after treatment, nasal discharge was retained in the left nasal cavity with no improvement in obstruction After 2 min, obstruction was improved to some extent, though discharge was retained, showing rhinorrhea symptom. After 3 min, nasal discharge was not drained by blowing from left nasal cavity due to obstruction. After 8 min, nasal discharge was drained by blowing. |
| R5 Sex: female Age: 20's | Right nasal cavity: B ring nasal formulation 0.1 ml, 1 spray Left nasal cavity: BNP nasal formulation 0.1 ml, 1 spray | Allergic rhinitis with rhinorrhea as main symptom and mild obstruction. | Right nasal cavity (B ring nasal drop-treated side): 30 sec after treatment, obstruction was improved and the subject could breathe through nose. After 2 min, the subject could easily breathe through nose. After 3 min, no nasal discharge was drained by blowing from the right nasal cavity. A day after treatment (after 26 hours), nasal discharge was controlled, and breathing was easier through the right nasal cavity as compared to the left. Left nasal cavity (BNP nasal drop-treated side): 2 min after treatment, obstruction was still observed. After 8 min, small amount of discharge was drained by blowing. A day after treatment (after 26 hours), nasal discharge was controlled. |
| R6 Sex: female Age: 20's | Right nasal cavity: B ring nasal formulation 0.1 ml, 1 spray Left nasal cavity: BNP nasal formulation 0.1 ml, 1 spray | Allergic rhinitis with both rhinorrhea and nasal obstruction having constant obstruction and severe rhinorrhea. 10-20 blow/day. Regular dose of oral anti-allergic drug did not sufficiently improve nasal obstruction and rhinorrhea. Steroid nasal spray causes mucosa pain. | Right nasal cavity (B ring nasal drop-treated side): nasal obstruction was slightly improved soon after treatment. After 1 min, the subject could easily breathe though nose. After 4 min, no nasal discharge was drained by blowing from the right nasal cavity. Nasal obstruction was resolved. After 10 min, pruritus was removed. A day after treatment (after 28 hours), no obstruction or rhinorrhea was observed. Left nasal cavity (BNP nasal drop-treated side): 1 min after treatment, nasal obstruction was not improved. After 3 min, obstruction was still not improved and rhinorrhea was observed. After 3 min, small amount of discharge was drained by blowing. After 10 min, obstruction was slightly improved but not resolved. After 2 hours, obstruction was resolved and the subject could breathe though nose. A day after treatment (after 28 hours), no obstruction or rhinorrhea was observed. |

TABLE 25

| | | | |
| --- | --- | --- | --- |
| R21 Sex: female Age: 20's | Right nasal cavity: B ring nasal formulation 0.1 ml, 1 spray | Rhinitis with continuous rhinorrhea and sneeze. Nasal discharge was drained by facing down. | Right nasal cavity (B ring nasal drop-treated side): 30 sec after treatment, the subject could easily breathe through nose. After 1 min rhinorrhea stopped. No nasal discharge by facing down. |
| R8 Sex: female Age: 20's | Right nasal cavity: B ring nasal formulation 0.1 ml, 1 spray + 1 spray 20 min later Left nasal cavity: BNP nasal formulation 0.1 ml, 1 spray + 1 spray 20 min later | Chronic allergic rhinitis (with both rhinorrhea and obstruction). The subject regularly feels nasal obstruction. Application of steroid nasal formulation causes the subject strong irritation. Accompanied with rhinorrhea and eye pruritus. | Right nasal cavity (B ring nasal drop-treated side): 1 min after treatment, obstruction was improved and the subject could easily breathe through nose. The subject felt no irritation by treatment. The effect lasts for 1 week thereafter, and rhinorrhea arid obstruction were controlled. No nasal discharge by blowing. Commercial steroid nasal formulation caused a sharp irritation and recurrence of symptoms within 2 hours. Left nasal cavity (BNP nasal drop-treated side): |
| R9 Sex: female Age: 30's | Right nasal cavity: B ring nasal formulation (1 μmol) 0.1 ml, 1 spray Left nasal cavity: | Allergic rhinitis (with rhinorrhea). The subject has rhinorrhea all day and usually blows 20 or more times a day. Application of steroid nasal formulation causes the subject | Right nasal cavity (B ring nasal drop-treated side): 2 min after treatment, the subject could breathe through nose, with no irritation in the right nasal cavity. After 4 min the subject could breathe through nose, with no nasal discharge drained. |

TABLE 25-continued

| | | |
|---|---|---|
| BNP nasal formulation (1 µmol) 0.1 ml, 1 spray | strong dry feeling on mucosae of nasal cavity and pharynx. The effect of the steroid nasal formulation lasts only 3-4 hours, and after the effect ended, sneezing and nasal discharge last for several hours and need frequent blowing. | Left nasal cavity (BNP nasal drop-treated side): 2 min after treatment, obstruction was improved and the subject could breathe through nose. After 4 min, in the left nasal cavity, the subject drained small amount of nasal discharge by blowing. In the right nasal cavity, the effect of the nasal treatment lasted for 4 hours. Blowing caused obstruction in the left nasal cavity but not in the right. The subject felt that B ring nasal formulation is much better to the steroid nasal formulation regarding the effect on the symptoms, long-lasting and fast-acting effect, lower frequency of use required, and absence of irritating symptom upon use. |

TABLE 26

| | | | |
|---|---|---|---|
| R10 Sex: male Age: 30's | Right nasal cavity: B ring nasal formulation (1 µmol) 0.1 ml, 1 spray Left nasal cavity: BNP nasal formulation (1 µmol) 0.1 ml, 1 spray | Allergic rhinitis with rhinorrhea and obstruction complicated with rhinosinusitis. Obstruction in the right nasal cavity due to rhinosinusitis is severer than the left and could not be improved by steroid nasal formulation, making the subject incapable of breathing through nose. If left untreated, nasal discharge is drained from nostrils spontaneously. | Right nasal cavity (B ring nasal drop-treated side): 2 min after nasal treatment, obstruction was improved and the subject could breathe through nose. The subject could breathe more comfortably in the right nasal cavity as compared to the left. The subject felt no irritation in the right nasal cavity. After 4 min, the subject could very easily breathe, with no nasal discharge drained by blowing. Left nasal cavity (BNP nasal drop-treated side): 4 min after nasal treatment, nasal obstruction was not resolved. Nasal discharge was decreased as compared to pre-treatment, though draining was still observed. |
| R11 Sex: male Age: 20's | Right nasal cavity: B ring nasal formulation 0.1 ml, 1 spray Left nasal cavity: BNP nasal formulation 0.1 ml, 1 spray | Perennial rhinitis with rhinorrhea and obstruction complicated with rhinosinusitis, having severe obstruction. Very high frequency of blowing. These symptoms were not improved by any previously used nasal formulation. | Right nasal cavity (B ring nasal drop-treated side): 2 min after nasal treatment, the subject could breathe through nose. After 5 min, nasal discharge stopped, enabling the subject to breathe though nose. The subject felt no obstruction and was able to breathe through nose throughout 1 week after nasal treatment. Left nasal cavity (BNP nasal drop-treated side): 5 min after nasal treatment, obstruction was not resolved, with nasal discharge present in the left nasal cavity. After 10 min. obstruction was not resolved, making the subject incapable of breathing through nose. |

6.2 Case summary

In all cases described above, both rhinorrhea and nasal obstruction were quickly improved or eliminated when B ring nasal drop of the working example had been applied as compared to the case when BNP nasal drop of comparative example had been applied. Accordingly, B ring nasal drop had faster effect than BNP nasal drop. Addingly, the effect of B ring nasal drop was more than equal to that of BNP nasal drop, and because the effect lasted for longer time period, it can suppressing recurrence of symptoms.

The following table summarizes information from the cases described above, within the range recognizable at the time when symptoms of nasal obstruction and rhinorrhea were improved.

TABLE 27

| | within 3 min | within 5 min | within 10 min | No resolution within 10 min |
|---|---|---|---|---|
| Resolution of rhinorrhea | | | | |
| B ring nasal formulation | 3 | 4 | 1 | 0 |
| BNP nasal formulation | 0 | 0 | 0 | 7 |
| Resolution of nasal obstruction | | | | |
| B ring nasal formulation | 6 | 5 | 0 | 0 |
| BNP nasal formulation | 0 | 0 | 0 | 8 |

7. Analysis of Binding State of Human BNP and Type A Receptor

The superior pharmacological effects of the B ring-compound of the invention on various diseases relative to conventional BNP has been explained so far with reference to data based on respective clinical cases. Such pharmacological effects is also supported by the result of the conformation analysis of the compound performed by the inventors, which is explained by following experimental report for reference.

In order to investigate binding state of human BNP (BNP-32) and its receptor Type A receptor (NPR-A), an in silico analysis was performed by homology modeling using conformation. Swiss-Pdb viewer and SWISS-MODEL were used for modeling.

7.1 Template Structure

Firstly, prior to the above analysis, a template structure for investigation on binding state of human BNP and Type A receptor was selected. As this template structure, the conformation of the complex of rat NPR-A and rat ANP peptide (PDB ID: 1T34) were used. Rat NPR-A is a homodimer composed of A and B strands. The conformation of such rat NPR-A has been determined by X-ray crystalline structural analysis such that 21 residues from Cys7 to Arg 27 of rat ANP were bound. The conformation of rat NPR-A was obtained from the database of protein conformation, Protein Data Bank. Amino acid homology between human NPR-A and rat NPR-A is 85%.

7.2 BNP Peptide Model

In the present study, as BNP peptide model, a resion from Cys10 to Arg30 in human BNP (BNP-32, SEQ ID NO: 13, Ser-Pro-Lys-Met-Val-Gln-Gly-Ser-Gly-Cys-Phe-Gly-Arg-Lys-Met-Asp-Arg-Ile-Ser-Ser-Ser-Ser-Gly-Le u-Gly-Cys-Lys-Val-Leu-Arg-Arg-His), i.e., an amino acid sequence (SEQ ID NO: 14, Cys-Phe-Gly-Arg-Lys-Met-Asp-Arg-Ile-Ser-Ser-Ser-Ser-Gly-Leu-Gly-Cys-Lys-Val-Leu-Arg) was used. In the peptide model above, the amino acid sequence of B ring of the invention corresponds to a resion from Cys10 to Cys26 of human BNP above, i.e., Cys-Phe-Gly-Arg-Lys-Met-Asp-Arg-Ile-Ser-Ser-Ser-Ser-Gly-Leu-Gly-Cys (SEQ ID NO: 15).

7.3 Homology Modeling

In order to speculate the amino acid residues that are involved in binding of human NPR-A and human BNP, a complex model in which BNP peptide is bound to human NPR-A was constructed by homology modeling. Specifically, human BNP peptide model was constructed based on the template structure of rat ANP peptide, and human NPR-A model structure based on the template structure of rat NPR-A.

Next, residues that are involved in the interaction was speculated from the amino acid residues detected between human BNP peptide model and human NPR-A.

The results showed that BNP peptide model is bound to human NPR-A dimer being sandwiched between the A strand and B strand. Amino acids in the amino acid sequence, e.g., the amino acid sequence used as the model (SEQ ID NO: 14, Cys-Phe-Gly-Arg-Lys-Met-Asp-Arg-Ile-Ser-Ser-Ser-Ser-Gly-Leu-Gly-Cys-Lys-Val-Leu-Arg) are expressed as "amino acid (number)". Namely, the number in parentheses denotes the relative position counted from the N-terminal of the amino acid sequence, for example, Phe2 indicates an amino acid that is the second Phe counted from the N-terminal of the peptide model.

In the constructed complex model, the presence of a hydrophobic bond by Phe2 side chain, a hydrogen bond by Phe2 main chain, and hydrogen bonds by side chains of Arg4, Met6, Arg8, Ser10 and Ser11 were speculated between BNP peptide model and the A strand of NPR-A. Phe2, Arg4, Met6, Arg8, Ser10 and Ser11 in BNP peptide model correspond to Phe11, Arg13, Met15, Arg17, Ser19 and Ser20 in human BNP respectively. Namely, this result suggests that these amino acid residues in human BNP is likely to be the residues that contribute to NPR-A activation.

7.4 Discussion

Thus, by in silico conformation analysis, it was speculated that, in human BNP, the amino acid residues that are present in its cyclic part are likely to contribute to NPR-A activation, whereas the amino acid residues present in the tail part are not. It was also suggested that BNP cyclic structure is a smaller molecule than BNP-32 and therefore capable of binding easily and quickly. In fact, a clinical application of a peptide having BNP cyclic structure confirmed that BNP cyclic structure provides faster therapeutic effect than BNP-32. This clinical result is consistent with that of the in silico analysis that BNP cyclic structure contributes to NPR-A activation and can bind to it more easily and quickly than BNP-32. Thus, BNP cyclic structure has a superior therapeutic effect than a general BNP peptide, and therefore is a different substance.

On the other hand, an NMR analysis revealed that ANP does not take any particular conformation in a solution where its conformation greatly wobbles; this is considered to be similar for BNP. Namely, in human BNP, assuming that the amino acid residues in the cyclic part contribute to its binding to human NPR-A, it is speculated that the amino acid residues in the tail part rather prevent human BNP from entering into the narrow BNP binding site sandwiched between A and B strands of human NPR-A due to its large wobbling. Therefore, it is considered that the cyclic part of human BNP is a relatively smaller molecule than conventionally known human BNP, enabling itself to enter into BNP binding site of NPR-A more easily and quickly. Moreover, it is speculated that the cyclic part of human BNP has a higher affinity to human NPR-A than BNP-32. This supports the clinical outcomes described herein that the peptide having only the cyclic part of BNP exhibits therapeutic effect faster than BNP-32.

In order to speculate the effect of BNP cyclic structure (B ring) from non-human species on human Type A receptor, complex models of human NPR-A and BNP rings from pig, bird or rat were generated to surmise interaction. The results suggested that a sufficient effect of the invention can be expected by using BNP ring from non-human animal species (e.g., pigs, birds or rats), as long as it shows an affinity to human NPR-A.

8. Speculating Replaceable Amino Acid Residues in BNP Cyclic Moiety

Using the constructed model structure of the complex, replaceablity of amino acid residues other than those considered to be involved in the interaction was investigated.

Specifically, in order to investigate whether the peptide in which amino acid residue that is not assumed to be involved in the interaction has been replaced with another amino acid is capable of binding to NPR-A, a mutant model of BNP was generated to analyze the interaction. Swiss-Pdb viewer was used for modeling.

Specifically, amino acid residues Gly12, Lys14, Asp16, Ile18, Ser21, Ser22, Gly23, Leu24 and Gly25 in human BNP were targeted for the investigation on their replaceability with other amino acids in terms of following points:

- No steric hindrance caused by binding to NPR-A. No interatomic collision observed in the model structure of NPR-A and BNP.
- No influence on electrostatic potential on surface.
- No large increase in intramolecular energy value (no unnatural angle or twist caused in intermolecular binding).
- No non-naturally occurring hydrogen bond formed between the strands of NPR-A and BNP and within BNP strand.
- No cavity (cavity, niche) formation.

Among those described above, intramolecular energy was calculated by ComputeEnergy command of Swiss-Pdb viewer. Intramolecular energy was calculated from the sum of the length of binding, bond angle, twist and binding energy, etc. in the unit kilojoule/mol (Kj/mol).

The results of analysis indicated the presence of replaceable amino acid residues in Gly12, Lys14, Ile18, Ser21, Ser22, Leu24 and Gly25 among the amino acid residues of human BNP (Table below).

TABLE 28

| human BNP | Replaceable amino acid |
|---|---|
| Gly12 | Ala, Val, Ser, Thr |
| Lys14 | Arg |
| Asp16 | none |
| Ile18 | Val |
| Ser21 | Thr, Ala, Val, Gln, Leu, Ile, Met |
| Ser22 | Thr, Ala, Val |
| Gly23 | none |
| Leu24 | Ala, Val, Ile, Met |
| Gly25 | Ala, Ser |

Accordingly, even when the replacement of the amino acid corresponding to those described in the table above took place in the cyclic part of human BNP, i.e., the peptide expressed by the Formula I-a, it was suggested that the peptide replaced in such a way exerts a similar effect as the peptide composed of the amino acid sequence expressed by Formula I-a.

9. Confirming Therapeutic Effect of the Cyclic Peptide with Amino Acid Replacement Next, cyclic peptides with some replaced amino acid were subjected to following examination in order to confirm their effect. The methods for preparing the above cyclic peptide and confirming amino acid sequence of the prepared peptide were same as the method for preparing the cyclic peptide as described above and Mass spectroscopy method.

9.1 Confirming Effects on Scalp or Hair

The obtained cyclic peptide was prepared in purified water at 3, 15, 30, 100 or 500 μg/ml and applied to the affected site. Each of formulations A to E in the table indicates the concentration of cyclic peptide at 3, 15, 30, 100 or 500 pig/ml, respectively. The absence of the effect upon the application of purified water confirmed the effect was not a placebo effect.

TABLE 29

| SEQ ID NO (amino acid sequence) of the cyclic peptide used | ID Sex | Age | Cases | Formulation | Treatment | Diagnostic impression of hair and scalp after application |
|---|---|---|---|---|---|---|
| SEQ ID NO 16: (CFVRKMDRISSSSGLGC) | S1 male | 50's | multiple alopecia areata | C | once a day | After 1 day, fluffy hairs started to grow. After 3 days, obviously Hair started to grow, restoration and elongation were observed. Hair gained elasticity and resilience, thickened. Hair root regeneration confirmed. |
| | S2 female | 40's | seborrheic dermatitis male AGA | C | once a day | Iches were remitted immediately after applicaation. After 3 minutes, seborrhea and erythema remitted. After 1 day, dandruff, redness and seborrhea of scalp improved, falling hairs reduced. After 7 days, hairs stimulated to grow, restored hair and hair growth confirmed. |
| | S3 female | 50's | female AGA | C | once a day | After 1 day, hair gained elasticity, resilience and increased volume. |
| | S4 female | 50's | hair thinning after anticancer agent therapy | C | once a day | After 5 days, hair stimulation and growth confirmed. Hair became dense and thick. |
| | S5 female | 20's | multiple alopecia areata | C | once a day | Iches were improved immediately after application. After 1 day, fluffy hairs started to grow. After 3 days, obviously Hair growth stimulated and restored elongation of hair observed, hair gained elasticity and resilience, thickened. Hair root regeneration observed. |
| | S6 female | 60's | healthy skin (scalp) | C | once a day | After 1 day, hair became fuller with increased volume. Hair gained elasticity and resilience. After 7 days, grown hairs were predominantly black over white hairs. White hairs turned black. |
| SEQ ID NO 17: (CFGQKMDRISSSGLGC) | S7 male | 40's | multiple alopecia areata | B | once a day | After 3 days, remarkable terminal hair growth was observed. |
| | S8 female | 20's | multiple alopecia areata | B | once a day | After 5 days, newly born hair roots and grown hairs were observed. |
| | S9 male | 30's | male AGA | B | once a day | After 2 or 3 days, hair gained elasticity and resilience. After 7 days, hair gained volume, restoration was confirmed. |

TABLE 29-continued

| SEQ ID NO (amino acid sequence) of the cyclic peptide used | ID | Sex | Age | Cases | Formulation | Treatment | Diagnostic impression of hair and scalp after application |
|---|---|---|---|---|---|---|---|
| | S10 | female | 30's | female alopecia | C | once a day | Hair gained elasticity and resilience, hair volume was increased on the night of first application. After 5 days, appearance of scalp through hair were improved. The effect lasted for 1 week after stopping application. |
| SEQ ID NO 18: (CFGHKMDRISSS SGLGC) | S11 | male | 60's | male alopecia | B | once a day | After 1 week, hair gained thickness and elasticity, hair density was increased. |
| | S12 | male | 70's | healthy skin (scalp) | C | once a day | After 1 day, hair became fuller with increased volume. Hair gained elasticity and resilience. After 7 days, grown hairs were predominantly black over white hairs. White hairs turned black. |
| | S13 | female | 40's | alopecia areata | B | once a day | After 5 days, hair started to grow, elongation and growth of hair were observed. |
| | S14 | female | 60's | alopecia areata | B | once a day | After 5 days, hair started to grow, hair density was increased. |
| SEQ ID NO 19: (CFGRRMDRISSS SGLGC) | S15 | female | 20's | multiple alopecia areata | B | once a day | After 5 days, hair started to grow, elongation and restoration of hair were observed. |
| | S16 | female | 50's | hair thinning after anticancer agent therapy | C | once a day | After 2 days, hair gained elasticity and resilience volume of hair increased |
| | S17 | male | 60's | male AGA | C | once a day | After 1 day, hair gained elasticity, resilience and increased volume. Hair started to grow, restoration and elongation were observed |
| | S18 | female | 40's | female alopecia | D | once a day | After 3 days, scalp shown through hair due to thinning got obscure. Reduced falling hairs. |
| | S19 | female | 40's | scalp seborrheic dermatitis | C | once a day | After 3 days, seborrhea and erythema were improved, so was dandruff. |
| SEQ ID NO 20: (CFGRKLDRISSS SGLGC) | S20 | male | 50's | male AGA | C | once a day | After 1 day, hair gained elasticity, resilience and increased volume. |
| | S21 | male | 40's | multiple alopecia areata | C | once a day | After 3 days, hair density was increased. Hair started to grow and grew. |
| SEQ ID NO 21: (CFGRKIDRISSS SGLGC) | S22 | male | 40's | multiple alopecia areata | C | once a day | After 3 days, hair started to grow at the site of alopecia areata and grew. |
| | S23 | male | 40's | male alopecia | C | 1 application/day on parietal male thinning area | After 3 days, hair started to gain resilience, felt thick. After 7 days, parietal thinning were improved and hair volume started to increase. |
| | S24 | female | 40's | female AGA | C | once a day | After 1 day, hair gained elasticity, resilience and increased volume. Hair started to grow, restoration and elongation were observed. |
| | S25 | female | 30's | multiple alopecia areata | C | once a day | After 1 day, hair started to grow. After 2 weeks, obvious lots of hairs started to grow, restoration, elongation and growth were observed. |
| | S26 | female | 10's | multiple ophiasis | C | once a day | After 2 days, stimulated hair growth was confirmed. After 7 days, obvious stimulated hair growth was observed, elongated and grown hair was also observed. |

TABLE 29-continued

| SEQ ID NO (amino acid sequence) of the cyclic peptide used | ID | Sex | Age | Cases | Formulation | Treatment | Diagnostic impression of hair and scalp after application |
|---|---|---|---|---|---|---|---|
| SEQ ID NO 22: (CFGRKMDRVSSS SGLGC) | S27 | male | 40's | male AGA | B | 1 application/day on forehead thinning area | After 2 or 3 days, hair gained elasticity and resilience. After 7 days, hair gained volume, restoration was confirmed. |
| | S28 | male | 20's | multiple alopecia areata | C | once a day | After 3 days, hair started grow and grew. |
| | S29 | female | 60's | female AGA | C | once a day | After 1 day, hair gained elasticity, resilience and increased volume. |
| | S30 | female | 70's | female alopecia | C | once a day | After 7 days, increased hair volume. Appearance of scalp shown through hair got obsecure. |
| | S31 | female | 20's | ophiasis | B | once a day | After 5 days, stimulated hair confirmed along intractable hairline, and elongation of hair observed. |
| | S32 | female | 30's | multiple alopecia areata | C | once a day | After 1 day, hair started to grow. After 6 weeks, obvious stimulated hair growth, elongation and growth of hair were observed |
| SEQ ID NO 23: (CFGRKMDRIGSS SGLGC) | S33 | male | 30's | alopecia areata universalis | C | once a day | After 3 days, stimulated and elongated hairs were observed |
| | S34 | female | 60's | hair thinning after anticancer agent therapy | C | once a day | After 1 day, hair gained elasticity and resilience. |
| | S35 | female | 50's | female AGA | C | once a day | After 1 day, hair gained elasticity, resilience and increased volume. Hair started to grow, restoration and elongation were observed. |
| | S36 | female | 40's | female alopecia | B | 1 application/day on parietal and forehead thinning area | After 5 days, hair gained elasticity, resilience and increased volume. Appearance of scalp shown through hair got obsecure. |
| | S37 | male | 60's | multiple alopecia areata | C | once a day | After 1 day, stimulated hair was observed. After 3 days, application was stoped, but stimulation and elongation of hair contined. White hairs turned black again, black hairs started to grow. |
| | S38 | female | 40's | female alopecia seborrheic dermatitis | B | once a day | After 7 days, hair gained volume, appearance of scalp shown through hair got obsecure. Seborrhea of scalp was improved. |
| | S39 | female | 10's | ophiasis | B | once a day | After 4 days, regardless of highly intractable ophiasis, stimulated soft hairs were observed. |
| SEQ ID NO 24: (CFGRKMDRISAS SGLGC) | S40 | female | 10's | alopecia areata | A | once a day | After 7 days, stimulated and grown soft hairs were observed. |
| | S41 | female | 50's | female AGA | C | once a day | After 1 day, hair gained elasticity, resilience and increased volume. |
| | S42 | male | 30's | multiple alopecia areata | B | once a day | After 4 days, stimulation and elongation of hair observed. |
| | S43 | female | 30's | multiple alopecia areata | C | once a day | After 1 day, hair started to grow. A number of stimulated, elongated and grown hairs were observed in 3 weeks. |
| SEQ ID NO 25: (CFGRKMDRISSQ SGLGC) | S44 | male | 60's | multiple alopecia areata | B | once a day | After 5 days, hairs started to grow and grew. |
| | S45 | female | 50's | male AGA | C | once a day | After 1 day, hair gained elasticity, resilience and increased volume. Hair started to grow, restoration and elongation were observed. |

TABLE 29-continued

| SEQ ID NO (amino acid sequence) of the cyclic peptide used | ID | Sex | Age | Cases | Formulation | Treatment | Diagnostic impression of hair and scalp after application |
|---|---|---|---|---|---|---|---|
| | S46 | female | 60's | multiple alopecia areata | B | once a day | After 5 days, hair root regeneration and hair growth stimulation were observed. Application continued and a remarkable restoration, elongation and growth of hair were observed. Hair elongation rate was fast. |
| | S47 | female | 40's | female alopecia | C | once a day | After 1 day, hair gained elasticity and resilience. Application continued for 3 days and stopped, but hair kept elasticity and resilience. The effect lasted for 1 week. |
| SEQ ID NO 26: (CFGRKMDRISSV SGLGC) | S48 | female | 30's | female alopecia | C | once a day | After 3 days, appearance of scalp shown through hair got obsecure, hair gained elasticity, resilience and increased volume. Hairs were restored. |
| | S49 | male | 30's | male alopecia | B | once a day | After 5 days, volume of hair increased. Hair gained elasticity and resilience. |
| | S50 | female | 20's | female AGA | C | once a day | Volume of hair increased and scalp does not show through after 3 days. The effect went on |
| | S51 | female | 60's | female AGA | C | once a day | After 1 day, hair gained elasticity, resilience and increased volume. Hair started to grow, restoration and elongation were observed. |
| | S52 | male | 20's | multiple alopecia areata | C | once a day | After 3 days, stimulated hair was observed After 7 days, further stimulation and growth of hair were confirmed. |
| | S53 | female | 30's | multiple alopecia areata | C | once a day | After 1 day, hair started to grow. Terminal hairs started to grow, and restoration, elongation and growth of hair were observed in 2 weeks. |
| SEQ ID NO 27: (CFGRKMDRISSL SGLGC) | S54 | female | 50's | hair thinning after anticancer agent therapy | B | once a day | After 5 days, hair got thick and dense. |
| | S55 | male | 50's | male AGA | C | once a day | After 1 day, hair gained elasticity, resilience and increased volume. Hair started to grow, restoration and elongation were observed. |
| | S56 | male | 20's | multiple alopecia areata | E | once a day | After 3 days, hair started to grow After 7 days, stimulation and growth of hair were confirmed. |
| SEQ ID NO 28: (CFGRKMDRISSI SGLGC) | S57 | female | 40's | female AGA | C | once a day | After 1 day, hair gained elasticity, resilience and increased volume. |
| | S58 | male | 20's | multiple alopecia areata | C | once a day | After 1 day, hair falling was reduced and hair started to grow. After 7 days, remarkable stimulation, elongation and growth of hair were confirmed. |
| | S59 | male | 20's | multiple alopecia areata | C | once a day | After 1 day, hair started to grow and falling hairs reduced. After 4 days, application was stoped, but stimulation, elongation and restoration of hair persisted. |
| | S60 | female | 50's | healthy skin (scalp) | C | once a day | After 1 day, hair became fuller with increased volume. Hair gained elasticity and resilience. After 7 days, grown hairs were predominantly black over white hairs. White hairs turned black. |

TABLE 29-continued

| SEQ ID NO (amino acid sequence) of the cyclic peptide used | ID Sex | Age | Cases | Formulation | Treatment | Diagnostic impression of hair and scalp after application |
|---|---|---|---|---|---|---|
| | S61 female | 40's | multiple alopecia areata | C | once a day | After 3 days, hairs started to grow and grew. |
| | S62 female | 40's | alopecia areata | B | once a day | After 5 days, stimulated hair growth was confirmed. After 2 weeks, further growth of terminal hair, elongation and growth of hair were confirmed all over alopecia site. |
| SEQ ID NO 29: (CFGRKMDRISSM SGLGC) | S63 female | 40's | female alopecia | C | once a day | After 4 days, hair gained elasticity, resilience and increased volume. |
| | S64 male | 40's | healthy skin (scalp) | C | once a day | After 1 day, hair volume was increased. Hair gained elasticity and resilience. |
| | S65 male | 40's | male AGA | C | once a day | Hair gained resilience and volume after 3 days. Application continued for 1 week, and the effect persisted for 1.5 months thereafter. |
| | S66 male | 30's | male alopecia | C | 2 application/day for 3 days | After 3 days, hair gained elasticity, resilience and increased volume at thinning area on forehead. After a few days, hair growth stimulation and hair growth were confirmed. |
| | S67 female | 70's | female alopecia | C | once a day | After 2 days, hair gained elasticity and resilience. After 5 days, volume of hair increased. It was confirmed that the stimulated hairs are predominantly black over white hair. |
| SEQ ID NO 30: (CFGRKMDRISSS VGLGC) | S68 female | 20's | alopecia areata ophiasis | B | once a day | After 7 days, stimulated hair growth was confirmed. Even 2 weeks after stopping application, hair growth stimulation and restoration persisted, and there were little falling hairs. |
| | S69 male | 40's | male AGA | B | once a day | After 2-3 days, hair gained elasticity and resilience. After 7 days, hair gained volume, restoration was confirmed. |
| | S70 male | 30's | alopecia universalis | B | once a day | After 3 days, hairs started to grow and grew. |
| | S71 female | 30's | multiple alopecia areata | C | once a day | After 1 day, stimulated hair growth was confirmed. |
| SEQ ID NO 31: (CFGRKMDRISSS SRLGC) | S72 female | 20's | alopecia areata ophiasis | C | once a day | After 7 days, stimulated hair growth was confirmed. Even 2 weeks after stopping application, hair growth stimulation and restoration persisted, and falling hairs significantly decreased |
| | S73 male | 40's | healthy skin (scalp) | C | once a day | After 1 day, hair volume was increased. Hair gained elasticity and resilience. |
| | S74 male | 30's | alopecia areata universalis | C | 2 application/day for 3 days | After 3 days, stimulation and elongation of hair were confirmed. |
| | S75 female | 60's | multiple alopecia | B | once a day | After 5 days, hairs stimulated to grow, restored hair and hair growth were confirmed. It was confirmed that hair elongation rate is fast. |
| SEQ ID NO 32: (CFGRKMDRISSS SGMGC) | S76 male | 30's | male alopecia | B | once a day | After 7 days, hair gained elasticity. Hair started to grow, and volume of hair on parietal forehead was increased. |

TABLE 29-continued

| SEQ ID NO (amino acid sequence) of the cyclic peptide used | ID | Sex | Age | Cases | Formulation | Treatment | Diagnostic impression of hair and scalp after application |
|---|---|---|---|---|---|---|---|
| | S77 | female | 60's | female AGA | C | once a day | After 1 day, hair gained elasticity, resilience and increased volume. Hair started to grow, restoration and elongation were observed. |
| | S78 | male | 40's | alopecia universalis | C | once a day | After 3 days, hair stimulation and growth were confirmed |
| | S79 | female | 50's | hair thinning after anticancer agent therapy | C | once a day | After 2 days, hair gained elasticity, resilience and increased volume. Appearance of scalp shown through hair got obsecure. Hair increase was confirmed. |
| SEQ ID NO 33: (CFGRKMDRISSS SGIGC) | S80 | female | 50's | multiple alopecia areata | B | once a day | After 7 days, stimulated hair growth was confirmed. |
| | S81 | male | 60's | healthy skin (scalp | C | once a day | After 1 day, hair became fuller with increased volume. Hair gained elasticity and resilience. After 7 days, grown hairs were predominantly black over white hairs. White hairs turned black. |
| | S82 | female | 40's | multiple alopecia areata | B | once a day | After 5 days, hair root regeneration and hair growth stimulation were confirmed. |
| | S83 | male | 60's | alopecia areata | C | once a day | After 1 day, apparent hair growth stimulation and restoration were confirmed. After 4 days, hair elongation were confirmed. |
| SEQ ID NO 34: (CFGRKMDRISSS SGVGC) | S84 | female | 50's | hair thinning after anticancer agent therapy | B | once a day | After 5 days, thin, fuzzy hairs along hairline got thicker and denser. |
| | S85 | male | 50's | male AGA | C | once a day | After 1 day, hair gained elasticity, resilience and increased volume. Hair started to grow, restoration and elongation were observed. |
| | S86 | male | 40's | male AGA | C | once a day | Hair gained resilience and volume after 3 days. Application continued for 1 week, and the effect persisted for 1.5 months thereafter. |
| | S87 | male | 30's | male alopecia | C | once a day | After 3 days, hair gained resilience and volume of hair increased in parietal thinning area |
| | S88 | male | 20's | multiple alopecia areata | C | once a day | After 1 day, hairs started to grow and grew. |
| SEQ ID NO 35: (CFGRKMDRISSS SGAGC) | S89 | female | 40's | hair thinning after anticancer agent therapy | B | once a day | After 5 days, hair gained elasticity, resilience, thickness, and increased volume. |
| | S90 | male | 20's | multiple alopecia areata | C | once a day | After 3 days, stimulated hair growth was confirmed. |
| | S91 | female | 50's | female AGA | C | once a day | After 1 day, hair gained elasticity, resilience and increased volume. Hair started to grow, restoration and elongation were observed. |
| | S92 | female | 60's | multiple alopecia areata | B | once a day | After 5 days, hair root regeneration and hair growth stimulation were observed. Then, remarkable restoration, elongation and growth of hair were observed. |
| | S93 | female | 30's | multiple alopecia areata | C | once a day | After 1 day, stimulated hair was observed. After 2 weeks, there is remarkable elongation of hair marginal area around large decalvant spot, and new hair started to grow in center part. |

TABLE 29-continued

| SEQ ID NO (amino acid sequence) of the cyclic peptide used | ID | Sex | Age | Cases | Formulation | Treatment | Diagnostic impression of hair and scalp after application |
|---|---|---|---|---|---|---|---|
| SEQ ID NO 36: (CFGRKMDRISSS SGLSC) | S94 | male | 30's | alopecia universalis | C | once a day | After 4 days, hair stimulation and growth were confirmed. |
| | S95 | male | 40's | healthy skin (scalp) | C | once a day | After 1 day, hair volume was increased. Hair gained elasticity and resilience. |
| | S96 | male | 50's | seborrheic dermatitis | C | once a day | After 3 days, seborrhea and erythema were improved. |
| | S97 | male | 50's | male alopecia | B | once a day | After 5 days, hair gained elasticity, resilience and increased volume. |
| SEQ ID NO 37: (CFGRKMDRISSS SGLAC) | S98 | female | 40's | hair thinning after anticancer agent therapy | B | once a day | After 5 days, hair gained elasticity, resilience, thickness and increased volume. |
| | S99 | male | 40's | male AGA | B | 1 application/day on forehead thinning area | After 2 or 3 days, hair gained elasticity and resilience. After 7 days, hair gained volume, restoration was confirmed. |
| | S100 | male | 20's | multiple alopecia areata | C | once a day | After 5 days, stimulated hair growth was confirmed. |
| | S101 | female | 20's | alopecia areata | A | once a day | After 10 days, hair growth stimulation elongation were confirmed. |
| SEQ ID NO 38: (CFARKMDRISSS SGLGC) | S102 | female | 50's | female AGA | C | once a day | After 1 day, hair gained elasticity, resilience and increased volume. Hair started to grow, restoration and elongation were observed. |
| | S103 | female | 50's | dandruff, itches | C | once a day | Iches stopped in 3 minutes, dandruff was reduced, redness in scalp was significantly improved. |
| | S104 | female | 10's | eclopic multple alopecia | C | once a day | After 3 days, stimulated hair growth was confirmed in eyebrows. |
| SEQ ID NO 39: (CFSRKMDRISSS SGLGC) | S105 | male | 10's | alopecia universalis | C | once a day | After 3 days, stimulated hair growth was confirmed. |
| | S106 | female | 50's | dandruff, itches | C | once a day | Iches stopped in 1 minute, dandruff was reduced, redness in scalp was significantly improved. |
| | S107 | female | 60's | healthy skin (scalp) | C | once a day | After 1 day, hair became fuller with increased volume. Hair gained elasticity and resilience. After 7 days, grown hairs were predominantly black over white hairs. White hairs turned black. |
| | S108 | female | 60's | multiple alopecia areata | C | once a day | After 3 days, stimulated hair growth was confirmed. More black hairs started to grow than white hairs, and hair elongation rate was fast. |
| SEQ ID NO 40: (CFTRKMDRISSS SGLGC) | S109 | male | 60's | male AGA | C | once a day | After 1 day, hair gained elasticity, resilience and increased volume. Hair started to grow, restoration and elongation were observed. |
| | S110 | male | 20's | multiple alopecia areata | C | once a day | After 4 days, stimulated hair growth was confirmed |
| | | | | | C | once a day | |
| SEQ ID NO 41: (CFGRKMDRISST SGLGC) | S111 | female | 50's | female AGA | C | once a day | After 1 day, hair gained elasticity, resilience and increased volume. Hair started to grow, retoration and elongation were observed. |
| | S112 | male | 20's | multiple alopecia areata | C | once a day | After 4 days, stimulated hair growth was confirmed. |

TABLE 29-continued

| SEQ ID NO (amino acid sequence) of the cyclic peptide used | ID | Sex | Age | Cases | Formulation | Treatment | Diagnostic impression of hair and scalp after application |
|---|---|---|---|---|---|---|---|
| SEQ ID NO 42: (CFGRKMDRISSA SGLGC) | S113 | male | 30's | multiple alopecia areata | C | once a day | After 3 days, stimulated hair growth was confirmed. |
| | S114 | male | 40's | healthy skin (scalp) | C | once a day | After 1 day, hair volume was increased. Hair gained elasticity and resilience. |
| | S115 | female | 60's | multiple alopecia areata | C | once a day | After 3 days, stimulated hair growth was confirmed. Black hairs started to grow and hair elongation was fast |
| SEQ ID NO 43: (CFGRKMDRISSS TGLGC) | S116 | male | 40's | male AGA | B | 1 application/day on forehead thinning area | After 2-3 days, hair gained elasticity and resilience. After 7 days, hair gained volume, restoration was confirmed |
| | S117 | male | 20's | multiple alopecia areata | D | once a day | After 3 days, stimulated hair growth was confirmed. |
| SEQ ID NO 44: (CFGRKMDRISSS AGLGC) | S118 | female | 60's | female AGA | C | once a day | After 1 day, hair gained elasticity, resilience and increased volume. Hair started to grow, restoration and elongation were observed |
| | S119 | female | 20's | multiple alopecia areata | C | once a day | After 3 days, stimulated hair growth was confirmed. |
| SEQ ID NO 45: (CFSRRMDRISSS SGLGC) | S120 | male | 40's | male AGA | C | once a day | After 1 day, hair gained elasticity, resilience and increased volume. Hair started to grow, restoration and elongation were observed. |
| | S121 | female | 40's | healthy skin (scalp) | C | once a day | After 1 day, hair volume was increased. Hair gained elasticity and resilience. |
| SEQ ID NO 46: (CFSRKMDRISST SGLGC) | S122 | female | 60's | female AGA | C | once a day | After 1 day, hair gained elasticity, resilience and increased volume. Hair started to grow, restoration and elongation were observed. |
| | S123 | female | 60's | healthy skin (scalp) | C | once a day | After 1 day, hair became fuller with increased volume. Hair gained elasticity and resilience. After 7 days, grown hairs were predominantly black over white hairs. White hairs turned black. |
| SEQ ID NO 47: (CFSRKMDRISSS TGLGC) | S124 | male | 40's | healthy skin (scalp) | C | once a day | After 1 day, hair volume was increased. Hair gained elasticity and resilience. |
| | S125 | female | 50's | female AGA | C | once a day | After 1 day, hair gained elasticity, resilience and increased volume. Hair started to grow, restoration and elongation were observed. |
| SEQ ID NO 48: (CFSRKMDRISSS SGIGC) | S126 | female | 40's | multiple alopecia areata | B | once a day | After 5 days, hair root regeneration and hair growth stimulation were confirmed |
| | S127 | female | 60's | healthy skin (scalp) | C | once a day | After 1 day, hair became fuller with increased volume. Hair gained elasticity and resilience. After 7 days, grown hairs were predominantly black over white hairs. White hairs turned black |
| | S128 | female | 50's | female AGA | C | once a day | After 1 day, hair gained elasticity, resilience and increased volume. Hair started to grow, restoration and elongation were observed. |

TABLE 29-continued

| SEQ ID NO (amino acid sequence) of the cyclic peptide used | ID | Sex | Age | Cases | Formulation | Treatment | Diagnostic impression of hair and scalp after application |
|---|---|---|---|---|---|---|---|
| SEQ ID NO 49: (CFSRKMDRISSS SGLAC) | S129 | female | 60's | female AGA | C | once a day | After 1 day, hair gained elasticity, resilience and increased volume. |
| | S130 | female | 60's | alopecia areata | B | once a day | After 5 days, hair started to grow and hair density was increased |
| | S131 | female | 40's | healthy skin (scalp) | C | once a day | After 1 day, hair volume was increased. Hair gained elasticity and resilience. |
| SEQ ID NO 50: (CFGRRMDRISST SGLGC) | S132 | male | 50's | male AGA | C | once a day | After 1 day, hair gained elasticity, resilience and increased volume. Hair started to grow, restoration and elongation were observed. |
| | S133 | male | 40's | healthy skin (scalp) | C | once a day | After 1 day, hair volume was increased. Hair gained elasticity and resilience. |
| SEQ ID NO 51: (CFGRRMDRISSS TGLGC) | S134 | male | 40's | male AGA | B | 1 application/day on forehead thinning area | After 2 or 3 days, hair gained elasticity and resilience. After 7 days, hair gained volume, restoration was confirmed. |
| | S135 | male | 50's | healthy skin (scalp) | C | once a day | After 1 day, hair became fuller with increased volume. Hair gained elasticity and resilience. |
| SEQ ID NO 52: (CFGRRMDRISSS SGIGC) | S136 | male | 60's | male AGA | C | once a day | After 1 day, hair gained elasticity, resilience and increased volume. Hair started to grow, restoration and elongation were observed. |
| | S137 | female | 40's | multiple alopecia areata | B | once a day | After 5 days, hair root regeneration and hair growth stimulation were confirmed. |
| | S138 | female | 60's | healthy skin (scalp) | C | once a day | After 1 day, hair became fuller with increased volume. Hair gained elasticity and resilience. After 7 days, grown hairs were predominantly black over white hairs. White hairs turned black. |
| SEQ ID NO 53: (CFGRRMDRISSS SGLAC) | S139 | female | 40's | female AGA | C | once a day | After 1 day, hair gained elasticity, resilience and increased volume. |
| | S140 | male | 40's | healthy skin (scalp) | C | once a day | After 1 day, hair volume was increased. Hair gained elasticity and resilience. |
| SEQ ID NO 54: (CFGRKMDRISST SGIGC) | S141 | male | 40's | male AGA | B | 1 application/day on forehead thinning area | After 2 or 3 days, hair gained elasticity and resilience. After 7 days, hair gained volume, restoration was confirmed. |
| | S142 | female | 50's | healthy skin (scalp) | C | once a day | After 1 day, hair became fuller with increased volume. Hair gained elasticity and resilience. After 7 days, grown hairs were predominantly black over white hairs. White hairs turned black. |
| SEQ ID NO 55: (CFGRKMDRISST SGLAC) | S143 | male | 50's | male AGA | C | once a day | After 1 day, hair gained elasticity, resilience and increased volume. Hair started to grow, restoration and elongation were observed. |
| | S144 | female | 60's | healthy skin (scalp) | C | once a day | After 1 day, hair became fuller with increased volume. Hair gained elasticity and resilience. After 7 days, grown hairs were predominantly black over white hairs. White hairs turned black. |

TABLE 29-continued

| SEQ ID NO (amino acid sequence) of the cyclic peptide used | ID | Sex | Age | Cases | Formulation | Treatment | Diagnostic impression of hair and scalp after application |
|---|---|---|---|---|---|---|---|
| SEQ ID NO 56: (CFGRKMDRISSS TGIGC) | S145 | male | 40's | male AGA | C | once a day | After 1 day, hair gained elasticity, resilience and increased volume. Hair started to grow, restoration and elongation were observed. |
| | S146 | male | 40's | healthy skin (scalp) | C | once a day | After 1 day, hair volume was increased. Hair gained elasticity and resilience. |
| SEQ ID NO 57: (CFGRKMDRISSS TGLAC) | S147 | male | 50's | male AGA | C | once a day | After 1 day, hair gained elasticity, resilience and increased volume. Hair started to grow, restoration and elongation were observed. |
| | S148 | male | 40's | healthy skin (scalp) | C | once a day | After 1 day, hair volume was increased. Hair gained elasticity and resilience |
| SEQ ID NO 58: (CFGRKMDRISSS SGIAC) | S149 | female | 40's | female AGA | C | once a day | After 1 day, hair gained elasticity, resilience and increased volume. |
| | S150 | female | 40's | healthy skin (scalp) | C | once a day | After 1 day, hair volume was increased. Hair gained elasticity and resilience. |
| SEQ ID NO 59: (CFSRRMDRISST SGLGC) | S151 | male | 50's | male AGA | C | once a day | After 1 day, hair gained elasticity resilience and increased volume. Hair started to grow, restoration and elongation were observed. |
| | S152 | male | 40's | healthy skin (scalp) | C | once a day | After 1 day, hair volume was increased. Hair gained elasticity and resilience. |
| SEQ ID NO 60: (CFSRRMDRISSS TGLGC) | S153 | male | 60's | male AGA | C | once a day | After 1 day, hair gained elasticity, resilience and increased volume. Hair started to grow, restoration and elongation were observed. |
| | S154 | male | 40's | healthy skin (scalp) | C | once a day | After 1 day, hair volume was increased. Hair gained elasticity and resilience. |
| SEQ ID NO 61: (CFSRRMDRISSS SGIGC) | S155 | female | 60's | female AGA | C | once a day | After 1 day, hair gained elasticity, resilience and increased volume. Hair started to grow, restoration and elongation were observed. |
| | S156 | male | 60's | healthy skin (scalp) | C | once a day | After 1 day, hair became fuller with increased volume. Hair gained elasticity and resilience. After 7 days, grown hairs were predominantly black over white hairs. White hairs turned black. |
| SEQ ID NO 62: (CFSRRMDRISSS SGLAC) | S157 | male | 50's | male AGA | C | once a day | After 1 day, hair gained elasticity, resilience and increased volume. Hair started to grow, restoration and elongation were observed. |
| | S158 | male | 40's | healthy skin (scalp) | C | once a day | After 1 day, hair volume was increased. Hair gained elasticity and resilience. |
| SEQ ID NO 63: (CFSRKMDRISST SGIGC) | S159 | male | 60's | male AGA | B | 1 application/day on forehead thinning area | After 2 or 3 days, hair gained elasticity and resilience. After 7 days, hair gained volume, restoration was confirmed. |
| | S160 | male | 40's | healthy skin (scalp) | C | once a day | After 1 day, hair volume was increased. Hair gained elasticity and resilience. |

TABLE 29-continued

| SEQ ID NO (amino acid sequence) of the cyclic peptide used | ID | Sex | Age | Cases | Formulation | Treatment | Diagnostic impression of hair and scalp after application |
|---|---|---|---|---|---|---|---|
| SEQ ID NO 64: (CFSRKMDRISSS TGIGC) | S161 | male | 60's | healthy skin (scalp) | C | once a day | After 1 day, hair became fuller with increased volume. Hair gained elasticity and resilience. After 7 days, grown hairs were predominantly black over white hairs. White hairs turned black. |
| | S162 | female | 50's | female AGA | C | once a day | After 1 day, hair gained elasticity, resilience and increased volume. Hair started to grow, restoration and elongation were observed |
| SEQ ID NO 65: (CFSRKMDRISSS TGLAC) | S163 | male | 40's | male AGA | B | 1 application/day on forehead thinning area | After 2 or 3 days, hair gained elasticity and resilience. After 7 days, hair gained volume, restoration was confirmed. |
| | S164 | male | 40's | healthy skin (scalp) | C | once a day | After 1 day, hair volume was increased. Hair gained elasticity and resilience. |
| SEQ ID NO 66: (CFSRKMDRISSS SGIAC) | S165 | male | 60's | male AGA | C | once a day | After 1 day, hair gained elasticity, resilience and increased volume. Hair started to grow, restoration and elongation were observed. |
| | S166 | male | 40's | healthy skin (scalp) | C | once a day | After 1 day, hair volume was increased. Hair gained elasticity and resilience. |
| SEQ ID NO 67: (CFGRRMDRISST SGIGC) | S167 | male | 40's | male AGA | B | 1 application/day on forehead thinning area | After 2-3 days, hair gained elasticity and resilience. After 7 days, hair gained volume, restoration was confirmed. |
| | S168 | female | 60's | healthy skin (scalp) | C | once a day | After 1 day, hair became fuller with increased volume. Hair gained elasticity and resilience. After 7 days, grown hairs were predominantly black over white hairs. White hairs turned black. |
| SEQ ID NO 68: (CFGRRMDRISST SGLAC) | S169 | female | 40's | female AGA | C | once a day | After 1 day, hair gained elasticity, resilience and increased volume. |
| | S170 | male | 40's | healthy skin (scalp) | C | once a day | After 1 day, hair volume was increased. Hair gained elasticity and resilience. |
| SEQ ID NO 69: (CFGRRMDRISSS TGIGC) | S171 | male | 60's | male AGA | B | 1 application/day on forehead thinning area | After 2 or 3 days, hair gained elasticity and resilience. After 7 days, hair gained volume, restoration was confirmed. |
| | S172 | male | 30's | multiple alopecia areata | C | once a day | After 1 day, hairs started to grow and grew. |
| | S173 | male | 60's | healthy skin (scalp) | C | once a day | After 1 day, hair became fuller with increased volume. Hair gained elasticity and resilience. After 7 days, grown hairs were predominantly black over white hairs. White hairs turned black. |
| SEQ ID NO 70: (CFGRRMDRISSS TGLAC) | S174 | female | 50's | female AGA | C | once a day | After 1 day, hair gained elasticity, resilience and increased volume. |
| | S175 | male | 40's | healthy skin (scalp) | C | once a day | After 1 day, hair volume was increased. Hair gained elasticity and resilience. |

TABLE 29-continued

| SEQ ID NO (amino acid sequence) of the cyclic peptide used | ID | Sex | Age | Cases | Formulation | Treatment | Diagnostic impression of hair and scalp after application |
|---|---|---|---|---|---|---|---|
| SEQ ID NO 71: (CFSRRMDRISST SGIGC) | S176 | male | 60's | male AGA | C | once a day | After 1 day, hair gained elasticity, resilience and increased volume. Hair started to grow, restoration and elongation were observed. |
| | S177 | male | 20's | multiple alopecia areata | C | once a day | After 1 day, hairs started to grow and grew. |
| | S178 | male | 60's | healthy skin (scalp) | C | once a day | After 1 day, hair became fuller with increased volume. Hair gained elasticity and resilience. After 7 days, grown hairs were predominantly black over white hairs. White hairs turned black. |
| SEQ ID NO 72: (CFSRRMDRISST SGLAC) | S179 | male | 40's | male AGA | B | 1 application/day on forehead thinning area | After 2 or 3 days, hair gained elasticity and resilience. After 7 days, hair gained volume, restoration was confirmed. |
| | S180 | male | 40's | healthy skin (scalp) | C | once a day | After 1 day, hair volume was increased. Hair gained elasticity and resilience. |
| SEQ ID NO 73: (CFSRRMDRISSS TGIGC) | S181 | female | 40's | female AGA | C | once a day | After 1 day, hair gained elasticity, resilience and increased volume. |
| | S182 | female | 40's | alopecia areata | B | once a day | After 5 days, hair started to grow and hair density was increased. |
| | S183 | female | 60's | healthy skin (scalp) | C | once a day | After 1 day, hair became fuller with increased volume. Hair gained elasticity and resilience. After 7 days, grown hairs were predominantly black over white hairs. White hairs turned black. |
| SEQ ID NO 74: (CFSRRMDRISSS TGLAC) | S184 | male | 60's | male AGA | C | once a day | After 1 day, hair gained elasticity, resilience and increased volume. Hair started to grow, restoration and elongation were observed. |
| | S185 | male | 40's | healthy skin (scalp) | C | once a day | After 1 day, hair volume was increased. Hair gained elasticity and resilience. |
| SEQ ID NO 75: (CFSRRMDRISSS SGIAC) | S186 | male | 40's | male AGA | B | 1 application/day on forehead thinning area | After 2 or 3 days, hair gained elasticity and resilience. After 7 days, hair gained volume, restoration was confirmed. |
| | S187 | female | 40's | multiple alopecia areata | B | once a day | After 5 days, hair root regeneration and hair growth stimulation were confirmed. |
| | S188 | female | 50's | healthy skin (scalp) | C | once a day | After 1 day, hair became fuller with increased volume. Hair gained elasticity and resilience. After 7 days, grown hairs were predominantly black over white hairs. White hairs turned black. |

In SEQ ID NOS 16-75. 1st Cys and 17th Cys from left form a disulfide bond.

The result described above demonstrated that the cyclic peptide of the invention exhibits a similar effect as the cyclic peptide expressed by Formula I-a even if some amino acids of the cyclic peptide have been replaced.

Specifically, it has effects of preventing hair loss at the applied site, stimulating hair growth or promoting hair growth, giving hair resilience and elasticity, increasing volume of hair and dramatically decreasing falling hairs when it was applied to the site of alopecia or hair growth stimulation, etc. It also has effects of nourishing hair, promoting hair growth stimulation, improving/preventing thinning of hair at the applied site. In this case, the stimulated hair tends to become a terminal (non-white) hair. Moreover, these effect exhibit significantly faster as compared to other active agents conventionally used in alopecia therapeutics such as BNP such that stimulated hair growth can be confirmed one day after only one application even in the case of an intractable alopecia areata *multilocularis* or ophiasis. In addition, resulting effects persists remarkably even after terminating application and the stimulated hair keep growing. In the case of AGA or healthy subject it exert immediate effect of providing hair with resilience and elasticity on the following day, increasing the volume, and dramatically decreasing falling hairs, which effects last even after terminating application. It also has an improving and preventing effect on dermatitis. Therefore, it can improve or prevent skin inflammation associated with alopecia. Such effect is advantageous in cases where alopecia has been exacerbated due to skin condition of the applied site (e.g., scalp). Moreover, the external preparation of the present invention exerts a moisturizing and skin texture-improving effects at the applied site when being applied to skin as described above. It can remove and suppress dandruff and itching, while giving moisture to hair and scalp, improving and preventing dryness and keeping hair and scalp healthy. It also can improve seborrhea. On the other hand, when it is used as an alopecia therapeutic/prophylactic, it can be used for the purpose of treating or preventing one or more of applicable alopecia including, for example, those described below, without being particularly limited thereto.

(Acquired Alopecia)
(i) Alopecia without accompanying scarring or skin lesion (alopecia areata, male pattern alopecia, seborrheic alopecia, alopecia pityroides, female pattern alopecia, gestational alopecia, malignant alopecia, senile alopecia, alopecia totalis, alopecia areata *multilocularis*, ophiasis, drug-induced alopecia, cancer chemotherapy-induced alopecia and radiation exposure-induced alopecia, traumatic/mechanical alopecia, malnutrition/metabolic disorder associated alopecia, endocrine dysfunction associated alopecia and telogen effluvium (post partum alopecia, alopecia after high fever)).
(ii) Alopecia observed in skin lesion or pathologic skin (infection-induced alopecia, tumor-induced alopecia, inflammation-induced alopecia).
(iii) Scarring alopecia (skin infection-induced alopecia, alopecia induced by infiltration of inflammatory cells).

(Congenital Alopecia)
Diffuse alopecia, congenital atrichia, alopecia in hereditary syndromes, localized alopecia, phakomatosis, aplasia cutis, alopecia areata *multilocularis*.

It exerts an excellent effect especially on acquired alopecia, preferably on alopecia without accompanying scarring or skin lesion, more preferably on alopecia areata, male pattern alopecia, seborrheic alopecia, alopecia pityroides, female pattern alopecia, gestational alopecia, malignant alopecia, senile alopecia, alopecia totalis, alopecia areata *multilocularis*, ophiasis, drug-induced alopecia, cancer chemotherapy-induced alopecia and radiation exposure-induced alopecia, traumatic/mechanical alopecia, malnutrition/metabolic disorder associated alopecia, endocrine dysfunction associated alopecia and telogen effluvium. Therefore, the external preparation of the present invention can be used for the purpose of treating or preventing at least one or more alopecia selected from the above-mentioned group.

One simple application onto aforementioned affected site at 3 μg/ml to 500 μg/ml improved or eliminated itch, dandruff, scalp redness and inflammation immediately thereafter (immediate effect). A single application stimulated hair growth, grew hair, provided hair with resilience, elasticity and increased volume, and dramatically decreased falling hairs, and these effects started on the day after the application and persisted for one week or more (long-lasting effect). If application was carried on for about one week, these effects are further improved, and even after terminating application, the effects lasted from 1 to 2 weeks such that stimulation of hair growth and restoration of hair continued and there were little or no falling hairs.

9.2 Confirming Effects on Skin

The obtained cyclic peptide was prepared in purified water at 3, 15, 30, 100 or 500 μg/ml and applied to affected site. Each of formulations A to E in the table indicates the concentration of the cyclic peptide at 3, 15, 30, 100 or 500 μg/ml, respectively. The absence of the effect upon the application of purified water without the peptide confirmed the effect was not a placebo effect.

TABLE 30

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| SEQ ID NO 16: (CFVRKMDRISSSSGLGC) | Q1 | female | 30's | eczema | B | once a day | After 3 minutes, red papule was reduced and remitted. | Itches were remitted immediately after application. |
| | Q2 | male | 20's | atopic dermatitis | B | once a day | After 2 minutes, erythema, edema and infiltration was remitted. | Itches were eliminated immediately after application. |
| | Q3 | male | 80's | plaque psoriasis | C | once a day, 2 days | After 3 minutes, crusts, scales, erythema and infiltration were remitted. | |
| | Q4 | male | 40's | plaque psoriasis | C | once a day, | After 10 minutes, scales, erythema and infiltration were remitted. | |
| | Q5 | female | 30's | eczema | C | once a day | After 3 minutes, erythema was remitted. | |
| | Q6 | male | 20's | atopic dermatitis | B | once a day. 7 days | Erythema, infiltration and papule were remitted. | Itches were remitted immediately after application. |
| | Q7 | female | 60's | eczema | C | once a day | After 2 minutes, erythema, infiltration and papule were remitted. After 20 minutes, they were amaliorated. | |
| | Q8 | female | 20's | atopic dermatitis | C | once a day | After 2 minutes, erythema and infiltration were remitted. | Itches were eliminated in 1 minute |
| | Q9 | male | 10's | atopic dermatitis | C | once a day | Redness vanished immediately after application. | Itches were extincted in 1 minute. |
| SEQ ID NO 17: (CFGQKMDRISSSSGLGC) | Q10 | male | 40's | atopic dermatitis | C | once a day | After 3 minutes, erythema and infiltration were remitted. | After 3 minutes, itches were remitted. |
| | Q11 | male | 10's | nummular eczema | C | once a day | After 3 minutes, infiltration, erythema exudate and scales were remitted. | |
| | Q12 | male | 20's | eczema | B | once a day | After 2 minutes, scales and erythema were remitted. With only 1 application, no recurrence for 7 days thereafter. | Iches were elimintaed immediately after application. |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| SEQ ID NO 18: (CFGQKMDRISSSSGLGC) | Q13 | male | 60's | milleria | C | once a day | After 2 minutes, redness was remitted. | |
| | Q14 | female | 40's | roughened skin | A | once a day | After 2 minutes, zits, dryness and rawness on skin were reduced, skin was moisturized and it texture improved. After 7 days, large wrinkles and nasolabial fold became less deep. | |
| SEQ ID NO 19: (CFGRRMDRISSSSGLGC) | Q15 | male | 20's | eczema, atopic dermatitis | C | once a day | After 2 minutes, erythema and scales were remitted. After 20 minutes, skin got moisturized. After only 1 application, erythema vanishes and kept in a good condition for 1 week. | |
| | Q16 | male | 20's | atopic dermatitis | C | once a day | After 5 minutes, wound was apithelized, erythema and papule were improved. | |
| | Q17 | female | 40's | roughened skin | B | once a day | After 2 minutes, redness was remitted. Roughness and skin texture were also improved. | |
| | Q18 | female | 30's | roughened skin | B | once a day | After 2 minutes, was remitted. Roughness and skin texture were also improved. Rawness got better, iches vanished immediately after application, skin were moisturized and smooth. | |
| | Q19 | male | 40's | plaque psoriasis | C | once a day | After 3 minutes, erythema, crusts scales and infiltration were remitted. | |
| | Q20 | male | 40's | eczema | C | once a day | Erythema was remitted immediately after application. | Itches were extincted immediately after application |
| SEQ ID NO 20: (CFGRKLDRISSSSGLGC) | Q21 | female | 60's | eczema | C | once a day | After 1 minute, red papule was reduced and extincted. | After 3 minutes, iches were remitted |
| | Q22 | male | 20's | atopic dermatitis | B | once a day | After 2 minutes, erythema and scales were remitted. | Itches vanished completely immediately after application. |
| | Q23 | female | 40's | eczema | C | once a day | After 2 minutes, erythema, scales and papule were remitted. | Rawness vanished immediately after application |
| | Q24 | female | 30's | roughened skin, acne | B | once a day | After 3 minutes, zits, ruggedness, dry skin and redness were remitted, skin got full and its texture improved. Acnes were reduced and redness was remitted. | Iches application were eliminated immediately after application. |
| | Q25 | female | 60's | wrinkles, dry skin | B | once a day | After 2 minutes, wrinkles became less deep, dry skin was remitted. | |
| | Q26 | female | 60's | eczema | C | once a day | After 3 minutes, erythema and scales were remitted. | |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| SEQ ID NO 21: (CFGQKIDRISSSSGLGC) | Q27 | male | 20's | eczema, atopic dermatitis | C | once a day | After 3 days, erythema, scales and papule were improved. Cracks were epithelized, skin got moisturized and improved. | Iches were eliminated immediately after application. |
| | Q28 | female | 40's | eczema | B | once a day | After 2 minutes, infiltration, erythema, papule and scratch wound were remitted. | After 1 minute, iches were eliminated. |
| | Q29 | male | 40's | atopic dermatitis | B | once a day | Immediately after application, erythema and scales and remitted. | After 3 minutes, iches were eliminated. |
| SEQ ID NO 22: (CFGQKMDRISSSSGLGC) | Q30 | female | 30's | atopic dermatitis | C | once a day | After 3 minutes, 1 application, erythema and infiltration were remarkably remitted, dry skin, scales and cracks were also improved. | After 30 seconds, Iches were eliminated. |
| | Q31 | female | 70's | eczema | C | once a day | immediately after application, erythema and papule remitted. | Facial rawness vanished immediately after application. |
| | Q32 | female | 30's | atopic dermatitis | B | once a day, 7 days | A remarkable improvement after 2 days, and erythema was eliminated. | |
| | Q33 | female | 40's | atopic dermatitis | C | once a day, 2 days | After 1 minute, erythema was remitted. After 2 minutes, scratch wound was epithelized. | Iches were eliminated immediately after application |
| | | | | | | | After 3 minutes, skin texture was improved. With only 1-day applicatioin, erythema was eliminated, skin texture was improved with no dryness. | Iches were eliminated immediately after application |
| | Q34 | male | 20's | atopic dermatitis | C | once a day | After 2 minutes, erythema and scales were remitted. No recurrence for 7 days thereafter. | Iches were remitted immediately after application |
| | Q35 | female | 50's | chronic eczema | C | once a day | After 2 applications, lichenification erythema was remitted. No recurrence for 3 weeks thereafter. | Iches were eliminated immediately after application |
| | Q36 | female | 50's | roughened skin | C | once a day | Skin roughness was cured immediately after application. After 2 minutes, skin got moisturized. Its redness faded. Skin texture was finely improved. After 7 days, skin tone became brighter, spots faded and flabiness was improved. | |
| | Q37 | female | 30's | roughened skin | B | once a day | After 2 minutes, zits, redness was remitted. After 1 day, skin became normal tone and its texture was improved. | Rawness vanished immediately after application. |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| SEQ ID NO 23: (CFGQKMDRISSSSGLGC) | Q38 | female | 40's | atopic dermatitis | C | once a day | After 2 minutes, scratch wound was epithelized and cured. Erythema was improved. | After 1 minute, acnes were eliminated. |
| | Q39 | male | 20's | eczema | C | once a day | After 2 minutes, erythema, dry skin and scales were improved and skin got moisturized. | Itches were abeled immediately after application. |
| | Q40 | male | 20's | atopic dermatitis | C | once a day | After 2 minutes, erythema, scales and infiltration were remitted. With 1 application, no recurrence for 7 days. | Itches were extincted immediately after application. |
| | Q41 | male | 40's | plaque psoriasis | C | once a day | After 3 minutes, crustsscaleserythema and infiltration were remitted. | |
| | Q42 | female | 30's | roughened skin | B | once a day | After 2 minutes, roughness, zits and redness were reduced, skin got moisturized and its texture was improved. | After 2 minutes, itches were extincted. |
| | Q43 | female | 50's | rosacea, acne | C | once a day | After 1 minute, erythema, telangiectasia and acne were remitted. After 2 minutes, papule, infiltration, acne, dry skin and redness was remitted. | |
| SEQ ID NO 24: (CFGQKMDRISASSGLGC) | Q44 | male | 10's | atopic dermatitis | C | once a day | After 3 minutes, erythema, scales and infiltration were remitted. Further improvement after 40 minutes. Scratch wound was epithelized. | |
| | q45 | male | 20's | atopic dermatitis | C | once a day | After 3 minutes, erythema and infiltration were remitted. | After 3 minutes, Iches were eliminated. |
| | Q46 | male | 20's | | C | once a day | After 3 days, cracks were epithelized. Erythema, scales and infiltration were remitted. | |
| | Q47 | male | 20's | atopic dermatitis | C | once a day | After 2 minutes, wound was epithelized. Erythema, scales and licherification remitted. After 5 minutes, skin got softened, erythema and infiltration were improved. | Iches were eliminated immediately after application. |
| SEQ ID NO 25: (CFGQKMDRISSQSGLGC) | Q48 | male | 20's | | C | once a day | After 2 minutes, erythema, scales and infiltration were remitted. Skin got moisturized. | Iches were remitted immediately after application. |
| | Q49 | female | 40's | roughened skin | B | once a day | After 3 minutes, deep wrinkles were less deep, dry skin and redness were improved, skin got moisturized and full. By using for 1 week, large wrinkles and nasolabial fold became less deep. Skin became brighter. Spots faded.Flabiness was improved. | Rawness was eliminated immediately after application. |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| SEQ ID NO 26: (CFGQKMDRISSSSGLGC) | Q50 | male | 60's | plaque psoriasis | C | once a day | After 2 minutes, scales and infiltration remitted. | |
| | Q51 | male | 30's | millaria | C | once a day | After 2 minutes, remitted. | |
| | Q52 | male | 20's | acne vulgaris | C | once a day | After 6 minutes, acne became dry and was reduced in size. | |
| | Q53 | female | 60's | eczema | C | once a day | After 3 minutes, erythema and infiltration were remitted. | |
| | Q54 | female | 10's | atopic dermatitis | C | once a day | After 4 minutes, amelicrated. After 2 minutes, strong itches almost vanished. Erythema and lichenification were improved. Skin got softened. | |
| | Q55 | female | 40's | roughened skin | C | once a day | After 2 minutes, zits, redness and roughness were improved. Skin got moisturized and its texture was improved. Skin was improved. | Rawness vanished immediately after application. |
| SEQ ID NO 27: (CFGQKMDRISSSSGLGC) | Q56 | female | 50's | roughened skin, acne | C | once a day | After 3 minutes, dry skin was improved, skin got moisturized and its texture was finely improved. Redness vanished. Inframmation in acne was remitted, redness faded and dried. By using for 1 week, skin became brighter. | |
| | Q57 | male | 20's | atopic dermatitis | C | once a day | After 3 minutes, erythema, infiltration and lichenification was improved. | Iches were eliminated immediately after application. |
| SEQ ID NO 28: (CFGQKMDRISSISGLGC) | Q58 | female | 30's | eczema | C | once a day | After 1 minute, erythema and infiltration were remitted. | After 1 minute, Iches were eliminated. |
| | Q59 | female | 20's | roughened skin | A | once a day | After 7-day continuous application, skin roughness vanished, wrinkles were less deep, and skin became brighter. | |
| | Q60 | female | 20's | roughened skin | C | once a day | After 2 minutes, scales were improved. With 1 application/day, roughness was improved and skin could be kept moisturized. | |
| SEQ ID NO 29: (CFGQKMDRISSMSGLGC) | Q61 | female | 30's | eczema | C | once a day | After 1 minute, erythema and infiltration were remitted. | Iches were eliminated immediately after application. |
| SEQ ID NO 30: (CFGQKMDRISSSVGLGC) | Q62 | male | 20's | atopic dermatitis | B | once a day, 7 days | After 3 days, erythema and infiltration were remitted. | |
| | Q63 | female | 60's | eczema | C | once a day | After 1 minute, erythema and papule were remitted. After 3 days, there were almost cured. | Iches were eliminated immediately after application. |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| | Q64 | male | 50's | dry skin | C | once a day | Immediately after application, skin got promptly moisturized and its texture was improved, zits, erythema and roughned skin were improved. | |
| | Q65 | male | 20's | atopic dermatitis | C | once a day | After 10 minutes, lichenification was improved. Skin got softened, erythema and scales were improved. | Iches were eliminated immediately after application. |
| | Q66 | female | 40's | roughened skin | A | once a day | After 1 day with 1 application, skin conditions of roughness, zits and itches were improved and skin texture was finely improved. The effect lasted for 7 days thereafter. | |
| SEQ ID NO 31: (CFGQKMDRISSSSSRLGC) | Q67 | male | 20's | atopic dermatitis | C | once a day | After 2 minutes, erythema and papule was remitted. | |
| SEQ ID NO 32: (CFGQKMDRISSSSSGMGC) | Q68 | male | 30's | millaria | C | once a day | After 2 minutes, red papule was reduced in size, skin dryness was remitted. | |
| | Q69 | male | 10's | atopic dermatitis, numeuler | C | once a day 6 | After 3 minutes, exudate stopped, erythema and infiltration were improved. | |
| SEQ ID NO 33: (CFGQKMDRISSSSSGIGC) | Q70 | female | 30's | contact dermatits | C | 2 applicatioin | After 3 minuts, erythema, infiltration and eczema were remitted. | |
| | Q71 | female | 30's | atopic dermatitis | E | once a day | Immediately after application, erythema and scales were improved. | After 1 minute, iches were eliminated. |
| | Q72 | female | 70's | plaque psoriasis | C | 2 application | After 5 minutes. erythema, scales and infiltration were remitted. | Iches were eliminated immediately after application. |
| | Q73 | female | 40's | roughened skin | B | once a day | In 2 minutes after application, skin was improved. Skin texture was finely improved. Skin got softened. | |
| SEQ ID NO 34: (CFGQKMDRISSSSSGVGC) | Q74 | female | 30's | eczema | C | 2 applicatioin | After 3 minutes, erythema, infiltration and edema remitted. | |
| | Q75 | male | 20's | eczema, acne vulgaris | C | 2 application | After 5 minutes, acne was dried and reduced in size. Erythema and scales were remitted. | After 1 minute, Iches were eliminated. |
| | Q76 | female | 70's | plaque psoriasis | C | 2 application | After 5 minutes, erythema, scales and infiltration were remitted. | |
| | Q77 | female | 40's | roughened skin | C | once a day | After 2 minutes, skin texture was improved, skin got hull, and redness and dryness were improved. | |
| | Q78 | male | 50's | roughened skin | B | once a day | After 3 minutes, skin got moisturized and its texture was improved. | |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| | Q79 | female | 20's | atopic dermatitis | C | once a day | After 3 minutes, erythema and scales were improved. | Itches were improved immediately after application. |
| | Q80 | female | 50's | roughened skin | B | once a day | After 3 minutes, skin roughness was improved, skin got moisturized and its texture was finely improved. Skin gained resilence. After 7 days, large wrinkles and nasolabial fold became less deep. By continuing 4 weeks, spots faded and skin tone became brighter. Skin resilience was improved. Large wrinkles became less deep. | Iches wee eliminated immediately after application. |
| | Q81 | male | 30's | roughened skin | B | once a day | After 3 minutes, skin roughness and redness were improved. Skin texture was finely improved. By continuing for 7 days, skin resilience was improved. | |
| SEQ ID NO 35: (CFGQKMDRISSSSSGAGC) | Q82 | female | 40's | roughened skin | B | once a day | After 3 minutes, roughness skin and dry skin were promptly improved, skin texture was improved. | |
| | Q83 | male | 60's | plaque psoriasis | C | twice a day | After 30 minutes, erythema, scales and infiltration were improved. | |
| | Q84 | male | 40's | plaque psoriasis | C | twice a day | After 20 minutes, erythema and scales were improved. | |
| | Q85 | female | 70's | plaque psoriasis | C | twice a day | After 5 minutes, erythema and scales were remitted. | |
| SEQ ID NO 36: (CFGQKMDRISSSSSGLSC) | Q86 | female | 10's | atopic dermatitis | C | once a day | After 2 minutes, linchenification was remarkably remitted, erythema, scales inflimation, cracks, scratch wound, etc. all remitted. After 5 minutes, improved with only mild infiltration left. | After 2 minutes, strong iches were eliminated. |
| | Q87 | female | 20's | atopic dermatitis | B | once a day | After 1 minute, erythema, infiltration and papule remitted. After 4 minutes, infiltration was remitted with only mild erythema left. | After 2 minutes, iches were eliminated. |
| | Q88 | male | 10's | atopic dermatitis | C | once a day | After 3 minutes, erythema, scales, infiltration and scratch wound were remitted. | After 3 minutes, iches were eliminated. |
| | Q89 | female | 40's | roughened skin | B | once a day | Immediately after application, itches and redness were improved. After 3 minutes, skin got full and resilient, and skin was improved. | |
| | Q90 | male | 50's | seborrhea dermatits | C | once a day, 3 days | Immediately after application, seborrhea was remitted. After 3 days, erythema and seborrhea was remitted. | Itches were remitted immediately after application. |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| SEQ ID NO 37: (CFGQKMDRISSSSGLAC) | Q91 | male | 60's | plaque psoriasis | C | once a day | After 2 minutes, erythema and scales were remitted. | |
| | Q92 | male | 20's | atopic dermatitis prurigo nodularis, | C | once a day | After 2 minutes, erythema and infiltration were remitted. Applied twice. After 15 minutes, pringe nodularis on hip was remitted. | Iches were eliminated immediately after application. |
| | Q93 | female | 40's | roughened skin | B | once a day | After 3 minutes, roughened skin and dry skin were improved promptly and skin texture was improved. | |
| | Q94 | male | 40's | plaque psoriasis | C | once a day | After 20 minutes, erythema and scales were remitted. | |
| | Q95 | male | 30's | atopic dermatitis | C | once a day | After 2 minutes, scratch wound epithelized erythema was remitted. | |
| SEQ ID NO 38: (CFGQKMDRISSSSGLGC) | Q96 | male | 20's | atopic dermatitis | C | once a day | After 3 minutes, cracks was reduced in size. Erythema, scales and lichenification were remitted. | immediately after application, itches and rawness were removed. |
| | Q97 | female | 40's | roughened skin | B | once a day | After 1 minute, dry skin was improved, skin got moiturized and full, and skin texture was improved. | immediately after application, itches were removed. |
| | Q98 | female | 200's | chronic eczema | C | once a day | immediately after application, erythema and scales were remitted. | |
| | Q99 | male | 20's | atopic dermatitis | C | once a day | After 2 minutes, redness was improved. After 3 minutes, erythema, infiltration and papule were remitted. After 1 application, the effect lasted for 6 days with no recurrence. | After 1 minute, iches were eliminated. After 1 application, no itches for 6 days thereafter. |
| | Q100 | female | 50's | prurigo nodularis, eczema | C | once a day | After 3 minutes, nodes wereflatened, scratch wound became dry and epithelized with no more exudate. | Iches were eliminated immediately after application. |
| SEQ ID NO 39: (CFSRKMDRISSSSGLGC) | Q101 | female | 50's | prurigo nodularis, eczema | C | once a day | After 3 minutes, nodes were flattened. | |
| | Q102 | female | 10's | chronic eczema | C | once a day | After 2 minutes, an intractable eczema that cannot be remitted by applying strong steriod ointments was remitted, and erythema, scales and papule were reduced. | |
| | Q103 | female | 50's | eczema | C | once a day | After 2 minutes, erythema, scales and pigmentation were remitted. Skin got full and soft, with fresh color. | |
| | Q104 | female | 20's | atopic dermatitis | D | once a day | Scratch wound was epithelized Exudate was dried ad lichenification was remitted. erythema and infiltration were remitted. | Iches were eliminated immediately after application. |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| | Q105 | male | 20's | atopic dermatitis | B | once a day | After 3 minutes, erythema and infiltration were remitted. With 1 application, the effect persisted for 1 week with no recurrence. | After 2 minutes, itches and tingling pain were removed. The effect persisted for 7 days with no itches. |
| SEQ ID NO 40: (CFTRKMDRISSSSGLGC) | Q106 | male | 40's | atopic dermatitis | C | once a day | After 2 minutes, erythema, infiltration and lichenification remitted. | Iches were eliminated immediately after application. |
| | Q107 | female | 20's | roughened lips | C | 1 application | After 1 minute, dry skin was improved, cracks were less deep and apithelized. | |
| | Q108 | female | 40's | roughened skin | B | once a day | After 3 minutes, redness and roughness were improved. | |
| | Q109 | female | 30's | healthy skin | C | once a day | After 3 minutes, dark-reddish skin tone was improved to turn fresh color. Dryness, tautnessm rawness and hot flash of skin were removed. With 1 application the effect persisted for 1 week. | |
| SEQ ID NO 41: (CFGRKMDRISSTSGLGC) | Q110 | male | 10's | atopic dermatitis/acne | C | once a day | immediately after application, erythema and infiltration of eczema were remitted. The effects were exhibited remarkably fast. After 3 minutes, erythema was further remitted. Acne was dried and reduced in size. | Iches were eliminated immediately after application. |
| | Q111 | male | 20's | atopic dermatitis | C | once a day | Immediately after application, erythema and infiltration were remitted. After 20 minutes, deep scratch wound was epithelized. | Iches were eliminated immediately after application. |
| | Q112 | female | 40's | roughened lips | B | 1 application | After 1 minute, skintautness and rawness were improved and skin got moisturized. | |
| | Q113 | female | 50's | atopic dermatitis | B | once a day | Iches stopped in 30 seconds. Redness and edema were remitted in 1 minute. | |
| | Q114 | female | 10's | roughened skin/acne | B | once a day | After 1 minute, redness was remitted. After 3 minutes, skin roughness, zits, rough and soft skin texture were improved, skin got full end its texture was finely improved. Acne became dry and reduced in size. | After 3 minutes, skin tautness was removed. |
| | Q115 | female | 40's | roughened skin | B | once a day | Rawness vanished in 1 minute. Skin was moisturized. After 2 minutes, redness, roughness and stiffness were remarkably improved. By using for 1 weel, skin became brighter, flabbiness was improved. | |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| SEQ ID NO 42: (CFGRKMDRISSASGLGC) | Q116 | female | 40's | acne | C | once a day | After 1 minute, redness was remitted. | |
| | Q117 | male | 10's | atopic dermatitis | B | once a day | After 3 minutes, erythema and infiltration were remitted. | Iches were eliminated immediately after application. |
| | Q118 | female | 50's | eczema | C | once a day | After 3 minutes, erythema and dry skin remitted. | |
| SEQ ID NO 43: (CFGRKMDRISSSSTGLGC) | Q119 | male | 40's | atopic dermatitis | C | once a day | After 2 minutes, no discomfort, felt fresh. Erythema, infiltration and lichenification were remitted. | After 3 minutes, roughness and stiffness were removed, and itches vanished. |
| | Q120 | female | 30's | roughened lips | C | once a day | 1 minute after application, dry skin was improved cracks became less deep and epithelized. | |
| | Q121 | female | 40's | roughened skin | B | once a day | After 3 minutes, redness and dry skin were improved. Skin got moisturized promptly, and skin texture was improved. Skin rawness, stiffness and irritation were eliminated. Pores became less distinguised. | |
| | Q122 | female | 40's | rosacae/acne | C | once a day | After 7 minutes, acne was reduce and became dry. | |
| | Q123 | female | 30's | eczema | C | once a day | After 1 minute, redness and infiltration were remitted. | Iches were eliminated immediately after application. |
| SEQ ID NO 44: (CFGRKMDRISSSAGLGC) | Q124 | female | 60's | healthy skin | B | once a day | Skin got moisturized promptly, wrinkles became less deep, skin texture was improved. By using for 4 weeks, large wrinkles and nasolabial fold became less deep. Skin resilence and flabbiness were improved. Spots faded. Skin tone became brighter. | |
| | Q125 | female | 80's | eczema | C | once a day | After 1 minute, erythema and infiltration were remitted. | Iches were remitted immediately after application. |
| SEQ ID NO 45: (CFSRRMDRISSSSGLGC) | Q126 | female | 40's | roughened skin | B | once a day | After 2 minutes, dryness, tautness and rawness of skin were eliminated, skin got full, and wrinkles became less deep. Skin mained elasticity. By using for 5 days, flabbiness was improved. Skin became brighter, nasolabial fold became less deep. By using for 4 weeks, nasolabial fold became less deep. Skin resilience and flabbiness were improved. Spots faded and skin tone became brighter. | |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| SEQ ID NO 46: (CFGRKMDRISSTSGLGC) | Q127 | female | 40's | eczema | C | once a day | After 2 minutes, erythema, scales and infiltration were remitted. Skin got softened. | |
| SEQ ID NO 47: (CFGRKMDRISSSTGLGC) | Q128 | female | 30's | chronic eczema | C | once a day | Immediately after application, erythema and scales were remitted. | |
| SEQ ID NO 48: (CFGRKMDRISSSGIGC) | Q129 | male | 50's | eczema | C | once a day | After 2 minutes, erythema, scales and infiltration were remitted. Skin got moisturized. | |
| SEQ ID NO 49: (CFGRKMDRISSSSGLAC) | Q130 | male | 30's | chronic eczema | C | once a day | Immediately after application, erythema and scales were remitted. | |
| SEQ ID NO 50: (CFGRRMDRISSSTGLGC) | Q131 | male | 50's | eczema | C | once a day | After 2 minutes, erythema, scales and infiltration were remitted. | |
| SEQ ID NO 51: (CFGRRMDRISSSTGLGC) | Q132 | female | 60's | eczema | B | once a day | After 3 minutes, erythema and infiltration were remitted. | |
| SEQ ID NO 52: (CFGRRMDRISSSSGIGC) | Q133 | female | 50's | eczema | C | once a day | After 2 minutes, erythema, scales and infiltration were remitted. Skin got moisturized. | |
| SEQ ID NO 53: (CFGRRMDRISSSSGLAC) | Q134 | female | 20's | eczema | C | once a day | After 1 minute, erythema and infiltration were remitted. | |
| SEQ ID NO 54: (CFSRKMDRISSTSGIGC) | Q135 | female | 30's | roughened skin | B | once a day | After 2 minutes, dryness, tautness and rawness of skin were eliminated, skin got full and wrinkles became less deep. Skin gained elasticity. | |
| SEQ ID NO 54: (CFSRKMDRISSTSGIGC) | Q136 | female | 50's | eczema | C | once a day | After 2 minutes, erythema, scale and infiltration were remitted. | 11 |
| SEQ ID NO 56: (CFGRKMDRISSSTGIGC) | Q137 | male | 20's | roughened skin | B | once a day | After 2 minutes, dryness, tautness and rawness of skin were eliminated, skin got full, and wrinkles became less deep. Skin gained elasticity. | |
| SEQ ID NO 57: (CFGRKMDRISSSTGLAC) | Q138 | female | 40's | eczema | C | once a day | After 2 minutes, erythema, scales and infiltration were remitted, scratch wound was epithelized and dried. | |
| SEQ ID NO 58: (CFGRKMDRISSSSGIAC) | Q139 | female | 30's | eczema | C | once a day | After 2 minutes, erythema, scales, papule and infiltration were remitted. | |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| SEQ ID NO 59: (CFGRKMDRISSSTSGLGC) | Q140 | male | 60's | roughened skin | B | once a day | After 2 minutes, dryness, tautness and rawness of skin were eliminated. Skin gained elasticity, wrinkles became less deep. | |
| SEQ ID NO 60: (CFGRKMDRISSSTGLGC) | Q141 | female | 50's | chronic eczema | C | once a day | Immediately after application, erythema and scales were remitted. | |
| SEQ ID NO 61: (CFSRRMDRISSSSGIGC) | Q142 | female | 30's | chronic eczema | C | once a day | Immediately after application, erythema and scales were remitted. | |
| SEQ ID NO 62: (CFSRRMDRISSSSGLAC) | Q143 | female | 40's | roughened skin | B | once a day | After 2 minutes, dryness, tautness and rawness of skin were eliminated, skin got full, and wrinkles became less deep. Skin gained elasticity. | |
| SEQ ID NO 63: (CFSRKMDRISSTSGIGC) | Q144 | male | 50's | eczema | B | once a day | After 3 minutes, erythema and scales infiltration were remitted, and skin got softened. | |
| SEQ ID NO 64: (CFSRKMDRISSSTSGIGC) | Q145 | male | 40's | chronic eczema | C | once a day | Immediately after application, erythema and scales were remitted. | |
| SEQ ID NO 65: (CFSRKMDRISSSTSGLAC) | Q146 | female | 40's | roughened skin | C | once a day | After 1 minute, skin got moisturized and resilent, skin texture was improved. | |
| SEQ ID NO 66: (CFGRKMDRISSSSGIAC) | Q147 | male | 50's | eczema | C | once a day | After 2 minutes, erythema, scales and infiltration were remitted. | |
| SEQ ID NO 67: (CFSRRMDRISSTSGIGC) | Q148 | female | 70's | roughened skin | B | once a day | After 2 minutes, dryness, tautness and rawness of skin were eliminated, skin got full, and wrinkles became less deep. Skin gained elasticity. | |
| SEQ ID NO 68: (CFSRRMDRISSSTSGLAC) | Q149 | female | 30's | chronic eczema | C | once a day | Immediately after application, erythema and scales were remitted. | |
| SEQ ID NO 69: (CFSRRMDRISSSTSGIGC) | Q150 | female | 20's | eczema | C | once a day | After 2 minutes, erythema, scales, infiltration were improved. | |
| | | | | | | 12 | | |
| SEQ ID NO 70: (CFGRRMDRISSSTSGLAC) | 151 | female | 60's | chronic eczema | C | once a day | immediately after application, erythema and scales were remitted. | |
| | 152 | female | 30's | roughened skin | C | once a day | Redness vanished in 30 seconds. After 1 minute, skin texture improved finely. | |

TABLE 30-continued

| Amino acid sequence of cyclic peptide mutant used | ID | Sex | Age | Diagnostic impression | Formulation | Treatment | Diagnostic impression on skin after application | Itches after application |
|---|---|---|---|---|---|---|---|---|
| SEQ ID NO 71: (CFSRRMDRISSTSGIGC) | 153 | male | 50's | roughened skin | A | once a day | Pores became less distinguished. After 2 minutes, dryness, tautness and rawness of skin were eliminated, skin got full and wrinkles became less deep. Skin gained elasticity. | |
| SEQ ID NO 72: (CFSRRMDRISSTSGLAC) | 154 | male | 50's | chronic eczema | C | once a day | Immediately after application, erythema, scales and papule were remitted. | |
| SEQ ID NO 73: (CFSRRMDRISSSTGIGC) | 155 | male | 20's | chronic eczema | C | once a day | Immdediately after application, erythema and scales were remitted. | |
| SEQ ID NO 74: (CFGRRMDRISSSTGLAC) | 156 | female | 30's | roughened skin | C | once a day | After 1 minute, rawness and hot flash were eliminated, skin got moisturized and its texture improved, wrinkles faded and skin gained elasticity. | |
| | 157 | male | 60's | chronic eczema | D | once a day | Iches were eliminated immediately after application. Redness was remitted. | |
| SEQ ID NO 75: (CFGRRMDRISSSSGIAC) | 158 | female | 60's | eczema | C | once a day | After 2 minutes, erythema, scalesm papule, infiltration were remitted. | |
| SEQ ID NO 43: (CFGRKMDRISSSTGLGC) and SEQ ID NO 19: (CFGRRMDRISSSSLGC) | 258 | male | 40's | atopic dermatitis | C | once a day | After 2 minutes, cracks were epithelized with no more pains and itches. Erythema and scales were also remitted. | |
| SEQ ID NO 43: (CFGRKMDRISSSTGLGC) and SEQ ID NO 99: | 358 | male | 40's | eczema | | once a day | After 2 minutes, wound was epithelized quickly, and erythema, scales and infiltration were remarkably remitted. | |

In SEQ ID NOS 16-75, 1st Cys and 17th Cys from left form a disulfide bond.

The result described above demonstrated that the cyclic peptide of the invention exhibits a similar effect as the cyclic peptide expressed by Formula I-a even if some amino acids of the cyclic peptide have been replaced. Moreover, a similar effect could be obtained by applying the replaced cyclic peptide in a mixture as long as an effective amount of the cyclic peptide is applied.

Specifically, in subjects having atopic dermatitis or eczema, effects were observed immediately after applying 3 μg/ml to 500 μg/ml to affected site, including elimination of itches, epithelialization at infiltrated site, papule or scratch, termination of exudation, epithelialization of a crack. Moreover, a single application induced a persistent effect for a week or more.

When it was applied to healthy or roughened skin, it exerted a moisturizing effect immediately or within a few minutes after application, improving dryness, providing and keeping skin and mucosa with moderate elasticity and flexibility, softening skin, giving skin or mucosa resilience and firmness. Also, fine wrinkles and flabbiness are improved at the applied site, and dullness and spots are further faded. A single application induced a persistent effect for a week or more.

9.3 Confirming Nasal Effect

The obtained cyclic peptide was prepared in physiological saline at 3, 15, 30, 100 or 500 μg/ml, and 0.1 ml each was applied to nasal cavity. Each of formulations A to E in the table indicates the concentration of the cyclic peptide at 3, 15, 30, 100 or 500 μg/ml, respectively. The absence of the effect upon the application of physiological saline without the peptide confirmed the effect was not a placebo effect.

TABLE 13-1

| SEQ ID NO (amino acid sequence) of cyclic peptides | ID | Sex | Age | Diagnostic impression | Formulation | Treatment | Diagnostic impression on skin after application | Itches after application |
|---|---|---|---|---|---|---|---|---|
| SEQ ID NO 16: (CFVRKMDRISSS SGLGC) | P1 | female | 10's | allergic rhinitis | C | once a day, 0.1 ml applied to each nasal cavity | From immediately after nasal application, and nose got cleared, rhinorrhea stopped. There was no irritationg symptoms, and the effect persisted for all day by 1 nasal application. | Itches were remitted immediately after nasal application, and eliminated after 1 minute. |
| SEQ ID NO 17: (CFGQKMDRISSS SGLGC) | P2 | male | 30's | allergic rhinitis | D | once a day, 0.1 ml applied to each nasal cavity | From immediately after nasal application, and nose got cleared, rhinorrhea stopped. There was no irritationg symptoms, and the effect persisted for all day by 1 nasal application. | Itches were remitted immediately after nasal application, and eliminated after 1 minute. |
| SEQ ID NO 18: (CFGHKMDRISSS SGLGC) | P3 | male | 50's | allergic rhinitis | C | once a day, 0.1 ml applied to each nasal cavity | After 3 minutes, and nose got cleared, rhinorrhea stopped. There was no irritationg symptoms, and the effect persisted for all day by 1 nasal application. | |
| SEQ ID NO 19: (CFGRRMDRISSS SGLGC) | P4 | female | 40's | chronic rhinitis, perennial rhinitis | B | once a day, 0.1 ml applied to each nasal cavity | After 1 minute, and nose got cleared, nasal discharge stopped. There was no irritating symptoms. | |
| | P5 | female | 70's | allergic rhinitis | B | once a day, 0.1 ml applied to each nasal cavity | After 2 minutes, and nose got cleared, and no nasal discharge came out by blowing nose. | Itches were remitted immediately after nasal application. |
| SEQ ID NO 20: (CFGRKLDRISSS SGLGC) | P6 | female | 40's | allergic rhinitis | B | once a day, 0.1 ml applied to each nasal cavity | After 1 minute, nasal obstruction was improved, and nose got cleared. The effect persisted for all day. | |
| SEQ ID NO 21: (CFGRKIDRISSS SGLGC) | P7 | female | 20's | allergic rhinitis | C | once a day, 0.1 ml applied to each nasal cavity | After 1 minute, and nose got cleared. Nasal discharge stopped. | |

TABLE 13-1-continued

| SEQ ID NO (amino acid sequence) of cyclic peptides | ID | Sex | Age | Diagnostic impression | Formulation | Treatment | Diagnostic impression on skin after application | Itches after application |
|---|---|---|---|---|---|---|---|---|
| SEQ ID NO 22: (CFGRKMDRVSSS SGLGC) | P8 | female | 50's | allergic rhinitis | E | once a day, 0.1 ml applied to each nasal cavity | Immediately after nasal application, and nose got cleared. | Immediately after nasal application, restless itches and sneezing stopped. |
| SEQ ID NO 23: (CFGRKMDRVSSS SGLGC) | P9 | female | 40's | chronic rhinitis, perennial rhinitis | C | once a day, 0.1 ml applied to each nasal cavity | After 20 seconds, and nose got cleared. No nasal discharge after 1 minute. There was no irritating symptoms. | |
| SEQ ID NO 23: (CFGRKMDRIGSS SGLGC) | P10 | female | 30's | allergic rhinitis | C | once a day, 0.1 ml applied to each nasal cavity | After 1 minute, and nose got cleared. Nasal discharge stopped. | |
| SEQ ID NO 24: (CFGRKMDRISAS SGLGC) | P11 | female | 20's | allergic rhinitis | C | once a day, 0.1 ml applied to each nasal cavity | After 1 minute, and nose got cleared. Nasal discharge stopped. | |
| SEQ ID NO 25: (CFGRKMDRISSQ SGLGC) | P12 | female | 20's | allergic rhinitis | A | once a day, 0.1 ml applied to each nasal cavity | After 2.5 minutes, and nose got cleared. | |
| SEQ ID NO 26: (CFGRKMDRISSV SGLGC) | P13 | female | 50's | allergic rhinitis | C | once a day, 0.1 ml applied to each nasal cavity | After 1 minute, nose got cleared and refreshed. After 2 minutes, no nasal discharge by blowing. | |
| SEQ ID NO 27: (CFGRKMDRISSL SGLGC) | P14 | male | 20's | allergic rhinitis | C | once a day, 0.1 ml applied to each nasal | After 1 minute, and nose got cleared. | |
| SEQ ID NO 28: (CFGRKMDRISSI SGLGC) | P15 | female | 40's | allergic rhinitis | C | once a day, 0.1 ml applied to each nasal cavity | After 1 minute, and nose got cleared. Nasal discharge stopped. | |
| SEQ ID NO 29: (CFGRKMDRISSM SGLGC) | P16 | male | 50's | allergic rhinitis | C | once a day, 0.1 ml applied to each nasal cavity | After 1 minute, and nose got cleared. Nasal discharge stopped. | |
| SEQ ID NO 30: (CFGRKMDRISSS VGLGC) | P17 | female | 30's | allergic rhinitis | C | once a day, 0.1 ml applied to each nasal cavity | After 1 minute, rhinorrhea stopped. | |
| SEQ ID NO 31: (CFGRKMDRISSS SRLGC) | P18 | female | 10's | allergic rhinitis | D | once a day, 0.1 ml applied to each nasal cavity | After 30 seconds, rhinorrhea stopped. After 1 minute, no nasal discharge by blowing. | |

TABLE 13-1-continued

| SEQ ID NO (amino acid sequence) of cyclic peptides | ID | Sex | Age | Diagnostic impression | Formulation | Treatment | Diagnostic impression on skin after application | Itches after application |
|---|---|---|---|---|---|---|---|---|
| SEQ ID NO 32: (CFGRKMDRISSS SGMGC) | P19 | male | 40's | allergic rhinitis | C | once a day, 0.1 ml applied to each nasal cavity | After 1 minute, nasal obstruction was improved, and nose got cleared. The effect persisted for all day. | |
| | P20 | female | 40's | chronic rhinitis, perennial rhinitis | C | once a day, 0.1 ml applied to each nasal cavity | Immediately after nasal application nose got cleared. The effect was remarkable and persisted for 7 days after 1 nasal application. | Sneezing and itches in deep inside nose stopped. |
| SEQ ID NO 33: (CFGRKMDRISSS SGIGC) | P21 | female | 40's | allergic rhinitis | C | once a day, 0.1 ml applied to each nasal cavity | After 30 seconds, rhinorrhea stopped. After 1 minute, no nasal discharge by blowing. | |
| SEQ ID NO 34: (CFGRKMDRISSS SGVGC) | P22 | female | 40's | allergic rhinitis | C | once a day, 0.1 ml applied to each nasal | After 2.5 minutes, and nose got cleared. | No irritating symptoms. |
| SEQ ID NO 35: (GFGRKMDRISSS SGAGC) | P23 | female | 30's | allergic rhinitis | C | once a day, 0.1 ml applied to each nasal cavity | After 1 minute, nasal obstruction was improved, and nose got cleared. The effect persisted for all day. | |
| | P24 | female | 40's | chronic rhinitis, perennial rhinitis | D | once a day, 0.1 ml applied to each nasal cavity | Immediately after nasal application, nose got refreshed and cleared | |
| SEQ ID NO 36: (CFGRKMDRISSS SGLSC) | P25 | female | 40's | allergic rhinitis | C | once a day, 0.1 ml applied to each nasal cavity | Immediately after nasal application, and nose got cleared. | Immediately after nasal application, itches were removed. No irritating symptoms. |
| | P26 | female | 40's | allergic rhinitis | C | once a day, 0.1 ml applied to each nasal cavity | After 30 seconds, rhinorrhea stopped. Nose got cleared and felt good. Other nose drops causes this subject to sneeze due to some irritant, but the inventive nose drop had no irritation. The effect persisted for 1 week by 1 nasal application. | Immediate effect to remove itches. |
| SEQ ID NO 37: (CFGRKMDRISSS SGLAC) | P27 | female | 40's | chronic rhinitis, perennial rhinitis | C | once a day, 0.1 ml applied to each nasal cavity | Nose got cleared and rhinorrhea stopped in 30 seconds. | |

TABLE 13-1-continued

| SEQ ID NO (amino acid sequence) of cyclic peptides | ID | Sex | Age | Diagnostic impression | Formu-lation | Treatment | Diagnostic impression on skin after application | Itches after application |
|---|---|---|---|---|---|---|---|---|
| SEQ ID NO 38: (CFARKMDRISSS SGLGC) | P28 | male | 30's | chronic rhinitis | C | once a day, 0.1 ml applied to each nasal cavity | After 2 minutes, rhinorrhea stopped. Nasal obstruction was improved to allow nasal breathing. | |
| SEQ ID NO 39: (CFSRKMDRISSS SGLGC) | P29 | male | 40's | allergic rhinitis | C | once a day, 0.1 ml applied to each nasal cavity | Immediately after nasal application, nose got refreshed and cleared. No nasal discharge after 30 seconds. | |
| SEQ ID NO 40: (CFTRKMDRISSS SGLGC) | P30 | female | 30's | allergic rhinitis | C | once a day, 0.1 ml applied to each nasal | After 2.5 minutes, and nose got cleared. | |
| SEQ ID NO 41: (CFGRKMDRISST SGLGC) | P31 | female | 20's | allergic rhinitis | C | once a day, 0.1 ml applied to each nasal cavity | After 1 minute, rhinorrhea stopped. There was no irritating symptoms. | |
| SEQ ID NO 42: (CFGRKMDRISSA SGLGC) | P32 | female | 10's | allergic rhinitis | C | once a day, 0.1 ml applied to each nasal cavity | Immediately after nasal application, and nose got cleared. | |
| SEQ ID NO 43: (CFGRKMDRISSS TGLGC) | P33 | male | 20's | allergic rhinitis | C | once a day, 0.1 ml applied to each nasal cavity | Immediately after nasal application, and nose got cleared. After 1 minute, no nasal discharge even by twisting nose. | |
| SEQ ID NO 44: (CFGRKMDRISSS AGLGC) | P34 | male | 40's | allergic rhinitis | C | once a day, 0.1 ml applied to each nasal cavity | After 1 minute, rhinorrhea stopped. There was no irritating symptoms. | |
| SEQ ID NO 45: (CFSRKMDRISSS SGLGC) | P35 | male | 60's | allergic rhinitis | C | once a day, 0.1 ml applied to each nasal | After 1 minute, and nose got cleared. | |
| SEQ ID NO 47: (CFSRKMDRISSS TGLGC) | P36 | male | 50's | allergic rhinitis | C | once a day, 0.1 ml applied to each nasal cavity | After 1 minute, rhinorrhea stopped. There was no irritating symptoms. | |
| SEQ ID NO 48: (CFSRKMDRISSS SGIGC) | P37 | female | 50's | allergic rhinitis | C | once a day, 0.1 ml applied to each nasal cavity | After 1 minute, and nose got cleared. Nasal discharge stopped. | |

TABLE 13-1-continued

| SEQ ID NO (amino acid sequence) of cyclic peptides | ID | Sex | Age | Diagnostic impression | Formulation | Treatment | Diagnostic impression on skin after application | Itches after application |
|---|---|---|---|---|---|---|---|---|
| SEQ ID NO 49: (CFSRRMDRISSS SGLAC) | P38 | female | 40's | allergic rhinitis | C | once a day, 0.1 ml applied to each nasal cavity | Immediately after nasal application, and nose got cleared. | |
| SEQ ID NO 50: (CFGRRMDRISST SGLGC) | P39 | female | 10's | allergic rhinitis | C | once a day, 0.1 ml applied to each nasal cavity | Immediately after nasal application, and nose got cleared. | |
| SEQ ID NO 51: (CFGRRMDRISSS TGLGC) | P40 | male | 20's | chronic rhinitis | C | once a day, 0.1 ml applied to each nasal cavity | After 1.5 minutes, nasal obstruction was improved, and nose got cleared. | |
| SEQ ID NO 52: (CFGRRMDRISSS SGIGC) | P41 | male | 30's | allergic rhinitis | C | once a day, 0.1 ml applied to each nasal cavity | After 1 minute, rhinorrhea stopped. There was no irritating symptoms. | |
| SEQ ID NO 53: (CFGRRMDRISSS SGLAC) | P42 | male | 40's | allergic rhinitis | C | once a day, 0.1 ml applied to each nasal cavity | Immediately after nasal application, and nose got cleared. | |
| SEQ ID NO 54: (CFGRKMDRISST SGLGC) | P43 | female | 30's | allergic rhinitis | C | once a day, 0.1 ml applied to each nasal cavity | Immediately after nasal application, and nose got cleared. | |
| SEQ ID NO 55: (CFGRKMDRISST SGLAC) | P44 | male | 50's | allergic rhinitis | C | once a day, 0.1 ml applied to each nasal cavity | After 1 minute, and nose got cleared. Nasal discharge stopped. | |
| SEQ ID NO 56: (CFGRKMDRISSS TGIGC) | P45 | male | 30's | allergic rhinitis | C | once a day, 0.1 ml applied to each nasal cavity | Immediately after nasal application, and nose got cleared. | |
| SEQ ID NO 57: (CFGRKMDRISSS TGLAC) | P46 | female | 40's | allergic rhinitis | C | once a day, 0.1 ml applied to each nasal cavity | After 1 minute, and nose got cleared. Nasal discharge stopped. | |
| SEQ ID NO 58: (CFGRKMDRISSS SGIAC) | P47 | female | 40's | allergic rhinitis | C | once a day, 0.1 ml applied to each nasal cavity | After 30 seconds, rhinorrhea stopped, with no more sneezing. There was no irritating symptoms. | Itches were removed in 30 seconds. |
| SEQ ID NO 59: (CFSRRMDRISST SGLGC) | P48 | female | 20's | allergic rhinitis | C | once a day, 0.1 ml applied to each nasal cavity | Immediately after nasal application, and nose got cleared. | |

TABLE 13-1-continued

| SEQ ID NO (amino acid sequence) of cyclic peptides | ID | Sex | Age | Diagnostic impression | Formu-lation | Treatment | Diagnostic impression on skin after application | Itches after application |
|---|---|---|---|---|---|---|---|---|
| SEQ ID NO 60: (CFSRRMDRISSS TGLGC) | P49 | female | 40's | allergic rhinitis | C | once a day, 0.1 ml applied to each nasal cavity | After 1 minute, and nose got cleared. Nasal discharge stopped. | |
| SEQ ID NO 61: (CFSRRMDRIS TABLE 13-1-continued

| SEQ ID NO (amino acid sequence) of cyclic peptides | ID | Sex | Age | Diagnostic impression | Formulation | Treatment | Diagnostic impression on skin after application | Itches after application |
|---|---|---|---|---|---|---|---|---|
| SEQ ID NO 71: (CFSRRMDRISST SGIGC) | P60 | female | 30's | allergic rhinitis | C | once a day, 0.1 ml applied to each nasal cavity | After 1 minute, rhinorrhea stopped, with no more sneezing. There was no irritating symptoms. | |
| SEQ ID NO 72: (CFSRRMDRISST SGLAC) | P61 | female | 40's | allergic rhinitis | C | once a day, 0.1 ml applied to each nasal cavity | After 1 minute, rhinorrhea stopped, with no more sneezing. There was no irritating symptoms. | |
| SEQ ID NO 73: (CFSRRMDRISSS TGIGC) | P62 | female | 20's | allergic rhinitis | C | once a day, 0.1 ml applied to each nasal cavity | Immediately after nasal application, and nose got cleared. | |
| SEQ ID NO 74: (CFSRRMDRISSS TGLAC) | P63 | female | 40's | allergic rhinitis | C | once a day, 0.1 ml applied to each nasal cavity | After 1 minute, rhinorrhea stopped, with no more sneezing. There was no irritating symptoms. | |
| SEQ ID NO 75: (CFSRRMDRISSS SGIAC) | P64 | male | 20's | allergic rhinitis | C | once a day, 0.1 ml applied to each nasal cavity | After 1 minute, and nose got cleared. Nasal discharge stopped. | |

In SEQ ID NOS 16-75, 1st Cys and 17th Cys from left form a disulfide bond.

The result described above demonstrated that the cyclic peptide of the invention exhibits a similar effect as the cyclic peptide expressed by Formula I-a even if some amino acids of the cyclic peptide have been replaced.

Specifically, when it was applied to nasal cavity mucosa and/or paranasal cavity mucosa, it can improve or prevent various symptoms associated with rhinitis such as nasal obstruction, rhinorrhea, sneezing and pruritus. Rhinitis also includes, without being particularly limited, for example, infectious rhinitis including acute rhinitis and chronic rhinitis; hypersensitive non-infectious rhinitis including combined (flower hypersensitivity) rhinitis, rhinitis with rhinorrhea, congestive rhinitis, edematous rhinitis and dry-nose type rhinitis; irritant-induced rhinitis including physical rhinitis, chemical rhinitis and radiation rhinitis; and atrophic rhinitis and idiopathic granulomatous rhinitis; sinusitis such as acute sinusitis, chronic sinusitis (maxillary empyema), eosinophilic sinusitis and paranasal cavity mycosis. The external preparation can be used for the purpose of treating or preventing one ore more of the above.

Combined rhinitis includes, for example, allergic rhinitis including perennial allergic rhinitis and seasonal allergic rhinitis, and nonallergic rhinitis including vasomotor (essential) rhinitis and eosinophilic rhinitis. Rhinitis with rhinorrhea includes, for example, gustatory rhinitis, cold air-induced rhinitis and senile rhinitis.

Congestive rhinitis includes, for example, drug-induced rhinitis, psychogenic rhinitis, gestational rhinitis, endocrine rhinitis and cold rhinitis.

Edematous rhinitis includes, for example, aspirin-hypersensitive rhinitis.

Among those mentioned above, it exerts an excellent effect specifically on hypersensitive non-infectious rhinitis, irritant-induced rhinitis and sinusitis, preferably on hypersensitive non-infectious rhinitis and chronic sinusitis, more preferably on combined (flower hypersensitivity) rhinitis, rhinitis with rhinorrhea, congestive rhinitis, edematous rhinitis and dry-nose type rhinitis, and chronic sinusitis. Therefore, the external preparation of the present invention can be used for the purpose of treating or preventing at least one or more rhinitis selected from the above-mentioned group.

In terms of its symptoms, for its effects as described above, it can be used for any of rhinitis with sneezing/rhinorrhea, rhinitis with nasal obstruction and rhinitis with both symptoms.

Immediately after a single application of 0.1 ml of 3 µg/ml to 500 µg/ml preparation was applied to the affected site in each nasal cavity, nasal discharge was stopped, nasal obstruction was improved, itches in nasal cavity mucosa or sneezing were stopped (immediate effect). A single application of a nasal drop induced persistent effects lasting for one day, or for a week or more in some cases (long-lasting effect). In addition, because it causes no local irritation at all, it can be used safely even in a subject who is not desired to use a nasal drop comprising rhinitis therapeutic that has conventionally been used such as steroid drug due to its strong local irritation.

Examples of multiple replaceable amino acids in the cyclic peptide of the invention are summarized below, based on working examples as described above, without not being limited thereto.

TABLE 32

Candidate multiple replacements of B ring

| Number of replacement | Residue ID | Amino acid | Residue ID | Amino acid | Residue ID | Amino acid | Residue ID | Amino acid | Example of replaced amino acid sequence | SEQ ID NO: |
|---|---|---|---|---|---|---|---|---|---|---|
| 2 | 3 | A, S | 5 | R | | | | | CFSRRMDRISSSSGLGC | 45 |
| | 3 | A, S | 12 | Q, T | | | | | CFSRKMDRISSTSGLGC | 46 |
| | 3 | A, S | 13 | T | | | | | CFSRKMDRISSSTGLGC | 47 |
| | 3 | A, S | 15 | M, I, V, A | | | | | CFSRKMDRISSSSGIGC | 48 |
| | 3 | A, S | 16 | A, S | | | | | CFSRKMDRISSSSGLAC | 49 |
| | 5 | R | 12 | Q, T | | | | | CFGRRMDRISSTSGLGC | 50 |
| | 5 | R | 13 | T | | | | | CFGRRMDRISSSTGLGC | 51 |
| | 5 | R | 15 | M, I, V, A | | | | | CFGRRMDRISSSSGIGC | 52 |
| | 5 | R | 16 | A, S | | | | | CFCRRMDRISSSSGLAC | 53 |
| | 12 | Q, T | 15 | M, I, V, A | | | | | CFGRKMDRISSTSGIGC | 54 |
| | 12 | Q, T | 16 | A, S | | | | | CFGRKMDRISSTSGLAC | 55 |
| | 13 | T | 15 | M, I, V, A | | | | | CFGRKMDRISSSTGIGC | 56 |
| | 13 | T | 16 | A, S | | | | | CFGRKMDRISSSTGLAC | 57 |
| | 15 | M, I, V, A | 16 | A, S | | | | | CFGRKMDRISSSSGIAC | 58 |

TABLE 32-continued

Candidate multiple replacements of B ring

| Number of replace-ment | Resi-due ID | Amino acid | Resi-due ID | Amino acid | Resi-due ID | Amino acid | Resi-due ID | Amino acid | Example of replaced amino acid sequence | SEQ ID NO: |
|---|---|---|---|---|---|---|---|---|---|---|
| 3 | 3 | A, S | 5 | R | 12 | Q, T | | | CFSRRMDRISSTSGLGC | 59 |
| | 3 | A, S | 5 | R | 13 | T | | | CFSRRMDRISSSTGLGC | 60 |
| | 3 | A, S | 5 | R | 15 | M, I, V, A

```
<223> OTHER INFORMATION: Xaa can be Met, Leu, or Ile
<220> FEATURE:
<221> NAME/KEY: misc_feature
<222> LOCATION: (9)..(9)
<223> OTHER INFORMATION: Xaa can be Ile or Val
<220> FEATURE:
<221> NAME/KEY: misc_feature
<222> LOCATION: (10)..(10)
<223> OTHER INFORMATION: Xaa can be Ser or Gly
<220> FEATURE:
<221> NAME/KEY: misc_feature
<222> LOCATION: (11)..(11)
<223> OTHER INFORMATION: Xaa can be Ser or Ala
<220> FEATURE:
<221> NAME/KEY: misc_feature
<222> LOCATION: (12)..(12)
<223> OTHER INFORMATION: Xaa can be Ser, Gln, Val, Ala, Thr, Leu, Ile,
      or Met
<220> FEATURE:
<221> NAME/KEY: misc_feature
<222> LOCATION: (13)..(13)
<223> OTHER INFORMATION: Xaa can be Ser, Val, Ala, or Thr
<220> FEATURE:
<221> NAME/KEY: misc_feature
<222> LOCATION: (14)..(14)
<223> OTHER INFORMATION: Xaa can be Gly or Arg
<220> FEATURE:
<221> NAME/KEY: misc_feature
<222> LOCATION: (15)..(15)
<223> OTHER INFORMATION: Xaa can be Leu, Met, Ile, Val, or Ala
<220> FEATURE:
<221> NAME/KEY: misc_feature
<222> LOCATION: (16)..(16)
<223> OTHER INFORMATION: Xaa can be Gly, Ser, or Ala

<400> SEQUENCE: 1

Cys Phe Xaa Xaa Xaa Xaa Asp Arg Xaa Xaa Xaa Xaa Xaa Xaa Xaa Xaa
1               5                   10                  15

Cys

<210> SEQ ID NO 2
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: misc_feature
<222> LOCATION: (3)..(3)
<223> OTHER INFORMATION: Xaa can be Gly, Val, Ala, Ser, or Thr
<220> FEATURE:
<221> NAME/KEY: misc_feature
<222> LOCATION: (5)..(5)
<223> OTHER INFORMATION: Xaa can be Lys or Arg
<220> FEATURE:
<221> NAME/KEY: misc_feature
<222> LOCATION: (9)..(9)
<223> OTHER INFORMATION: Xaa can be Ile or Val
<220> FEATURE:
<221> NAME/KEY: misc_feature
<222> LOCATION: (12)..(12)
<223> OTHER INFORMATION: Xaa can be Ser, Gln, Val, Ala, Thr, Leu, Ile,
      or Met
<220> FEATURE:
<221> NAME/KEY: misc_feature
<222> LOCATION: (13)..(13)
<223> OTHER INFORMATION: Xaa can be Ser, Val, Ala, or Thr
<220> FEATURE:
<221> NAME/KEY: misc_feature
<222> LOCATION: (15)..(15)
<223> OTHER INFORMATION: Xaa can be Leu, Met, Ile, Val, or Ala
<220> FEATURE:
<221> NAME/KEY: misc_feature
```

```
<222> LOCATION: (16)..(16)
<223> OTHER INFORMATION: Xaa can be Gly, Ser, or Ala

<400> SEQUENCE: 2

Cys Phe Xaa Arg Xaa Met Asp Arg Xaa Ser Ser Xaa Xaa Gly Xaa Xaa
1               5                   10                  15

Cys

<210> SEQ ID NO 3
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 3

Cys Phe Gly Arg Lys Met Asp Arg Ile Ser Ser Ser Ser Gly Leu Gly
1               5                   10                  15

Cys

<210> SEQ ID NO 4
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from porcine

<400> SEQUENCE: 4

Cys Phe Gly Arg Arg Leu Asp Arg Ile Gly Ser Leu Ser Gly Leu Gly
1               5                   10                  15

Cys

<210> SEQ ID NO 5
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from rat

<400> SEQUENCE: 5

Cys Phe Gly Gln Lys Ile Asp Arg Ile Gly Ala Val Ser Arg Leu Gly
1               5                   10                  15

Cys

<210> SEQ ID NO 6
<211> LENGTH: 17
```

```
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from canine

<400> SEQUENCE: 6

Cys Phe Gly Arg Arg Leu Asp Arg Ile Gly Ser Leu Ser Gly Leu Gly
1               5                   10                  15

Cys

<210> SEQ ID NO 7
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from mouse

<400> SEQUENCE: 7

Cys Phe Gly His Lys Ile Asp Arg Ile Gly Ser Val Ser Arg Leu Gly
1               5                   10                  15

Cys

<210> SEQ ID NO 8
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from chick

<400> SEQUENCE: 8

Cys Phe Gly Arg Arg Ile Asp Arg Ile Gly Ser Leu Ser Gly Met Gly
1               5                   10                  15

Cys

<210> SEQ ID NO 9
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from bovine

<400> SEQUENCE: 9
```

-continued

```
Cys Phe Gly Arg Arg Leu Asp Arg Ile Gly Ser Leu Ser Gly Leu Gly
1               5                   10                  15

Cys

<210> SEQ ID NO 10
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from cat

<400> SEQUENCE: 10

Cys Phe Gly Arg Arg Leu Asp Arg Ile Gly Ser Leu Ser Gly Leu Gly
1               5                   10                  15

Cys

<210> SEQ ID NO 11
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from dog

<400> SEQUENCE: 11

Cys Phe Gly Arg Arg Leu Asp Arg Ile Gly Ser Leu Ser Gly Leu Gly
1               5                   10                  15

Cys

<210> SEQ ID NO 12
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from sheep

<400> SEQUENCE: 12

Cys Phe Gly Arg Arg Leu Asp Arg Ile Gly Ser Leu Ser Gly Leu Gly
1               5                   10                  15

Cys

<210> SEQ ID NO 13
<211> LENGTH: 32
<212> TYPE: PRT
<213> ORGANISM: Homo sapiens
<220> FEATURE:
<221> NAME/KEY: DISULFID
```

```
<222> LOCATION: (10)..(26)

<400> SEQUENCE: 13

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 14
<211> LENGTH: 21
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(21)
<223> OTHER INFORMATION: derived from Homo sapiens

<400> SEQUENCE: 14

Cys Phe Gly Arg Lys Met Asp Arg Ile Ser Ser Ser Ser Gly Leu Gly
1               5                   10                  15

Cys Lys Val Leu Arg
            20

<210> SEQ ID NO 15
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 15

Cys Phe Gly Arg Lys Met Asp Arg Ile Ser Ser Ser Ser Gly Leu Gly
1               5                   10                  15

Cys

<210> SEQ ID NO 16
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 16

Cys Phe Val Arg Lys Met Asp Arg Ile Ser Ser Ser Ser Gly Leu Gly
1               5                   10                  15

Cys

<210> SEQ ID NO 17
```

```
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)

<400> SEQUENCE: 17

Cys Phe Gly Gln Lys Met Asp Arg Ile Ser Ser Ser Ser Gly Leu Gly
1               5                   10                  15

Cys

<210> SEQ ID NO 18
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 18

Cys Phe Gly His Lys Met Asp Arg Ile Ser Ser Ser Ser Gly Leu Gly
1               5                   10                  15

Cys

<210> SEQ ID NO 19
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 19

Cys Phe Gly Arg Arg Met Asp Arg Ile Ser Ser Ser Ser Gly Leu Gly
1               5                   10                  15

Cys

<210> SEQ ID NO 20
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 20
```

```
Cys Phe Gly Arg Lys Leu Asp Arg Ile Ser Ser Ser Gly Leu Gly
1               5                   10                  15

Cys

<210> SEQ ID NO 21
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 21

Cys Phe Gly Arg Lys Ile Asp Arg Ile Ser Ser Ser Gly Leu Gly
1               5                   10                  15

Cys

<210> SEQ ID NO 22
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 22

Cys Phe Gly Arg Lys Met Asp Arg Val Ser Ser Ser Gly Leu Gly
1               5                   10                  15

Cys

<210> SEQ ID NO 23
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 23

Cys Phe Gly Arg Lys Met Asp Arg Ile Gly Ser Ser Gly Leu Gly
1               5                   10                  15

Cys

<210> SEQ ID NO 24
<211> LENGTH: 17
<212> TYPE: PRT
<213> ORGANISM: Artificial Sequence
<220> FEATURE:
<223> OTHER INFORMATION: synthetic peptide
```

```
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 24

Cys Phe Gly Arg Lys Met Asp Arg Ile Ser Ala Ser Ser Gly Leu Gly
1               5                   10                  15

Cys

<210> SEQ ID NO 25
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 25

Cys Phe Gly Arg Lys Met Asp Arg Ile Ser Ser Gln Ser Gly Leu Gly
1               5                   10                  15

Cys

<210> SEQ ID NO 26
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 26

Cys Phe Gly Arg Lys Met Asp Arg Ile Ser Ser Val Ser Gly Leu Gly
1               5                   10                  15

Cys

<210> SEQ ID NO 27
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 27

Cys Phe Gly Arg Lys Met Asp Arg Ile Ser Ser Leu Ser Gly Leu Gly
1               5                   10                  15
```

Cys

```
<210> SEQ ID NO 28
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 28

Cys Phe Gly Arg Lys Met Asp Arg Ile Ser Ser Ile Ser Gly Leu Gly
1               5                   10                  15

Cys

<210> SEQ ID NO 29
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 29

Cys Phe Gly Arg Lys Met Asp Arg Ile Ser Ser Met Ser Gly Leu Gly
1               5                   10                  15

Cys

<210> SEQ ID NO 30
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 30

Cys Phe Gly Arg Lys Met Asp Arg Ile Ser Ser Ser Val Gly Leu Gly
1               5                   10                  15

Cys

<210> SEQ ID NO 31
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
```

```
<221> NAME/KEY: MISC_FEATURE
<222> LOCATION: (1)..(17)
<223> OTHER INFORMATION: derived from Homo sapiens

<400> SEQUENCE: 31

Cys Phe Gly Arg Lys Met Asp Arg Ile Ser Ser Ser Ser Arg Leu Gly
1               5                   10                  15

Cys

<210> SEQ ID NO 32
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 32

Cys Phe Gly Arg Lys Met Asp Arg Ile Ser Ser Ser Ser Gly Met Gly
1               5                   10                  15

Cys

<210> SEQ ID NO 33
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 33

Cys Phe Gly Arg Lys Met Asp Arg Ile Ser Ser Ser Ser Gly Ile Gly
1               5                   10                  15

Cys

<210> SEQ ID NO 34
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 34

Cys Phe Gly Arg Lys Met Asp Arg Ile Ser Ser Ser Ser Gly Val Gly
1               5                   10                  15

Cys

<210> SEQ ID NO 35
```

```
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 35

Cys Phe Gly Arg Lys Met Asp Arg Ile Ser Ser Ser Ser Gly Ala Gly
1               5                   10                  15

Cys

<210> SEQ ID NO 36
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 36

Cys Phe Gly Arg Lys Met Asp Arg Ile Ser Ser Ser Ser Gly Leu Ser
1               5                   10                  15

Cys

<210> SEQ ID NO 37
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 37

Cys Phe Gly Arg Lys Met Asp Arg Ile Ser Ser Ser Ser Gly Leu Ala
1               5                   10                  15

Cys

<210> SEQ ID NO 38
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens
```

```
<400> SEQUENCE: 38

Cys Phe Ala Arg Lys Met Asp Arg Ile Ser Ser Ser Ser Gly Leu Gly
1               5                   10                  15

Cys

<210> SEQ ID NO 39
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 39

Cys Phe Ser Arg Lys Met Asp Arg Ile Ser Ser Ser Ser Gly Leu Gly
1               5                   10                  15

Cys

<210> SEQ ID NO 40
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 40

Cys Phe Thr Arg Lys Met Asp Arg Ile Ser Ser Ser Ser Gly Leu Gly
1               5                   10                  15

Cys

<210> SEQ ID NO 41
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 41

Cys Phe Gly Arg Lys Met Asp Arg Ile Ser Ser Thr Ser Gly Leu Gly
1               5                   10                  15

Cys

<210> SEQ ID NO 42
<211> LENGTH: 17
<212> TYPE: PRT
<213> ORGANISM: Artificial Sequence
<220> FEATURE:
```

```
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 42

Cys Phe Gly Arg Lys Met Asp Arg Ile Ser Ser Ala Ser Gly Leu Gly
1               5                   10                  15

Cys

<210> SEQ ID NO 43
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 43

Cys Phe Gly Arg Lys Met Asp Arg Ile Ser Ser Ser Thr Gly Leu Gly
1               5                   10                  15

Cys

<210> SEQ ID NO 44
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 44

Cys Phe Gly Arg Lys Met Asp Arg Ile Ser Ser Ser Ala Gly Leu Gly
1               5                   10                  15

Cys

<210> SEQ ID NO 45
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 45

Cys Phe Ser Arg Arg Met Asp Arg Ile Ser Ser Ser Ser Gly Leu Gly
1               5                   10                  15
```

Cys

<210> SEQ ID NO 46
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 46

Cys Phe Ser Arg Lys Met Asp Arg Ile Ser Ser Thr Ser Gly Leu Gly
1               5                   10                  15

Cys

<210> SEQ ID NO 47
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 47

Cys Phe Ser Arg Lys Met Asp Arg Ile Ser Ser Ser Thr Gly Leu Gly
1               5                   10                  15

Cys

<210> SEQ ID NO 48
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 48

Cys Phe Ser Arg Lys Met Asp Arg Ile Ser Ser Ser Ser Gly Ile Gly
1               5                   10                  15

Cys

<210> SEQ ID NO 49
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)

```
<220> FEATURE:
<221> NAME/KEY: MISC_FEATURE
<222> LOCATION: (1)..(17)
<223> OTHER INFORMATION: derived from Homo sapiens

<400> SEQUENCE: 49

Cys Phe Ser Arg Lys Met Asp Arg Ile Ser Ser Ser Ser Gly Leu Ala
1               5                   10                  15
Cys

<210> SEQ ID NO 50
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 50

Cys Phe Gly Arg Arg Met Asp Arg Ile Ser Ser Thr Ser Gly Leu Gly
1               5                   10                  15
Cys

<210> SEQ ID NO 51
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 51

Cys Phe Gly Arg Arg Met Asp Arg Ile Ser Ser Ser Thr Gly Leu Gly
1               5                   10                  15
Cys

<210> SEQ ID NO 52
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 52

Cys Phe Gly Arg Arg Met Asp Arg Ile Ser Ser Ser Ser Gly Ile Gly
1               5                   10                  15
Cys
```

```
<210> SEQ ID NO 53
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 53

Cys Phe Gly Arg Arg Met Asp Arg Ile Ser Ser Ser Ser Gly Leu Ala
1               5                   10                  15

Cys

<210> SEQ ID NO 54
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 54

Cys Phe Gly Arg Lys Met Asp Arg Ile Ser Ser Thr Ser Gly Ile Gly
1               5                   10                  15

Cys

<210> SEQ ID NO 55
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 55

Cys Phe Gly Arg Lys Met Asp Arg Ile Ser Ser Thr Ser Gly Leu Ala
1               5                   10                  15

Cys

<210> SEQ ID NO 56
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens
```

```
<400> SEQUENCE: 56

Cys Phe Gly Arg Lys Met Asp Arg Ile Ser Ser Ser Thr Gly Ile Gly
1               5                   10                  15

Cys

<210> SEQ ID NO 57
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 57

Cys Phe Gly Arg Lys Met Asp Arg Ile Ser Ser Ser Thr Gly Leu Ala
1               5                   10                  15

Cys

<210> SEQ ID NO 58
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 58

Cys Phe Gly Arg Lys Met Asp Arg Ile Ser Ser Ser Ser Gly Ile Ala
1               5                   10                  15

Cys

<210> SEQ ID NO 59
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 59

Cys Phe Ser Arg Arg Met Asp Arg Ile Ser Ser Thr Ser Gly Leu Gly
1               5                   10                  15

Cys

<210> SEQ ID NO 60
<211> LENGTH: 17
<212> TYPE: PRT
<213> ORGANISM: Artificial Sequence
```

```
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 60

Cys Phe Ser Arg Arg Met Asp Arg Ile Ser Ser Ser Thr Gly Leu Gly
1               5                   10                  15

Cys

<210> SEQ ID NO 61
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 61

Cys Phe Ser Arg Arg Met Asp Arg Ile Ser Ser Ser Gly Ile Gly
1               5                   10                  15

Cys

<210> SEQ ID NO 62
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 62

Cys Phe Ser Arg Arg Met Asp Arg Ile Ser Ser Ser Gly Leu Ala
1               5                   10                  15

Cys

<210> SEQ ID NO 63
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 63

Cys Phe Ser Arg Lys Met Asp Arg Ile Ser Ser Thr Ser Gly Ile Gly
```

-continued

```
1               5                   10                  15

Cys

<210> SEQ ID NO 64
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 64

Cys Phe Ser Arg Lys Met Asp Arg Ile Ser Ser Ser Thr Gly Ile Gly
1               5                   10                  15

Cys

<210> SEQ ID NO 65
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 65

Cys Phe Ser Arg Lys Met Asp Arg Ile Ser Ser Ser Thr Gly Leu Ala
1               5                   10                  15

Cys

<210> SEQ ID NO 66
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 66

Cys Phe Ser Arg Lys Met Asp Arg Ile Ser Ser Ser Ser Gly Ile Ala
1               5                   10                  15

Cys

<210> SEQ ID NO 67
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
```

```
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 67

Cys Phe Gly Arg Arg Met Asp Arg Ile Ser Ser Thr Ser Gly Ile Gly
1               5                   10                  15

Cys

<210> SEQ ID NO 68
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 68

Cys Phe Gly Arg Arg Met Asp Arg Ile Ser Ser Thr Ser Gly Leu Ala
1               5                   10                  15

Cys

<210> SEQ ID NO 69
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 69

Cys Phe Gly Arg Arg Met Asp Arg Ile Ser Ser Ser Thr Gly Ile Gly
1               5                   10                  15

Cys

<210> SEQ ID NO 70
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 70

Cys Phe Gly Arg Arg Met Asp Arg Ile Ser Ser Ser Thr Gly Leu Ala
1               5                   10                  15

Cys
```

<210> SEQ ID NO 71
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 71

Cys Phe Ser Arg Arg Met Asp Arg Ile Ser Ser Thr Ser Gly Ile Gly
1               5                   10                  15

Cys

<210> SEQ ID NO 72
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 72

Cys Phe Ser Arg Arg Met Asp Arg Ile Ser Ser Thr Ser Gly Leu Ala
1               5                   10                  15

Cys

<210> SEQ ID NO 73
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 73

Cys Phe Ser Arg Arg Met Asp Arg Ile Ser Ser Ser Thr Gly Ile Gly
1               5                   10                  15

Cys

<210> SEQ ID NO 74
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)

```
<223> OTHER INFORMATION: derived from Homo sapiens

<400> SEQUENCE: 74

Cys Phe Ser Arg Arg Met Asp Arg Ile Ser Ser Ser Thr Gly Leu Ala
1               5                   10                  15

Cys

<210> SEQ ID NO 75
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: DISULFID
<222> LOCATION: (1)..(17)
<220> FEATURE:
<221> NAME/KEY: MISC_FEATURE
<222> LOCATION: (1)..(17)
<223> OTHER INFORMATION: derived from Homo sapiens

<400> SEQUENCE: 75

Cys Phe Ser Arg Arg Met Asp Arg Ile Ser Ser Ser Ser Gly Ile Ala
1               5                   10                  15

Cys

<210> SEQ ID NO 76
<211> LENGTH: 17
<212> TYPE: PRT
<213> ORGANISM: Artificial Sequence
<220> FEATURE:
<223> OTHER INFORMATION: synthetic peptide

<400> SEQUENCE: 76

Cys Phe Gly Arg Arg Met Asp Arg Ile Ser Ser Ser Ser Gly Ile Ala
1               5                   10                  15

Cys
```

The invention claimed is:

1. A method of using an external preparation comprising applying the external preparation to skin and/or mucosa of a subject, wherein the external preparation comprises a cyclic peptide having an amino acid sequence as shown in SEQ ID NO: 1 and expressed by the Formula I:

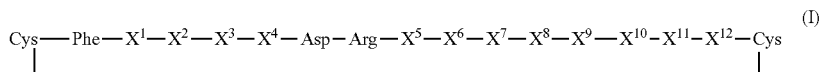

wherein,
$X^1$ denotes Gly, Val, Ala, Ser or Thr,
$X^2$ denotes Arg, His, or Gln,
$X^3$ denotes Lys or Arg,
$X^4$ denotes Met or Leu,
$X^5$ denotes Ile or Val,
$X^6$ denotes Ser or Gly,
$X^7$ denotes Ser,
$X^8$ denotes Ser, Gln, Val, Ala, Thr, Leu, Ile or Met,
$X^9$ denotes Ser, Val, Ala or Thr,
$X^{10}$ denotes Gly or Arg,
$X^{11}$ denotes Leu, Met, Ile, Val or Ala,
$X^{12}$ denotes Gly, Ser or Ala, and
the line connecting two Cys denotes a disulfide bond, and wherein said amino acid sequence does not have a peptide bond that is not between the amino acids constituting said amino acid sequence,
or a derivative thereof or a pharmaceutically acceptable salt thereof, and wherein the external preparation is used for treating alopecia, and/or for stimulating hair growth, and/or for growing hair, and/or for providing hair resilience and elasticity, and/or for increasing volume of hair, and/or for decreasing falling hairs;
wherein the cyclic peptide has an amino acid sequence of any one of SEQ ID NOs: 3, 16-19, 22, 23, or 25-75, or a derivative thereof or a pharmaceutically acceptable salt thereof.

2. The method according to claim 1, wherein the derivative is substituted by a substituent which is capable of replacing a hydrogen atom, a hydroxyl group, a carboxy group or an amino group in the cyclic peptide.

3. The method according to claim 1, wherein the external preparation is a bath agent, a body-cleansing agent or a hair-cleansing agent.

4. The method according to claim 1, wherein the external preparation is an alopecia therapeutic, a hair growing agent and/or a hair growth stimulant.

5. The method according to claim 1, wherein the external preparation is a solid, semi-solid, powder, liquid, spray, ointment, cream, emulsion, gel or patch formulation.

6. The method according to claim 1, wherein the external preparation is used as a pharmaceutical product, a quasi-drug or a cosmetic product.

\* \* \* \* \*